United States Patent
Li et al.

(10) Patent No.: US 11,697,683 B2
(45) Date of Patent: Jul. 11, 2023

(54) ANTI-IL31 ANTIBODIES FOR VETERINARY USE

(71) Applicant: Kindred Biosciences, Inc., Burlingame, CA (US)

(72) Inventors: Shyr Jiann Li, Millbrae, CA (US); Lam Nguyen, Union City, CA (US); Hangjun Zhan, Foster City, CA (US)

(73) Assignee: Kindred Biosciences, Inc., Burlingame, CA (US)

( * ) Notice: Subject to any disclaimer, the term of this patent is extended or adjusted under 35 U.S.C. 154(b) by 401 days.

(21) Appl. No.: 17/039,495

(22) Filed: Sep. 30, 2020

(65) Prior Publication Data

US 2021/0163587 A1 Jun. 3, 2021

Related U.S. Application Data

(62) Division of application No. 16/186,013, filed on Nov. 9, 2018, now abandoned, which is a division of application No. 15/844,142, filed on Dec. 15, 2017, now Pat. No. 10,150,810, which is a division of application No. 15/467,464, filed on Mar. 23, 2017, now Pat. No. 10,093,731.

(60) Provisional application No. 62/463,543, filed on Feb. 24, 2017.

(51) Int. Cl.
*C07K 16/24* (2006.01)
*A61K 39/00* (2006.01)

(52) U.S. Cl.
CPC ...... *C07K 16/244* (2013.01); *A61K 2039/552* (2013.01); *C07K 2317/24* (2013.01); *C07K 2317/33* (2013.01); *C07K 2317/34* (2013.01); *C07K 2317/52* (2013.01); *C07K 2317/56* (2013.01); *C07K 2317/565* (2013.01); *C07K 2317/76* (2013.01); *C07K 2317/92* (2013.01); *C07K 2317/94* (2013.01)

(58) Field of Classification Search
CPC ................................ C12N 15/00; C12N 15/09
See application file for complete search history.

(56) References Cited

U.S. PATENT DOCUMENTS

| | | |
|---|---|---|
| 5,760,185 A | 6/1998 | Kimachi et al. |
| 5,795,965 A | 8/1998 | Tsuchiya et al. |
| 6,194,551 B1 | 2/2001 | Idusogie et al. |
| 7,514,077 B2 | 4/2009 | Yao et al. |
| 7,531,636 B2 | 5/2009 | Sprecher et al. |
| 7,531,637 B2 | 5/2009 | Siadak et al. |
| 7,615,213 B2 | 11/2009 | Kasaian et al. |
| 7,638,126 B2 | 12/2009 | Yao et al. |
| 7,939,068 B2 | 5/2011 | Yao et al. |
| 8,017,122 B2 | 9/2011 | Siadak et al. |
| 8,101,183 B2 | 1/2012 | Siadak et al. |
| 8,105,590 B2 | 1/2012 | Yao et al. |
| 8,133,899 B2 | 3/2012 | Mitton-Fry et al. |
| 8,377,438 B2 | 2/2013 | Yao et al. |
| 8,388,964 B2 | 3/2013 | Leung et al. |
| 8,460,667 B2 | 6/2013 | Blanc et al. |
| 8,466,262 B2 | 6/2013 | Siadak et al. |
| 8,470,979 B2 | 6/2013 | Bondensgaard et al. |
| 8,568,723 B2 | 10/2013 | Siadak et al. |
| 8,637,015 B2 | 1/2014 | Yao et al. |
| 8,790,651 B2 | 7/2014 | Bammert et al. |
| 8,968,732 B2 | 3/2015 | Yao et al. |
| 9,156,909 B2 | 10/2015 | Siadak et al. |
| 9,206,253 B2 | 12/2015 | Bammert et al. |
| 9,328,164 B2 | 5/2016 | Gearing |
| 9,409,986 B2 | 8/2016 | Wu et al. |
| 9,447,183 B2 | 9/2016 | Wu et al. |
| 9,447,184 B2 | 9/2016 | Wu et al. |
| 9,512,219 B2 | 12/2016 | Siadak et al. |
| 9,556,280 B2 | 1/2017 | Murphy et al. |
| 9,592,293 B2 | 3/2017 | Wu et al. |
| 9,605,062 B2 | 3/2017 | Sprecher et al. |
| 9,683,037 B2 | 6/2017 | Siadak et al. |
| 9,822,177 B2 | 11/2017 | Siadak et al. |
| 10,011,647 B2 | 7/2018 | Murphy et al. |
| 10,086,076 B2 | 10/2018 | Wu et al. |
| 10,093,731 B2 | 10/2018 | Li et al. |
| 10,150,810 B2 | 12/2018 | Li et al. |
| 10,259,868 B2 | 4/2019 | Siadak et al. |
| 10,273,297 B2 | 4/2019 | Siadak et al. |
| 10,633,449 B2 | 4/2020 | Shih et al. |
| 10,669,337 B2 | 6/2020 | Irving et al. |
| 10,815,305 B2 | 10/2020 | Orengo et al. |
| 10,836,796 B2 | 11/2020 | Zhao et al. |
| 10,845,365 B2 | 11/2020 | Datta et al. |
| 2003/0224487 A1 | 12/2003 | Sprecher et al. |
| 2006/0073145 A1 | 4/2006 | Leturcq et al. |

(Continued)

FOREIGN PATENT DOCUMENTS

| | | |
|---|---|---|
| AU | 2013203075 | 5/2013 |
| CN | 1612689 A | 5/2005 |

(Continued)

OTHER PUBLICATIONS

Anti-Feline IL-31 Functional Assay Data, filed in Opposition in EP 3219729 on Nov. 25, 2022 (1 page).
EMBOSS Needle alignment IL-31_felis catus (SEQ ID N0.70)_ 1L-31 canis lupus, Rundate: Oct. 31, 2021 (1 page).
King, Stephen, et al. "A randomized double-blinded placebo-controlled study to evaluate an effective ciclosporin dose for the treatment of feline hypersensitivity dermatitis" Veterinary Dermatology, vol. 23, pp. 440-e84, Oct. 2012.

(Continued)

*Primary Examiner* — Prema M Mertz
(74) *Attorney, Agent, or Firm* — McBee Moore & Vanik IP, LLC

(57) ABSTRACT

Provided are various embodiments relating to anti-IL31 antibodies binding to canine IL31. Such antibodies can be used in methods to treat IL31-induced conditions in companion animals, such as canines, felines, and equines.

20 Claims, 7 Drawing Sheets

Specification includes a Sequence Listing.

(56) References Cited

U.S. PATENT DOCUMENTS

| | | |
|---|---|---|
| 2006/0141579 A1 | 6/2006 | Sprecher et al. |
| 2006/0182743 A1 | 8/2006 | Bilsborough |
| 2006/0228329 A1 | 10/2006 | Brady et al. |
| 2006/0275296 A1 | 12/2006 | Siadak et al. |
| 2007/0160610 A1 | 7/2007 | Yao et al. |
| 2007/0160611 A1 | 7/2007 | Yao et al. |
| 2008/0260686 A1 | 10/2008 | Bilsborough et al. |
| 2009/0110685 A1 | 4/2009 | Patel et al. |
| 2009/0208494 A1 | 8/2009 | Bondensgaard et al. |
| 2009/0220417 A1 | 9/2009 | Siadak et al. |
| 2009/0252732 A1 | 10/2009 | Siadak et al. |
| 2009/0280121 A1 | 11/2009 | Leung et al. |
| 2009/0300776 A1 | 12/2009 | Lecron et al. |
| 2010/0061988 A1 | 3/2010 | Hansen |
| 2010/0075996 A1 | 3/2010 | Mitton-Fry et al. |
| 2010/0221244 A1 | 9/2010 | Yao et al. |
| 2010/0297125 A1 | 11/2010 | Yao et al. |
| 2011/0008820 A1 | 1/2011 | Bilsborough et al. |
| 2011/0123440 A1 | 5/2011 | Hansen et al. |
| 2011/0165063 A1 | 7/2011 | Hsieh et al. |
| 2011/0177072 A1 | 7/2011 | Yao et al. |
| 2011/0287454 A1 | 11/2011 | Wagner |
| 2011/0293514 A1 | 12/2011 | Siadak et al. |
| 2011/0318343 A1 | 12/2011 | Kaisheva et al. |
| 2012/0083456 A1 | 4/2012 | Bilsborough et al. |
| 2012/0100155 A1 | 4/2012 | Stoloff et al. |
| 2012/0107310 A1 | 5/2012 | Yao et al. |
| 2012/0275996 A1 | 11/2012 | Hsieh |
| 2013/0022616 A1 | 1/2013 | Bammert et al. |
| 2013/0177563 A1 | 7/2013 | Leung et al. |
| 2013/0216542 A1 | 8/2013 | Siadak et al. |
| 2013/0266562 A1 | 10/2013 | Siadak et al. |
| 2013/0295611 A1 | 11/2013 | Bondensgaard et al. |
| 2014/0271658 A1 | 9/2014 | Murphy et al. |
| 2014/0286958 A1 | 9/2014 | Bammert et al. |
| 2015/0004161 A1 | 1/2015 | Zhu et al. |
| 2015/0037331 A1 | 2/2015 | Siadak et al. |
| 2015/0368336 A1 | 12/2015 | Siadak et al. |
| 2016/0024201 A1 | 1/2016 | Leung et al. |
| 2016/0137739 A1 | 5/2016 | Arnett et al. |
| 2016/0272703 A1 | 9/2016 | Hsieh et al. |
| 2016/0333101 A1 | 11/2016 | Zhou et al. |
| 2017/0058027 A1 | 3/2017 | Wu et al. |
| 2017/0096484 A1 | 4/2017 | Leung et al. |
| 2017/0158671 A1 | 6/2017 | Zhu et al. |
| 2017/0306019 A1 | 10/2017 | Carriere et al. |
| 2018/0066050 A1 | 3/2018 | Yao et al. |
| 2018/0079817 A1 | 3/2018 | Kaneko et al. |
| 2018/0155418 A1 | 6/2018 | Sprecher et al. |
| 2018/0215805 A1 | 8/2018 | Hjerrild et al. |
| 2018/0244766 A1 | 8/2018 | Li et al. |
| 2019/0010242 A1 | 1/2019 | Eckelman et al. |
| 2019/0038743 A1 | 2/2019 | Siadak et al. |
| 2019/0040125 A1 | 2/2019 | Leung et al. |
| 2019/0119372 A1 | 4/2019 | Yao et al. |
| 2019/0144533 A1 | 5/2019 | Siadak et al. |
| 2019/0169285 A1 | 6/2019 | Li et al. |
| 2019/0284272 A1 | 9/2019 | Bammert et al. |
| 2019/0330366 A1 | 10/2019 | Eckelman et al. |
| 2019/0338020 A1 | 11/2019 | Sprecher et al. |
| 2019/0389944 A1 | 12/2019 | Bammert et al. |
| 2020/0048325 A1 | 2/2020 | Zhan et al. |
| 2020/0048627 A1 | 2/2020 | Igawa et al. |
| 2020/0062840 A1 | 2/2020 | Li et al. |
| 2020/0069773 A1 | 3/2020 | Xu et al. |
| 2020/0069814 A1 | 3/2020 | Zhao et al. |
| 2020/0102396 A1 | 4/2020 | Kaneko et al. |
| 2020/0181258 A1 | 6/2020 | Leger et al. |
| 2020/0190203 A1 | 6/2020 | Shih et al. |
| 2020/0216536 A1 | 7/2020 | Brondyk et al. |
| 2020/0276261 A1 | 9/2020 | Zhao et al. |
| 2020/0277348 A1 | 9/2020 | Kitten et al. |
| 2020/0345843 A1 | 11/2020 | Asrat et al. |
| 2020/0362035 A1 | 11/2020 | Brondyk et al. |
| 2021/0009678 A1 | 1/2021 | Hammerberg et al. |
| 2021/0047406 A1 | 2/2021 | Irving et al. |
| 2021/0079105 A1 | 3/2021 | Orengo et al. |
| 2021/0163587 A1 | 6/2021 | Li et al. |
| 2021/0169896 A1 | 6/2021 | Zhao et al. |
| 2021/0268103 A1 | 9/2021 | Brewer et al. |
| 2021/0308277 A1 | 10/2021 | Zhao et al. |
| 2021/0363270 A1 | 11/2021 | Park et al. |
| 2021/0388053 A1 | 12/2021 | Zhan et al. |
| 2021/0393790 A1 | 12/2021 | Zhao et al. |
| 2021/0395340 A1 | 12/2021 | Zhan et al. |
| 2022/0009994 A1 | 1/2022 | Brondyk et al. |
| 2022/0049002 A1 | 2/2022 | Li et al. |
| 2022/0064263 A1 | 3/2022 | Zhan et al. |

FOREIGN PATENT DOCUMENTS

| | | |
|---|---|---|
| CN | 1896229 A | 1/2007 |
| CN | 101291692 A | 10/2008 |
| CN | 103890009 A | 6/2014 |
| EP | 1270595 A1 | 1/2003 |
| EP | 1500329 A2 | 1/2005 |
| EP | 1827485 A2 | 9/2007 |
| EP | 2215124 A1 | 8/2010 |
| EP | 2301965 A1 | 3/2011 |
| EP | 2493925 A1 | 9/2012 |
| EP | 2611462 A2 | 7/2013 |
| EP | 2703486 A1 | 3/2014 |
| EP | 2705053 A1 | 3/2014 |
| EP | 2710040 A1 | 3/2014 |
| EP | 2734549 A1 | 5/2014 |
| EP | 2764026 A2 | 8/2014 |
| EP | 2842573 A1 | 3/2015 |
| EP | 2968454 A1 | 1/2016 |
| EP | 3219729 A1 | 9/2017 |
| EP | 3227342 A1 | 10/2017 |
| EP | 2829551 B1 | 12/2017 |
| EP | 2644698 B1 | 1/2018 |
| JP | 2014-529295 A | 11/2014 |
| JP | 6022563 B2 | 11/2016 |
| RU | 2444528 A | 6/2009 |
| RU | 2009/111884 A | 10/2010 |
| WO | 2003060080 A2 | 7/2003 |
| WO | 2006081573 A2 | 8/2006 |
| WO | 2006088855 A1 | 8/2006 |
| WO | 2006088955 A2 | 8/2006 |
| WO | 2006122079 A1 | 11/2006 |
| WO | 2007143231 A2 | 12/2007 |
| WO | 2008028192 A2 | 3/2008 |
| WO | 2008086505 A2 | 7/2008 |
| WO | 2009071696 A2 | 6/2009 |
| WO | 2010117448 A2 | 10/2010 |
| WO | 2007133816 A3 | 11/2010 |
| WO | 2011047262 A2 | 4/2011 |
| WO | 2011065935 A1 | 6/2011 |
| WO | 2011106528 A1 | 9/2011 |
| WO | 2013011407 A1 | 1/2013 |
| WO | 2014191391 A1 | 12/2014 |
| WO | 2014208645 A1 | 12/2014 |
| WO | 2015042596 A1 | 3/2015 |
| WO | 2015/067755 A2 | 5/2015 |
| WO | 2015086830 A1 | 6/2015 |
| WO | 2015151079 A2 | 10/2015 |
| WO | 2015173782 A1 | 11/2015 |
| WO | 2016170176 A1 | 10/2016 |
| WO | 2017025698 A1 | 2/2017 |
| WO | 2018/073185 A1 | 4/2018 |
| WO | 2018156180 A1 | 8/2018 |
| WO | 2018156367 A1 | 8/2018 |
| WO | 2019/118512 A2 | 6/2019 |
| WO | 2019/177697 A2 | 9/2019 |
| WO | 2020073345 A1 | 4/2020 |
| WO | 2020155017 A1 | 8/2020 |
| WO | 2020257998 A1 | 12/2020 |
| WO | 2020258893 A1 | 12/2020 |
| WO | 2021041972 A1 | 3/2021 |
| WO | 2021115240 A1 | 6/2021 |
| WO | 2021123092 A1 | 6/2021 |
| WO | 2021123094 A1 | 6/2021 |
| WO | 2021165417 A1 | 8/2021 |

(56) References Cited

FOREIGN PATENT DOCUMENTS

| | | |
|---|---|---|
| WO | 2021188631 A1 | 9/2021 |
| WO | 2021212081 A1 | 10/2021 |
| WO | 2021212638 A1 | 10/2021 |
| WO | 2021216810 A1 | 10/2021 |
| WO | 2021216899 A1 | 10/2021 |
| WO | 2022029447 A1 | 2/2022 |
| WO | 2022049614 A1 | 3/2022 |

OTHER PUBLICATIONS

Noli, Chiara, et al. "A double-blinded, randomized, methylprednisolone-controlled study on the efficacy of oclacitinib in the management of pruritus in cats with nonflea nonfood-induced hypersensitivity dermatitis" Veterinary Dermatology, vol. 30, pp. 440-e30, Apr. 2019.

Table of Antibodies—Excerpt from WO 2019-177697, cited in Opposition of EP 3219729 on Nov. 25, 2022 (2 pages).

"Amended Claims With Annotations", filed Jul. 16, 2020 in Opposition of EP 2734549 (156 pages).

Third Party Observations According to Art. 115 EPC, dated Apr. 14, 2015, filed in EP 2734549 (9 pages).

Reply to Opposition Proceedings in EP 3219729, dated Nov. 3, 2021 (218 pages).

Decision (Preliminary and Non-binding Opinion of the Opposition Division) and Summons to Attend Oral Proceedings, dated Feb. 28, 2022 in Opposition of EP 3219729 (18 pages).

Further Written Submissions of Opponent O2, filed Nov. 24, 2022 in Opposition of EP 3219729 (36 pages).

Further Written Submissions of Opponent O1, filed Nov. 25, 2022 in Opposition of EP 3219729 (22 pages).

Reply to the Summons to Attend Oral Proceedings, filed Nov. 25, 2022 in Opposition of EP 3219729 (19 pages).

Olivry et al., "The ACVD Task Force on Canine Atopic Dermatitis: Forewords and Lexicon," Veterinary Immunology and Immunpathology, 2001, 81(3-4):143-146.

Olivry et al., "Toward a Canine Model of Atopic Dermatitis: Amplification of Cytokine-Gene Transcripts in the Skin of Atopic Dogs," Exp Dermatol, 1999, 8(3):204-211.

Olivry et al., "Treatment of Canine Atopic Dermatitis: 2010 Clinical Practice Guidelines from the International Task Force on Canine Atopic Dermatitis," Vet Dermatol, 2010, 21(3):233-248.

Pedersen et al., "Identification of Monoclonal Antibodies that Cross-React with Cytokines from Different Animal Species," Vet Immunol and Immunopath, 2002, 88:111-122.

Perrigoue et al., "IL-31-IL-31R Interactions Limit the Magnitude of Th2 Cytokine-Dependent Immunity and Inflammation Following Intestinal Helminth Infection," J Immunol, 2009, 182(10):6088-6094.

Picco et al., "A Prospective Study on Canine Atopic Dermatitis and Food-Induced Allergic Dermatitis in Switzerland," Vet. Dermatol, 2008, 19(3):150-155.

Prelaud et al., "Reevaluation of Diagnostic Criteria of Canine Atopic Dermatitis," Revue de Medecine Veterinaire, 1998, 149:1057-1064, English abstract only.

Pucheu-Haston et al., "A Canine Model of Cutaneous Late-Phase Reactions: Prednisolone Inhibition of Cellular and Cytokine Responses," Immunology, 2005, 117:177-187.

Raap et al., "Correlation of IL-31 Serum Levels with Severity of Atopic Dermatitis," J Allergy Clin Immunol, 2008, 122(2):421-423.

Raap et al., "Increased Levels of Serum IL-31 in Chronic Spontaneous Urticaria," Exp. Dermatol., 2010, 19(5):464-466.

Rawlings et al., "The JAK/STAT Signaling Pathway," J Cell Science, 2004, 117:1281-1283.

Reichmann et al., "Reshaping Human Antibodies for Therapy," Nature, 1988, 332:323-327.

Rudikoff et al., "Single Amino Acid Substitution Altering Antigen-Binding Specificity," 1982, PNAS, 79:1979-1983.

Saeki et al., "Thymus and Activation Regulated Chemokine (TARC)/CCL17 and Skin Diseases," J Derma Science, 2006, 43:75-84.

Saleem, et al., "Interleukin-31 Pathway and Its Role in Atopic Dermatitis: A Systematic Review," J Dermatolg Treat., 2017, 28(7):591-599.

Sandilands et al., "Filaggrin in the Frontline: Role in Skin Barrier Function and Disease," J Cell Science, 2009, 122:1285-1294.

Santoro, et al., "Canine and Human Atopic Dermatitis: Two Faces of the Same Host-Microbe Interaction," J Investigative Dermatol, 2016, 136:1087-1089.

Scheerlinck et al., "Functional and Structural Comparison of Cytokines in Different Species," Vet Immunol Immunopathol, 1999, 72(1-2):39-44.

Schlotter et al., "Lesional Skin in Atopic Dogs Shows a Mixed Type-1 and Type-2 Immune Responsiveness," Vet Immunol Immunopathol, 2011, 143(1-2):20-26.

Scott et al., "Treatment of Canine Atopic Dermatitis with a Commercial Homeopathic Remedy: A Single-Blinded, Placebo-Controlled Study," Can Vet J, 2002, 43(8):601-603.

Song et al., "JAK1 Activates STAT3 Activity in Non-Small-Cell Lung Cancer and IL-6 Neutralizing Antibodies Can Suppress JAK1-STAT3 Signaling," Mol Cancer Ther, 2011, 10(3):481-494.

Sonkoly et al., "IL-31: A New Link Between T Cells and Pruritus in Atopic Skin Inflammation," J Allergy Clin Immunol, 2006, 117(2):411-417.

Soumelis et al., "Human Epithelial Cells Trigger Dendritic Cell-Mediated Allergic Inflammation by Producing TSLP," Nat Immunol, 2002, 3(7):673-680.

Sousa et al., "The ACVD Task Force on Canine Atopic Dermatitis (II): Genetic Factors," Veterinary Immunology and Immunopathology, 2001, 81(3-4):153-157.

Strachan et al., "Family Size, Infection, and Atopy: The First Decade of the 'Hygiene Hypothesis," Thorax, 2000, 55(Suppl 1):S2-S10.

Takaoka et al., "Expression of IL-31 Gene Transcripts in NC/Nga Mice with Atopic Dermatitis," European Journal of Pharmacology, 2005, 516(2):180-181.

Takaoka et al., "Involvement of IL-31 on Scratching Behavior in NC/Nga Mice with Atopic-Like Dermatitis," Experimental Dermatology, 2006, 15(3):161-167.

Tang, "Molecular Cloning of Canine IL-13 Receptor a Chain ($\alpha$1 and $\alpha$2) cDNAs and Detection of Corresponding mRNAs in Canine Tissues," Veterinary Immunology and Immunopathology, 2001, 79(3-4):181-195.

Terada et al., "Clinical Comparison of Human and Canine Atopic Dermatitis Using Human Diagnostic Criteria: Proposal of Provisional Diagnostic Criteria for Canine Atopic Dermatitis," Journal of Dermatology, 2011, 38:784-790.

Tominaga et al., "In Vitro Model for Penetration of Sensory Nerve Fibers on a Matrigel Basement Membrane: Implication for Possible Application to Intractable Pruritus," British Journal of Dermatology, 2009, 161:1028-1037.

UniProt Database, IL31Ra, *Canis lupus familiaris* (Dog), UniProtKB—F1PTZ6, last modified May 8, 2019, 7 pages.

UniProt Database, Interleukin 31, *Canis lupus familiaris* (Dog), UniProtKB—C7G0W1, last modified Mar. 18, 2018, 4 pages.

UniProt Database, OSMR, *Canis lupus familiaris* (Dog), UniProtKB—E2QWS7, last modified Jun. 5, 2019, 8 pages.

Venereau et al., "Definition and Characterization of an Inhibitor for Interleukin-31," Journal of Biological Chemistry, 2010, 285(20):14955-14963.

Wai et al., "Interleukin-31 Induces Cytokine and Chemokine Production from Human Bronchial Epithelial Cells Through Activation of Mitogen-Activated Protein Kinase Signalling Pathways: Implications for the Allergic Response," Immunology, 2007, 122:532-541.

Winthrop, "The Emerging Safety Profile of JAK Inhibitors in Rheumatic Disease," Nat Rev Rheumatol, 2017, 13(4):234-243, and correction (1 page).

Wood et al., "Despite Identifying Some Shared Gene Associations with Human Atopic Dermatitis the use of Multiple Dog Breeds from Various Locations Limits Detection of Gene Associations in Canine Atopic Dermatitis," Vet Immunol and Immunopath, 2010, 138:193-197.

(56) References Cited

OTHER PUBLICATIONS

Wood et al., "Gene Expression in Canine Atopic Dermatitis and Correlation with Clinical Severity Scores," J Dermatol Sci, 2009, 55(1):27-33.
Wood et al., "Reference Genes for Canine Skin When Using Quantitative Real-Time PCR," Vet Immunol Immunopathol, 2008, 126(3-4):392-395.
Xia et al., "Interleukin 31 and Atopic Dermatitis," Intl Journal of Immunol, 2008, 31(5):383-386.
Yagi et al., "Interleukin-31 Stimulates Production of Inflammatory Mediators from Human Colonic Subepithelial Myofibroblasts," Int J Mol Med, 2007, 19(6):941-946.
Yasukawa et al., "Low-Dose Recombinant Canine Interferon-γ for Treatment of Canine Atopic Dermatitis: An Open Randomized Comparative Trial of Two Doses," Vet Dermatol, 2010, 21(1):42-49.
Zhang et al., "Structures and Biological Functions of IL-31 and IL-31 Receptors," Cytokine Growth Factor Rev., 2008, 19(5-6):347-356, NIH public access version, 18 pages.
IL-31 Antibody: (Aviva Systems Biology) Publication date [retrieved on Apr. 24, 2018, https://www.google.com/search?q=IL31+Antibody+-+N-terminal+region+%28OAAB05980%29+from+Aviva+Systems+Biology&rlz=1C1GGRV_enUS769US769&source=lnt&tbs=cdr%3A1%2Ccd_min%3A%2Ccd_max%3A2.24.2017&tbm=], 1 page.
Information from European Patent Office regarding revocation of EP Patent No. 3219729 (EP Application No. 17168574.6), issued Jan. 25, 2023 (1 page).
Brief Communication from European Patent Office regarding Opposition of EP Patent No. 3219729 (EP Application No. 17168574.6) enclosing letter from Opponent, dated Jan. 17, 2023 (3 pages).
Akira, Shizuo, "Functional Roles of STAT Family Proteins: Lessons from Knockout Mice," Stem Cells, (1999), vol. 17:138-146.
Bergeron et al., "Comparative functional characterization of canine IgG subclasses," Veterinary Immunology and Immunopathology, (2014), vol. 157, No. 1: 31-41.
Butler et al., "Porcine IgG: structure, genetics, and evolution," Immunogenetics, (2009), Springer, Berlin, DE, vol. 61, No. 3: 209-230.
Carter, Paul J., "Potent antibody therapeutics by design," Nature Reviews Immunology, (2006), Nature Pub. Group, GB, vol. 6: 343-357.
Colman, P.M., "Effects of amino acid sequence changes on antibody-antigen interactions," Res Immunol., (1994), vol. 145, No. 1: 33-36.
De Bellis, Filippo, "Latest Thinking on Atopic Dermatitis in Cats and Dogs," Apr. 7, 2014, Vet Times, 23 pages.
"Experimental Report of IL-31-Induced Stati-6 Phosphorylation," Filed in the European Patent Office Opposition to European Patent EP 2734549 B1, Jul. 18, 2019, 3 pages.
Favrot, C. "Feline allergic dermatitis: clinical aspects and diagnosis," (2013), ESVD-ECVD Annual Meeting, 5 pages.
Finkelstein et al., "Protein Physics," Institute of Protein Research, (2016), Second, Updated and Extended Edition, Lecture 1, p. 11.
GenBank NCBI Sequence XM_011287838.1, "Predicted: Felis catus interleukin 31 (IL31), mRNA," Feb. 10, 2015, 1 page.
Gibbs et al., "Role of the Pruritic Cytokine IL-31 in Autoimmune Skin Diseases," Frontiers in Immunololgy, (2019), vol. 10, Article 1383: 1-6.
Grimstad et al., "The Effect of Anti-Interleukin-31-Antibodies on Scratching Behaviour and Development of Dermatitis on NC/NGA Mice," Inflamm. Res., (2007), Supplement 3, FC09.7, S396-S397.
Halliwell, R. E. W., "The immunopathogenesis of allergic skin diseases in dogs and cats," EJCAP, (2009), vol. 19, No. 3: 213-218.
Hill et al., "Survey of the prevalence, diagnosis and treatment of dermatological conditions in small animals in general practice," Veterinary Record, (2006), vol. 158: 533-539.
Hobi et al., "Clinical characteristics and causes of pruritus in cats: a multicentre study on feline hypersensitivity-associated dermatoses," Vet. Dermatol., (2011), 1-8.
IL-31 Sequence Alignments, Filed in the European Patent Office Opposition to European Patent EP 3219729, Jun. 9, 2021, 2 pages.

International Preliminary Report on Patentability and Written Opinion for PCT/US2020/048618, dated Mar. 1, 2022, 7 pages.
International Search Report and Written Opinion for PCT/US2020/048618, dated Jan. 21, 2021, 11 pages.
International Search Report and Written Opinion received in PCT/US2021/028548, dated Sep. 2, 2021, 8 pages.
Jarilin, "Osnovy immunologii", M. Medicina: pp. 172-174, with Machine Translation.
Lai et al., "Interleukin-31 expression and relation to disease severity in human asthma," Scientific Reports, (2016), vol. 6: 22835, 1-9.
Lewis et al., "The different effector function capabilities of the seven equine IgG subclasses have implications for vaccine strategies," Molecular Immunology, (2008), vol. 45, No. 3: 818-827.
Maeda et al., "Engineering of Functional Chimeric Protein G-Vargula Luciferase," Analytical Biochemistry, (1997), vol. 249: 147-152.
Menotti-Raymond et al., "Mutation in CEP290 Discovered for Cat Model of Human Retinal Degeneration," Journal of Heredity, (2007), vol. 98, No. 3: 211-220.
Nagaoka et al., "Single amino acid substitution in the mouse IgG1 Fc region induces drastic enhancement of the affinity to protein A," Protein Engineering, (2003), vol. 16, No. 4: 243-245.
Pontius et al., "Initial sequence and comparative analysis of the cat genome," Genome Research, (2007), vol. 17: 1675-1689.
Product Sheet, DH82, CRL-10389(TM), ATCC, 2021, 7 pages.
Prost, C., "Feline atopic dermatitis: Clinical signs and diagnosis," EJCAP, (2009), vol. 19, No. 3: 223-229.
Robinson et al., "Clinical Consequences of Targeting IL-17 and TH17 in Autoimmune and Allergic Disorders," Curr Allergy Asthma Rep, (2013), vol. 13, No. 6: 1-14.
Roosje et al., "Feline Atopic Dermatitis: A Model for Langerhans Cell Participation in Disease Pathogenesis," American Journal of Pathology, (1997), vol. 151, No. 4: 927-932.
Roosje et al., "Increased Numbers of CD4+ and CD8+ T Cells in Lesional Skin of Cats with Allergic Dermatitis," Vet Pathol, (1998), vol. 35: 268-273.
Safdari et al., "Antibody humanization methods—a review and update," Biotechnology and Genetic Engineering Reviews, (2013), vol. 29, No. 2: 175-186.
Schlothauer et al., "Novel human IgG1 and IgG4 Fc-engineered antibodies with completely abolished immune effector functions," Protein Engineering, Design and Selection, (2016), vol. 29, No. 10: 457-466.
Schwartzman et al., "Canine Reaginic Antibody: Characterization of the Spontaneous Anti-Ragweed and Induced Anti-Dinitrophenyl Reaginic Antibodies of the Atopic Dog," Clin. exp. Immunol., (1971), vol. 9: 549-569.
Shen et al., "Single Variable Domain-IgG Fusion: A Novel Recombinant Approach to Fc Domain-Containing Bispecific Antibodies," The Journal of Biological Chemistry, (2006), vol. 281, No. 16: 10706-10714.
Strietzel et al., "In Vitro functional characterization of feline IgGs," Veterinary Immunology and Immunopathology, (2014), vol. 158, No. 3: 214-223.
Strohl, W. R., "Fusion Proteins for Half-Life Extension of Biologics as a Strategy to Make Biobetters," Biodrugs, (2015), vol. 29, No. 4: 215-239.
Torres et al., "The immunoglobulin constant region contributes to affinity and specificity," Trends in Immunology, (2008), vol. 29, No. 2: 91-97.
Yaseen et al., "Interleukin-31 promotes pathogenic mechanisms underlying skin and lung fibrosis in sclerodema," Rheumatololgy, (2020), vol. 0: 1-12.
Zoetis Press Release, Zoetis Receives European Commission Marketing Authorization for Cytopoint (lokivetmab), Apr. 26, 2017, 4 pages.
Zoetis Press Release, "Zoetis Receives USDA License for CYTOPOINT," Dec. 21, 2016, 4 pages.
Gutzwiller, M. E. R., "Canine Dendritic Cells and Their Involvement in Atopic Dermatitis," Dissertation, Bern, (2010), 69 pages.
Bieber et al., "Pathogenesis of Atopic Dermatitis: New Developments," Allergic Dermatosis and Urticaria, (2009), vol. 9: 291-294.

(56) References Cited

OTHER PUBLICATIONS

Gutzmer et al., "Pathogenetic and therapeutic implications of the histamine H4 receptor in inflammatory skin diseases and pruritus," Frontiers in Bioscience S3, (2011), pp. 985-994.
Incorvaia et al., "Allergy and the skin," Clinical and Experimental Immunology, (2008), vol. 153, Suppl. 1: 27-29.
Marsella et al., "Current evidence of skin barrier dysfunction in human and canine atopic dermatitis," Veterinary Dermatology, (2011), vol. 22, 239-248.
Suter et al., "The keratinocyte in epidermal renewal and defence," Veterinary Dermatology, (2009), vol. 20, 515-532.
Boguniewicz et al., "Atopic Dermatitis: A Disease of Altered Skin Barrier and Immune Dysregulation," Immunol Rev., (2011), vol. 242, No. 1: 233-246.
Hill, R. E., "Center for Veterinary Biologics Notice No. 13-05," United States Department of Agriculture, Animal and Plant Health Inspection Service, Veterinary Services, Center for Veterinary Biologics, Ames, Iowa, dated Mar. 4, 2013.
Hirano et al., "Signaling Mechanisms Through gp130: A Model of the Cytokine System," Cytokme & Growth Factor Reviews, (1997), vol. 8., No. 4: 241-252.
"INTERDOG: Canine Interferon-γ Preparation (Genetically Modified)," Toray Group, accessed at https://www.toray.com/products/chemicals/che_0060.html, on Aug. 27, 2019, 2 pages.
Medina-Cucurella et al., "Feline Interleukin-31 Shares Overlapping Epitopes with the Oncostatin M Receptor and IL-31RA," Biochemistry, (2020), vol. 59: 2171-2181, and S1-S10.
Schultz et al., "A common haplotype of the IL-31 gene influencing gene expression is associated with nonatopic eczema," J Allergy Clin Immunol, (2007), vol. 120, No. 5: 1097-1102.
Sequence Alignment performed Jul. 2, 2019, 3 pages.
"STAT3," Wikipedia, from Sep. 3, 2010, using the Internet archive service "Wayback Machine," 1 page.
UniProtKB—A0A3Q7TBT9 (A0A3Q7TBT9_VULVU), "Interleukin-31," last modified Jun. 5, 2019, 3 pages.
Weber et al., "Assessment of mRNA and microRNA Stabilization in Peripheral Human Blood for Multicenter Studies and Biobanks," Biomarker Insights, (2010), vol. 5: 95-102.
Wisselink et al., "The efficacy of cyclosporine A in cats with presumed atopic dermatitis: A double blind, randomised prednisolone-controlled study," The Veterinary Journal, (2009), vol. 180: 55-59.
Bammert et al., "Genome-Wide Expression Patterns in *Saccharomyces cerevisiae*: Comparison of Drug Treatments and Genetic Alterations Affecting Biosynthesis of Ergosterol," Antimicrobial Agents and Chemotherapy, (2000), vol. 44, No. 5: 1255-1265.
Dreuw et al., "Characterization of the Signaling Capacities of the Novel gp130-like Cytokine Receptor," The Journal of Biological Chemistry, (2004), vol. 279, No. 34, Issue of Aug. 20: 36112-36120.
Heise et al., "IL-31 Receptor Alpha Expression in Epidermal Keratinocytes Is Modulated by Cell Differentiation and Interferon Gamma," Journal of Investigative Dermatology, (2009) vol. 129, 240-243.
File History of U.S. Appl. No. 17/638,372, filed Feb. 25, 2022.
Statement of grounds of appeal, EP Opposition EP12748547.2-EP 2734549, dated Feb. 28, 2020, 39 pages.
Reply to appeal, EP Opposition EP12748547.2-EP 2734549, dated Jul. 16, 2020, 58 pages.
Preliminary Opinion Board of Appeal, EP Opposition EP12748547.2-EP 2734549, dated Feb. 23, 2020, 12 pages.
Minutes of the oral proceedings, EP Opposition EP12748547.2-EP 2734549, dated Mar. 31, 2022, 4 pages.
Decision of the Board of Appeal, EP Opposition EP12748547.2-EP 2734549, dated Apr. 1, 2022, 8 pages.
Notice of Appeal, EP Opposition EP12748547.2-EP 2734549, dated Dec. 19, 2019, 3 pages.
Notice of Opposition 1, EP Opposition EP17168574.6-EP 3219729, dated Jun. 9, 2021, 43 pages.
Notice of Opposition 2, EP Opposition EP17168574.6-EP 3219729, dated Jun. 9, 2021, 26 pages.
Reply to Opposition, EP Opposition EP17168574.6-EP 3219729, dated Nov. 3, 2021, 66 pages.
Third Party Observations, EP Opposition EP 19196963.3-EP 3653645, dated Aug. 22, 2022, 12 pages.
Notice of Opposition 1, EP Opposition EP12748547.2-EP 2734549, dated Feb. 21, 2018, 41 pages.
Notice of Opposition 2, EP Opposition EP12748547.2-EP 2734549, dated Feb. 23, 2018, 24 pages.
Reply to Opposition, EP Opposition EP12748547.2-EP 2734549, dated Jul. 23, 2018, 47 pages.
Rejection of the Opposition, EP Opposition EP12748547.2-EP 2734549, dated Oct. 21, 2019, 25 pages.
Bachmann et al., "Vaccination against IL-31 for the treatment of atopic dermatitis in dogs," Letters to the Editor, J Allergy Clin Immunol, (2018), vol. 142, No. 1: 279-281.e1, 4 pages.
Barber et al., "GAPDH as a housekeeping gene: analysis of GAPDH mRNA expression in a panel of 72 human tissues," Physiol Genomics, (2005), vol. 21: 389-395.
Declaration of Prof. Dr. Ralf Mueller (First), EP 2734549-12748547, dated Jul. 21, 2018, 16 pages.
Declaration of Prof. Dr. Ralf Mueller (Second), EP 2734549-12748547, dated Aug. 22, 2019, 6 pages.
Declaration of Gary F. Bammert, EP 2734549, EP 12748547, dated Aug. 28, 2019, 6 pages.
Canidae family information submitted in EP 2734549-12748547, dated Jul. 18, 2019, 2 pages.
Data and sequence alignments submitted in EP 2734549-12748547, dated Jul. 18, 2019, 9 pages.
Data submitted in EP 2734549-12748547, dated Jul. 18, 2019, 2 pages.
Experimental report submitted in EP 2734549-12748547, dated Jul. 18, 2019, 3 pages.
Declaration of Prof. Kun-Liang Guan, Ph.D., submitted in Opposition to EP 2734549, dated Jun. 23, 2019, 40 pages.
Declaration of Assistant Prof. Adam Rudinsky, DVM, MS, DACVIM, submitted in Opposition to EP 2734549, dated Jul. 16, 2019, 12 pages.
Declaration of Dr. Anthony Yu, BSc, DVM, MS, ADCD, submitted in Opposition to EP 2734549, dated Jul. 15, 2019, 20 pages.
IL-31 sequence alignments, submitted in Opposition in EP 3219729, (submitted on Jun. 9, 2021), 1 page.
Post-published data from Zoetis for two anti-feline IL-31 antibodies (extracted from WO 2019/177697), submitted in Opposition in EP 3219729, (submitted on Mar. 11, 2011), 4 pages.
EMBOSS Needle alignment, submitted in Opposition in EP 3219729, (Nov. 2, 2021), 1 page.
EMBOSS Needle alignment canine IL31—mouse IL-31, submitted in Opposition in EP 3219729, (Nov. 2, 2021), 1 page.
EMBOSS Needle alignment feline IL31—human IL-31, submitted in Opposition in EP 3219729, (Nov. 2, 2021), 1 page.
EMBOSS Needle alignment feline IL31—mouse IL-31, submitted in Opposition in EP 3219729, (Nov. 2, 2021), 1 page.
Harrison et al., "The use of quantitative RT-PCR to measure mRNA expression in a rat model of focal ischemia—caspase-3 as a case study," Molecular Brain Research, (2000), vol. 75: 143-149.
Kruse et al., "Transcriptome and proteome responses in RNAlater preserved tissue of *Arabidopsis thaliana*," PLoS ONE, (2017), vol. 12, No. 4: e0175943, 10 pages.
Liu et al., "A SYBR Green I real-time RT-PCR assay for detection and differentiation of influenza A(H1N1) virus in swine populations," Journal of Virological Methods, (2009), vol. 162: 184-187.
Olivry et al., "Early Activation of Th2/Th22 Inflammatory and Pruritogenic Pathways in Acute Canine Atopic Dermatitis Skin Lesions," Journal of Investigative Dermatology, (2016), vol. 136: 1961-1969.
Passow et al., "Nonrandom RNAseq gene expression associated with RNAlater and flash freezing storage methods," Mol Ecol Resour., (2019), vol. 19(2): 456-464.
Plager et al., "Gene transcription abnormalities in canine atopic dermatitis and related human eosinophilic allergic diseases," Vet Immunol Immunopathol., (2012), vol. 149(0): 136-142.

(56) References Cited

OTHER PUBLICATIONS

Radstrom et al., "Pre-PCR Processing: Strategies to Generate PCR-Compatible Samples," Molecular Biotechnology, (2004), vol. 26: 133-146.
Rugg et al., "Immunohistochemical Evaluation of IL-31 Receptor A Localization in Neuronal and Cutaneous Tissues of Beagle Dogs," Zoetis Inc.,Florham Park, NJ, USA.
Tomasco et al., "Comparison of commercial DNA preparation kits for the detection of Brucellae in tissue using quantitative real-time PCR," BMC Infectious Diseases, (2010), vol. 10: 100, 5 pages.
Tricarico et al., "Quantitative real-time reverse transcription polymerase chain reaction: normalization to rRNA or single housekeeping genes is inappropriate for human tissue biopsies," Analytical Biochemistry, (2002), vol. 309: 293-300.
Vandesompele et al., "Accurate normalization of real-time quantitative RT-PCR data by geometric averaging of multiple internal control genes," Genome Biology, (2002), vol. 3(7): research0034.1-0034.11.
Ip et al., "Interleukin-31 induces cytokine and chemokine production from human bronchial epithelial cells through activation of mitogen-activated protein kinase signalling pathways: implications for the allergic response," Immunology, (2007), vol. 122: 532-541.
Declaration of Gary F. Bammert (Second), EP 2734549, EP 12748547, dated Jul. 14, 2020, 3 pages.
Experimental Report of IL-31-Induced Stat1-6 Phosphorylation, extracted from WO 2019177697, submitted in EP 2734549 Opposition, Mar. 11, 2011, 3 pages.
Marsella et al., "Atopic Dermatitis in Animals and People: An Update and Comparative Review," Vet. Sci., (2017), vol. 4: 37, 19 pages.
Sapunar et al., "Dorsal root ganglion—a potential new therapeutic target for neuropathic pain," Journal of Pain Research, (2012), vol. 5: 31-38.
"IL-31 Antibody" (Aviva Systems Biology) Oct. 11, 2016, [retrieved on Apr. 24, 2018, https://www.avivasysbio.com/en/il31-antibody-n-temninal-region-oaab05980.html], 2 pages.
Aaronson et al., "A Road Map for Those Who Don't Know JAK-STAT," Science, 2002, 296:1653-1655.
Abdi, et al., "IL-31 Is an Inflammatory Pro-Fibrotic Factor Elevated in a Subset of Scleroderma Patients with Severe Pruritus," Abstract No. 821, Arthritis Rheumatol, 2016 68(suppl 10), 2 pages.
Advancing the Science of Atopic Dermatitis Treatment, Canine Atopic Dermatitis Immunotherapeutic Brochure, Zoetis, 2016, 8 pages.
AlphaScreen kits brochure, Perkins Elmer, Mar. 2011, 2 pages.
Bando et al., "Complete Overlap of Interleukin-31 Receptor A and Oncostatin M Receptor β in the Adult Dorsal Root Ganglia with Distinct Developmental Expression Patterns," Neuroscience, 2006, 142(4): 1263-1271.
Bilsborough et al., "IL-31 is Associated with Cutaneous Lymphocyte Antigen-Positive Skin Homing T Cells in Patients with Atopic Dermatitis," J Allergy and Clin Immunol, 2006, 117(2):418-425.
Bilsborough et al., "IL-31 Receptor (IL-31RA) Knockout Mice Exhibit Elevated Responsiveness to Oncostatin M," J Immunol, 2010, 185:6023-6030.
Bogiatzi et al., "Cutting Edge: Proinflammatory and Th2 Cytokines Synergize to Induce Thymic Stromal Lymphopoietin Production by Human Skin Keratinocytes," J Immunol, 2007, 178:3373-3377.
Brandt et al., "Th2 Cytokines and Atopic Dermatitis," J Clin Cell Immunol., 2011, 2(3):110, 25 pages.
Buddenkotte et al., "Pathophysiology and Therapy of Pruritus in Allergic and Atopic Diseases," Allergy, 2010, 65:805-821.
Canine Atopic Dermatitis Immunotherapeutic, First to Know Slides, 2015, found at http://o.zoetisus.com/rs/686-BYD-443/images/canine-il-31-first-to-know-slide-deck.pdf, 160 pages.
Canine Atopic Dermatitis Immunotherapeutic: A Caninized Anti-cIL-31 Monoclonal Antibody, FAQ's, o.zoetisus.com/rs/686-BYD-443/images/canine-il-31-faqs.pdf, 16 pages.
Carmi-Levy, et al., "A Modular View of Cytokine Networks in Atopic Dermatitis," Clinic Rev Allerg Immunol, 2011, 41:245-253.
Carr et al., "Investigation of the Pruitogenic Effects of Histamine, Serotonin, Tryptase, Substance P and Interleukin-2 in Healthy Dogs," Vet Dermatol, 2009, 20(2):105-110.
Castellani et al., "IL-31 A TH2 Cytokine Involved in Immunity and Inflammation," Int J Immunopathol Pharmacol, 2010, 23(3):709-713.
Cevikbas et al., "Interleukin-31 Directly Regulates Neuronal Function in Inflammation and Itch," Journal Inv. Derm. Abstract No. 700, 2010, 130:S117, 2 pages.
Cevikbas et al., "A Sensory Neuron-Expressed IL-31 Receptor Mediates T helper Cell-Dependent Itch: Involvement of TRPV1 and TRPA1," J Allergy Clin Immunol, 2014, 133:448-60, 460.e1-e7.
Chattopadhyay et al., "Interleukin-31 and Oncostatin-M Mediate Distinct Signaling Reactions and Response Patterns in Lung Epithelial Cells," Journal of Biological Chemistry, 2007, 282(5):3014-3026.
Chen et al., "Restoration of Tight Junction Structure and Barrier Function by Down-Regulation of the Mitogen-Activated Protein Kinase Pathway in Ras-Transformed Madin-Darby Canine Kidney Cells," Mol Biol Cell, 2000, 11:849-862.
Cheung et al., "Activation of Human Eosinophils and Epidermal Keratinocytes by Th2 Cytokine IL-31: Implication for the Immunopathogenesis of Atopic Dermatitis," Int Immunol, 2010, 22(6):453-467.
Cornelissen et al., "Signaling by IL-31 and Functional Consequences," European Journal of Cell Biology, 2012, 91:552-566.
Cosgrove et al., "A Multicentre Clinical Trial to Evaluate the Efficacy and Field Safety of Oclacitinib," Abstract FC-35, Veterinary Dermatology, 2012, 23(Suppl. 1), 1 page.
Cytopoint, European Medicines Agency, European public assessment report (EPAR), 2017, 2 pages.
Cytopoint™ ALK Technical Memo, Apr. 2017, Medical Scientific Affairs, 2 pages.
Dambacher et al., "Interleukin 31 Mediates MAP Kinase and STAT1/3 Activation in Intestinal Epithelial Cells and its Expression is Upregulated in Inflammatory Bowel Disease," Gut, 2007, 56:1257-1265.
Darnell et al., "Jak-STAT Pathways and Transcriptional Activation in Response to IFNs and Other Extracellular Signaling Proteins," Science, 1994, 264(5164):1415-1421, 7 pages.
Dillon et al., "Interleukin 31, a Cytokine Produced by Activated T Cells, Induces Dermatitis in Mice," Nature Immunology, 2004, 5(7):752-760.
Diveu et al., "Predominant Expression of the Long Isoform of GP130-like (GPL) Receptor is Required for Interleukin-31 Signaling," Eur. Cytokine Netw., 2004, 15(4): 291-302.
Estep et al., "High Throughput Solution-Based Measurement of Antibody-Antigen Affinity and Epitope Binning," mAbs, 2013, 5(2):270-278.
Extended European Search Report for European Patent Application No. 18756690.6 dated Nov. 2, 2020, 9 pages.
Ezzat et al., "Serum Measurement of Interleukin-31 (IL-31) in Pediatric Atopic Dermatitis: Elevated Levels Correlate with Severity Scoring," JEADV, 2011, 25:334-339.
Felsburg, "Overview of Immune System Development in the Dog: Comparison with Humans," Hum Exp Toxicol, 2002, 21(9-10):487-92.
File History of U.S. Appl. No. 15/467,464, filed Mar. 23, 2017.
File History of U.S. Appl. No. 15/844,142, filed Dec. 15, 2017.
File History of U.S. Appl. No. 16/186,013, filed Nov. 9, 2018.
File History of U.S. Appl. No. 16/488,045, filed Aug. 22, 2019.
Fleck, et al., "Comparison of the Janus Kinase (JAK) Inhibitor, Oclacitinib, and Prednisolone in Canine Models of Pruritus," Abstract FC-36, Veterinary Dermatology, 2012, 23(Suppl. 1), 1 page.
Gonzales et al., "Interleukin-31: Its Role in Canine Pruritus and Naturally Occurring Canine Atopic Dermatitis," Vet Dermatol, 2013, 24:48-53 and e11-e12.
Gonzales et al., "Oclacitinib (APOQUEL®) is a novel Janus kinase inhibitor with activity against cytokines involved in allergy," Journal of Veterinary Pharmacology and Therapeutics, 2014, 37:317-24.
Gonzales et al., "Oclacitinib (Apoquel®; Zoetis) is a novel Janus kinase inhibitor that has activity against canine pro-allergic and pro-inflammatory cytokines," Abstracts of the 26th Annual Con-

(56) References Cited

OTHER PUBLICATIONS gress of the ECVD-ESVD, Sep. 19-21, 2013, Valencia, Spain, Veterinary Dermatology, 2013, 24:377-397, at pp. 384-385.

Gonzolas, et al., "IL-31: Its Role in Canine Pruritus and Prevalence in Naturally Occurring Canine Atopic Dermatitis," Abstract Supporting Original Study 5, Veterinary Dermatology, 2012, 23(Suppl. 1):6.

Grimstad et al., "Anti-Interleukin-31-Antibodies Ameliorate Scratching Behaviour in NC/Nga Mice: A Model of Atopic Dermatitis," Experimental Dermatology, 2009, 18(1):35-43.

Haitina et al., "The G Protein-Coupled Receptor Subset of the Dog Genome is More Similar to that in Humans than Rodents," BMC Genomics, 2009, 10:24, 13 pages.

Halliwell et al., "The ACVD task force on canine atopic dermatitis (III): the role of antibodies in canine atopic dermatitis," Veterinary Immunology and Immunpathology, 2001, 81(3-4):159-167.

Hashimoto et al., "Itch-Associated Scratching Contributes to the Development of Dermatitis and Hyperimmunoglobulinaemia E in NC/Nga Mice," Experimental Dermatology, 2011, 20:820-825.

Hashizume et al., "IL-6 Plays an Essential Role in Neutrophilia Under Inflammation," Cytokine, 2011, 54:92-99.

Hashizume et al., "The Roles of Interleukin-6 in the Pathogenesis of Rheumatoid Arthritis," Arthritis, 2011, Article ID 765624, 8 pages.

Hawro et al., "Interleukin-31 Does Not Induce Immediate Itch in Atopic Dermatitis Patients and Healthy Controls after Skin Challenge," Allergy, 2014, 69:113-117.

Hill et al., "Pilot Study of the Effect of Individualised Homeopathy on the Pruritus Associated with Atopic Dermatitis in Dogs," Vet. Rec., 2009, 164(12):364-70.

Hillier et al., "The ACVD Task Force on Canine Atopic Dermatitis (I): Incidence and Prevalence," Veterinary Immunology and Immunopathology, 2001, 81:147-151.

Holsapple et al., "Species Comparison of Anatomical and Functional Immune System Development," Birth Defects Res B Dev Reprod Toxicol., 2003, 68(4):321-34.

Hong et al., "Functional Regulation of Interleukin-31 Production by its Genetic Polymorphism in Patients with Extrinsic Atopic Dermatitis," Acta Derm Venereol, 2012, 92(4): 430-432.

Humphrey, et al., "Development of a Model of IL-31 Induced Pruritus in Beagle Dogs," Abstract FC-30, Veterinary Dermatology, 2012, 23(Suppl. 1), 1 page.

Hvid et al., "IL-25 in Atopic Dermatitis: A Possible Link Between Inflammation and Skin Barrier Dysfunction," J Invest Dermatol, 2011, 131(1):150-157.

ImmunoGlobe® product information, Antikörpertechnik GmbH, retrieved Feb. 8, 2018, 2 pages.

International Nonproprietary Names for Pharmaceutical Substances (INN) excerpt for Lokivetmab, WHO Drug Information, 2015, 29(3):407-408.

International Search Report and Written Opinion for PCT/US2018/017623, dated May 15, 2018, 15 pages.

International Search Report received in PCT/US2017/023788, dated Jun. 6, 2017, 12 pages.

Janeway et al., Immunology, 3rd ed., Garland Publications, 1997, pp. 3:1-3; 11.

Javens et al., "Oclacitinib Inhibits Canine IL-4 and IL-13-activated JAK-STAT Pathways in Canine DH82 Cells," 2018 31st Proceedings of the North American Veterinary Dermatology Forum, May 1-5, 2018, p. 104.

Jin et al., "Animal Models of Atopic Dermatitis," J Invest Dermatol, 2009, 129(1):31-40.

Kanda et al., "Characterization of Canine Filaggrin: Gene Structure and Protein Expression in Dog Skin," Vet Dermatol, 2013, 24:25-31, e7.

Kasraie et al, "Interleukin (IL)-31 Induces Pro-Inflammatory Cytokines in Human Monocytes and Macrophages Following Stimulation with Staphylococcal Exotoxins," Allergy, 2010, 65:712-721.

Kasraie et al., "Functional Effects of Interleukin 31 in Human Primary Keratinocytes," Allergy, 2011, 66:845-852.

Kasraie et al., "Interieukin (IL)-31 Activates Signal Transducer and Activator of Transcription (STAT)-1, STAT-5 and Extracellular Signal-Regulated Kinase 1/2 and Down-Regulates IL-12p40 Production in Activated Human Macrophages," Allergy, 2013, 68:739-747.

Kasutani et al., "Anti-IL-31 Receptor Antibody is Shown to be a Potential Therapeutic Option for Treating Itch and Dermatitis in Mice," British Journal of Pharmacology, 2014, 171:5049-5058.

Kindred Biosciences' (KIN) CEO Richard Chin on Q1 2017 Results—Earnings Call Transcript, 2017, 3 pages.

Kovalik et al., "The Use of Ciclosporin A in Veterinary Dermatology," Vet J, 2012, 193(2):317-25.

Le Saux et al., "Molecular Dissection of Human Interleukin-31-Mediated Signal Transduction through Site-Directed Mutagenesis," Journal of Biological Chemistry, 2010, 285(5):3470-3477.

Leung et al., "Atopic Dermatitis," Lancet, 2003, 361:151-60.

Leung, "Human Atopic Dermatitis: From Laboratory Research to Bedside," Scientific Session Presentations, 2010, found at http://ssms.weblinkconnect.com/CWT/EXTERNAL/WCPAGES_NAVDF/PDF/ARCHIVES/2010SCIENTIFIC.PDF; 60 pages.

Maeda et al., "Expression Analysis of CCL27 and CCL28 mRNA in Lesional and Non-Lesional Skin of Dogs with Atopic Dermatitis," J Vet. Med. Sci., 2008, 70(1):51-55.

Maeda et al., "Expression of CC Chemokine Receptor 4 (CCR4) mRNA in Canine Atopic Skin Lesion," Veterinary Immunology and Immunopathology, 2002, 90(3-4):145-154.

Maeda et al., "Lesional Expression of Thymus and Activation-Regulated Chemokine in Canine Atopic Dermatitis," Vet Immunol Immunopathol, 2002, 88(1-2):79-87.

Maeda S. et al., "Production of a Monoclonal Antibody to Canine Thymus and Activation-Regulated Chemokine (TARC) and Detection of TARC in Lesional Skin from Dogs with Atopic Dermatitis," Veterinary Immunology and Immunopathology, 2005, 103(1-2):83-92.

Marsella et al., "Animal Models of Atopic Dermatitis," Clinics in Dermatology, 2003, 21(2):122-133.

Marsella et al., "Canine Models of Atopic Dermatitis: A Useful Tool with Untapped Potential," Journal of Investigative Dermatology, 2009, 129:2351-2357.

Marsella et al., "Current Understanding of the Pathophysiologic Mechanisms of Canine Atopic Dermatitis," Journal of the American Veterinary Medical Association, 2012, 241:194-207.

Marsella et al., "Pilot Investigation of a Model for Canine Atopic Dermatitis: Environmental House Dust Mite Challenge of High-IgE-Producing Beagles, Mite Hypersensitive Dogs with Atopic Dermatitis and Normal Dogs," Veterinary Dermatology, 2006, 17:24-35.

Marsella et al., "Transmission Electron Microscopy Studies in an Experimental Model of Canine Atopic Dermatitis," Veterinary Dermatology, 2010, 21:81-88.

McCandless et al., "Allergen-Induced Production of IL-31 by Canine Th2 Cells and Identification of Immune, Skin, and Neuronal Target Cells," Veterinary Immunology and Immunopathy, 2014, 157:42-48.

McCandless et al., "Production of IL-31 by Canine Th2 Cells and Identification of Inflammatory and Neuronal Target Cells," Abstract FC-65, Veterinary Dermatology, 2012, 23(Suppl. 1), 1 page.

Meng, et al., "New mechanism underlying IL-31-induced atopic dermatitis," J Allergy Clin Immunol, 2018, 141:1677-89, 1689.e1-e8.

Merryman-Simpson et al., "Gene (mRNA) Expression in Canine Atopic Dermatitis: Microarray Analysis," Vet Dermatol, 2008, 19(2):59-66.

Metz et al., "Pruritus: an Overview of Current Concepts," Vet Dermatol, 2011, 22(2):121-31.

Michels et al., "A blinded, randomized, placebo-controlled, dose determination trial of lokivetmab (ZTS-00103289), a caninized, anti-canine IL-31 monoclonal antibody in client owned dogs with atopic dermatitis," Vet Dermatol, 2016, 27(6): 478-e129.

Mizuno et al., "Molecular Cloning of Canine Interleukin-31 and its Expression in Various Tissues," Veterinary Immunology and Immunopathology, 2009, 131:140-143.

(56) References Cited

OTHER PUBLICATIONS

Moyaert et al., "A Blinded, Randomized Clinical Trial Evaluating the Efficacy and Safety of Lokivetmab Compared to Ciclosporin in Client-Owned Dogs with Atopic Dermatitis," Vet Dermatol, 2017, 28(6):593-603 and e144-e145.

Nakamura et al., "Pruritogenic mediators in psoriasis vulgaris: comparative evaluation of itch-associated cutaneous factors," British J of Dermatol, 2003, 149:718-730.

National Human Genome Research Institute (NHGRI), "Researchers Publish Dog Genome Sequence," 2005, 2 pages.

Nattkemper et al., "Cutaneous T-cell Lymphoma and Pruritus: The Expression of IL-31 and its Receptors in the Skin," Acta Derm Venereol, 2016, 96:894-898.

Neis et al., "Enhanced Expression Levels of IL-31 Correlate with IL-4 and IL-13 in Atopic and Allergic Contact Dermatitis," J Allergy Clin Immunol, 2006, 118(4):930-937.

Niyonsaba et al., "Antimicrobial Peptides Human β-Defensins and Cathelicidin LL-37 Induce the Secretion of a Pruritogenic Cytokine IL-31 by Human Mast Cells," J Immunol, 2010, 184:3526-3534.

Nobbe et al., "IL-31 Expression by Inflammatory Cells is Preferentially Elevated in Atopic Dermatitis," Acta Derm Venereol, 2012, 92:24-28, comment on same at 92:5-6.

Nuttall et al., "Expression of Th1, Th2 and Immunosuppressive Cytokine Gene Transcripts in Canine Atopic Dermatitis," Clin Exp Allergy, 2002, 32(5):789-795.

Nuttall et al., "T-Helper 1, T-helper 2 and Immunosuppressive Cytokines in Canine Atopic Dermatitis," Veterinary Immunol Immunopathol, 2002, 87(3-4):379-384.

O'Kennedy et al., "A Review of Enzyme-Immunoassay and a Description of a Competitive Enzyme-Linked Immunosorbent Assay for the Detection of Immunoglobulin Concentrations," Biochemical Education, 1990, 18(3):136-140.

O'Shea et al., "A New Modality for Immunosuppression: Targeting the JAK/STAT Pathway," Nat Rev Drug Discov, 2004, 3(7):555-564.

Olivry et al., "Interventions for Atopic Dermatitis in Dogs: A Systematic Review of Randomized Controlled Trials," Vet Dermatol, 2010, 21:4-22.

Chinese Office Action with Search Report and English translation dated Jan. 20, 2023 in corresponding Chinese Patent Application No. 201880026436.4 (13 pages).

Michels et al., "A blinded, randomized, placebo-controlled trial of the safety of lokivetmab (ZTS-00103289), a caninized anti-canine IL-31 monoclonal antibody in client-owned dogs with atopic dermatitis," Vet Dermatol, vol. 27(6); pp. 505-e136 (Dec. 2016).

Jiao et al., "Progress in the study of the correlation between interleukin-31 and atopic dermatitis," China Medical Innovation, vol. 13 No. 36, pp. 133-136 (Dec. 25, 2016).

LC

```
M14   METDTLLLWVLLLWVPGSTGDIVLTQSPASLAVSLGQRATISCRAS          MHWY
M18   METDTLLLWVLLLWVPGSTGDIVLTQSPASLAVSPGQRATISCRAS          IHWY
M19   METDTLLLWVLLLWVPGSTGDIVLTQSPASLAVSLGQRATISCRAS          MHWY
M87   METDTLLLWVLLLWVPGSTGDIVLTQSPASLAVSLGQRATISCRAS          MHWN
      ****************************** ******* ***:**.* * *:;**

M14   QQKSGQSPKLLIY    NLESGIPARFGGSGSRTDFTLTIDPVEADDVATYY
M18   QQKPGQSPKLLIY    NLESGIPARFSGSGSRTDFTLTINPVETDDVATYY
M19   QQKPGQPPKLLIY    NLESGIPARFSGSGSRTDFTLTINPVEADDIATYY
M87   QQKPGQPPRLLIY    NLESGVPARFSGSGSQTDFTLNIHPVEEEDAATYY
      ***.**.*:****    *****:****.****.*****.*.***.;* *.*

M14        GGGTKLEIKRADAAPTVSIFPPSSEQLTSGGASVVCFLNNFYPKDINVKWKIDGSERQ
M18        GGGTKLEIKRADAAPTVSIFPPSSEQLTSGGASVVCFLNNFYPKDINVKWKIDGSERQ
M19        GGGTKLEIKRADAAPTVSIFPPSSEQLTSGGASVVCFLNNFYPKDINVKWKIDGSERQ
M87        GGGTKLEIKRADAAPTVSIFPPSSEQLTSGGASVVCFLNNFYPKDINVKWKIDGSERQ
           :***********************************************************

M14   NGVLNSWTDQDSKDSTYSMSSTLTLTKDEYERHNSYTCEATHKTSTSPIVKSFNRNEC  (SEQ ID NO: 36)
M18   NGVLNSWTDQDSKDSTYSMSSTLTLTKDEYERHNSYTCEATHKTSTSPIVKSFNRNEC  (SEQ ID NO: 37)
M19   NGVLNSWTDQDSKDSTYSMSSTLTLTKDEYERHNSYTCEATHKTSTSPIVKSFNRNEC  (SEQ ID NO: 38)
M87   NGVLNSWTDQDSKDSTYSMSSTLTLTKDEYERHNSYTCEATHKTSTSPIVKSFNRNEC  (SEQ ID NO: 39)
      **********************************************************
```

```
M14_HC   MAVLGLLLCLVTFPSCVLSEVQLQESGPSLVKPSQTLSLTCSVT        WNWIRKFP
M19_HC   MAVLGLLFCLVTFPSCVLSEVQLQESGPSLVKPSQTLSLTCSVT        WNWIRKFP
M18_HC   MAVLGLLFCLVTFPSCVLSEVQLQESGPSLVKPSQTLSLTCSVT        WNWIRKFP
M87_HC   MAVLGLLFCLVTFPSCVLSEVKLVESGGSLVQPGSSLRLSCATS        NNWVRQPP
         *******;*********** .*** .**:*. ;* *:*;.:* ::*. * **:*; *

M14_HC   GNKLEYMGY     ---TDYNPSLKSRISITRDTSKNQYYLQLNSVTEDTATYYC
M19_HC   GNKLEYMGY     ---TDYNPSLKSRISITRDTSKNQYYLQLNSVTEDTATYYC
M18_HC   GNKLEYMGY     ---TYYNPSLKSRISITRDTSKNQYYLQLNSVTEDTATYYC
M87_HC   GKKLEWIGR        TRYSASVKGRFTISRDNSQSILYLQMNTLRAEDSATYYC-
         *; ***;;*       .. * ..;*..*.;;**;*..**..;**;: ;:**;*******

M14_HC               WGQGTSVTVSSAKTTPPSVYPLAPGS  (SEQ ID NO: 40)
M19_HC               WGQGTSVTVSSAKTTPPSVYPLAPGS  (SEQ ID NO: 41)
M18_HC               WGQGTSVTVSSAKTTPPSVYPLAPGS  (SEQ ID NO: 42)
M87_HC               WGQGTTLTVSSAKTTPPSVYPLAPGS  (SEQ ID NO: 43)
                     .**  .:** ;***************
```

FIG 1B

FIG 7A  FIG 7B
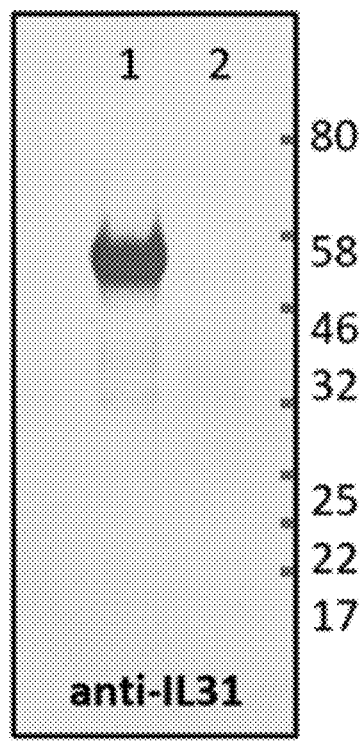 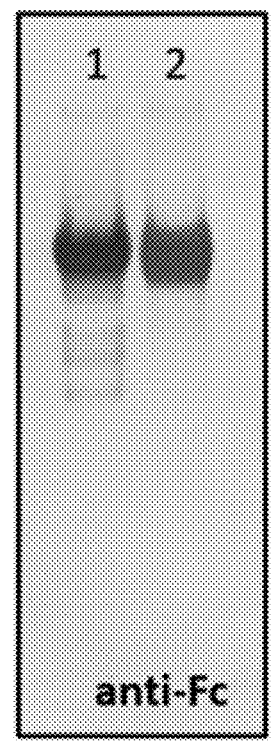
1. Feline IL31-huFc-His6
2. Horse IL31-huFc-His6

ANTI-IL31 ANTIBODIES FOR VETERINARY USE

This application is a divisional of U.S. application Ser. No. 16/186,013, filed Nov. 9, 2018, which is a divisional of U.S. application Ser. No. 15/844,142, filed Dec. 15, 2017, now U.S. Pat. No. 10,150,810, which is a divisional of Ser. No. 15/467,464, filed Mar. 23, 2017, now U.S. Pat. No. 10,093,731, which claims the benefit of U.S. Provisional Application No. 62/463,543, filed Feb. 24, 2017, each of which is incorporated by reference herein in its entirety for any purpose.

FIELD OF THE INVENTION

This invention relates to isolated anti-IL31 antibodies, for example, binding to canine IL31, and methods of using the same, for example, treating IL31-induced conditions or reducing IL31 signaling function in cells, for instance in companion animals, such as canines, felines, and equines.

BACKGROUND

Interleukin 31 (IL31) is a cytokine mostly produced by Th2 cells and understood to be involved in promoting skin disease, such as pruritic and other forms of allergic diseases (for example, atopic dermatitis). IL31 functions by binding its receptor and activating downstream activities, such as activation of JAK1, and is thought to cause many of the clinical problems associated with dermatitis and other disorders.

Companion animals such as cats, dogs, and horses, suffer from many skin diseases similar to human skin diseases, including atopic dermatitis. However, the IL31 sequence is divergent between human, cat, dog, and horse. There remains a need, therefore, for methods and compounds that can be used specifically to bind companion animal IL31 for treating IL31-induced conditions and for reducing IL31 signaling.

SUMMARY OF THE INVENTION

In some embodiments, an isolated antibody is provided that binds to canine IL31. In some embodiments the antibody binds to an epitope comprising amino acids 34-50 of SEQ ID NO: 22. In some embodiments, the antibody binds to an epitope comprising the amino acid sequence of SEQ ID NO: 23.

In some embodiments, the antibody binds to canine IL31 with a dissociation constant (Kd) of less than $5 \times 10^{-6}$ M, less than $1 \times 10^{-6}$ M, less than $5 \times 10^{-7}$ M, less than $1 \times 10^{-7}$ M, less than $5 \times 10^{-8}$ M, less than $1 \times 10^{-8}$ M, less than $5 \times 10^{-9}$ M, less than $1 \times 10^{-9}$ M, less than $5 \times 10^{-10}$ M, less than $1 \times 10^{-10}$ M, less than $5 \times 10^{-11}$ M, less than $1 \times 10^{-11}$ M, less than $5 \times 10^{-12}$ M, or less than $1 \times 10^{-12}$ M, as measured by biolayer interferometry.

In some embodiments, the antibody reduces IL31 signaling function in a companion animal species, as measured by a reduction in STAT-3 phosphorylation. In some embodiments, the companion animal species is canine, feline, or equine.

In some embodiments, the antibody binds to feline IL31 or equine IL31, as determined by immunoblot analysis or biolayer interferometry. In some embodiments, the antibody competes with monoclonal M14 antibody in binding to canine IL31. In some embodiments, the antibody of any one of claims 1-5, wherein the antibody competes with monoclonal M14 antibody in binding to feline IL31 or in binding to equine IL31.

In some embodiments, the antibody is a monoclonal antibody. In some embodiments, the antibody is a canine, a caninized, a feline, a felinized, an equine, an equinized, or a chimeric antibody. In some embodiments, the antibody is a chimeric antibody comprising murine variable heavy chain framework regions or murine variable light chain framework regions.

In some embodiments, the antibody comprises a heavy chain and a light chain, wherein:
a. the heavy chain comprises a CDR-H1 sequence having at least 85% sequence identity, at least 90% sequence identity, at least 95% sequence identity, or at least 98% sequence identity to the amino acid sequence of SEQ ID NO: 1; a CDR-H2 sequence having at least 85% sequence identity, at least 90% sequence identity, at least 95% sequence identity, or at least 98% sequence identity to the amino acid sequence of SEQ ID NO: 2; and a CDR-H3 sequence having at least 85% sequence identity, at least 90% sequence identity, at least 95% sequence identity, or at least 98% sequence identity to the amino acid sequence of SEQ ID NO: 3, and
b. the light chain comprises a CDR-L1 sequence having at least 85% sequence identity, at least 90% sequence identity, at least 95% sequence identity, or at least 98% sequence identity to the amino acid sequence of SEQ ID NO: 8; a CDR-L2 sequence having at least 85% sequence identity, at least 90% sequence identity, at least 95% sequence identity, or at least 98% sequence identity to the amino acid sequence of SEQ ID NO: 9; and a CDR-L3 sequence having at least 85% sequence identity, at least 90% sequence identity, at least 95% sequence identity, or at least 98% sequence identity to the amino acid sequence of SEQ ID NO: 10.

In some embodiments, the antibody comprises a heavy chain comprising (a) a CDR-H1 comprising the amino acid sequence of SEQ ID NO: 1, (b) a CDR-H2 comprising the amino acid sequence of SEQ ID NO: 2, and (c) a CDR-H3 comprising the amino acid sequence of SEQ ID NO: 3. In some embodiments, the antibody comprises a light chain comprising (a) a CDR-L1 comprising the amino acid sequence of SEQ ID NO: 8, (b) a CDR-L2 comprising the amino acid sequence of SEQ ID NO: 9, and (c) a CDR-L3 comprising the amino acid sequence of SEQ ID NO: 10.

In some embodiments, the antibody comprises one or more of (a) a variable region heavy chain framework 1 (HC-FR1) sequence of SEQ ID NO: 4, (b) a HC-FR2 sequence of SEQ ID NO: 5, (c) a HC-FR3 sequence of SEQ ID NO: 6, (d) a HC-FR4 sequence of SEQ ID NO: 7, (e) a variable region light chain framework 1 (LC-FR1) sequence of SEQ ID NO: 11, (f) an LC-FR2 sequence of SEQ ID NO: 12, (g) an LC-FR3 sequence of SEQ ID NO: 13, or (h) an LC-FR4 sequence of SEQ ID NO: 14.

In some embodiments, the antibody comprises:
a. (i) a variable light chain sequence having at least 85%, at least 90%, at least 95%, or at least 98% sequence identity to the amino acid sequence of SEQ ID NO: 24; (ii) a variable heavy chain sequence having at least 85%, at least 90%, at least 95%, or at least 98% sequence identity to the amino acid sequence of SEQ ID NO: 25; or (iii) a variable light chain sequence as in (i) and a variable heavy chain sequence as in (ii); or
b. (i) a variable light chain sequence having at least 85%, at least 90%, at least 95%, or at least 98% sequence identity to the amino acid sequence of SEQ ID NO: 16; (ii) a variable heavy chain sequence having at least 85%, at least 90%, at least 95%, or at least 98% sequence identity to the amino acid sequence of SEQ ID NO: 15; or (iii) a variable light chain sequence as in (i) and a variable heavy chain sequence as in (ii); or c. (i) a variable light chain sequence having at least 85%, at least 90%, at least 95%, or at least 98% sequence identity to the amino acid sequence of SEQ ID NO: 32; (ii) a variable heavy chain sequence having at least 85%, at least 90%, at least 95%, or at least 98% sequence identity to the amino acid sequence of SEQ ID NO: 33; or (iii) a variable light chain sequence as in (i) and a variable heavy chain sequence as in (ii).

In some embodiments, the antibody comprises a variable light chain sequence of SEQ ID NO: 24; SEQ ID NO: 16; or SEQ ID NO: 32. In some embodiments, the antibody comprises a variable heavy chain sequence SEQ ID NO: 25; SEQ ID NO: 15; or SEQ ID NO: 33. In some embodiments, the antibody comprises: a variable light chain sequence of SEQ ID NO: 24 and a variable heavy chain sequence of SEQ ID NO: 25; a variable light chain sequence of SEQ ID NO: 16 and a variable heavy chain sequence of SEQ ID NO: 15; or a variable light chain sequence of SEQ ID NO: 32 and a variable heavy chain sequence of SEQ ID NO: 33.

In some embodiments, the antibody is a chimeric antibody comprising a constant heavy chain region or constant light chain region derived from a companion animal.

In some embodiments, the antibody comprises (a) a canine heavy chain constant region selected from an IgG-A, IgG-B, IgG-C, and IgG-D constant region; (b) a feline heavy chain constant region selected from an IgG1, IgG2a, and IgG2b constant region; or (c) an equine heavy chain constant region selected from an IgG1, IgG2, IgG3, IgG4, IgG5, IgG6 and IgG7 constant region.

In some embodiments, the antibody comprises:
a. (i) a light chain amino acid sequence of SEQ ID NO: 26; (ii) a heavy chain amino acid sequence of SEQ ID NO: 27; or (iii) a light chain amino acid sequence as in (i) and a heavy chain amino acid sequence as in (ii); or
b. (i) a light chain amino acid sequence of SEQ ID NO: 30; (ii) a heavy chain amino acid sequence of SEQ ID NO: 31; or (iii) a light chain amino acid sequence as in (i) and a heavy chain amino acid sequence as in (ii); or
c. (i) a light chain amino acid sequence of SEQ ID NO: 34; (ii) a heavy chain amino acid sequence of SEQ ID NO: 35; or (iii) a light chain amino acid sequence as in (i) and a heavy chain amino acid sequence as in (ii).

In some embodiments, the antibody comprises a light chain amino acid sequence of SEQ ID NO: 21. In some embodiments, the antibody comprises a heavy chain amino acid sequence of SEQ ID NO: 17; SEQ ID NO: 18; SEQ ID NO: 19; or SEQ ID NO: 20.

In some embodiments, the antibody is an antibody fragment selected from Fv, scFv, Fab, Fab', F(ab')2, and Fab'-SH.

In some embodiments, the antibody is bi-specific, wherein the antibody binds to IL31 and one or more antigens selected from IL17, TNFα, CD20, CD19, CD25, IL4, IL13, IL23, IgE, CD11α, IL6R, α4-Intergrin, IL12, IL1β, or BlyS.

In some embodiments, an isolated nucleic acid is provided, which encodes an anti-IL31 antibody described herein above. In some embodiments, a host cell is provided, which comprises a nucleic acid encoding an anti-IL31 antibody described herein above. In some embodiments, a method of producing an anti-IL31 antibody is provided, which comprises culturing such a host cell comprising a nucleic acid encoding an anti-IL31 antibody described herein above and isolating the antibody. In some embodiments, a pharmaceutical composition is provided, which comprises an anti-IL31 antibody described herein and a pharmaceutically acceptable carrier.

In some embodiments, methods of treating a companion animal species having an IL31-induced condition are provided, comprising administering to the companion animal species a therapeutically effective amount of an anti-IL31 antibody described herein or a pharmaceutical composition comprising the antibody described herein. In some embodiments, the companion animal species is canine, feline, or equine. In some embodiments, the IL31-induced condition is a pruritic or allergic condition. In some embodiments, the IL31-induced condition is selected from atopic dermatitis, pruritus, asthma, psoriasis, scleroderma and eczema.

In some embodiments, the anti-IL31 antibody or the pharmaceutical composition is administered parenterally. In some embodiments, the anti-IL31 antibody or the pharmaceutical composition is administered by an intramuscular route, an intraperitoneal route, an intracerebrospinal route, a subcutaneous route, an intra-arterial route, an intrasynovial route, an intrathecal route, or an inhalation route.

In some embodiments, the method comprises administering in combination with the anti-IL31 antibody or the pharmaceutical composition a Jak inhibitor, a PI3K inhibitor, an AKT inhibitor, or a MAPK inhibitor. In some embodiments, the method comprises administering in combination with the anti-IL31 antibody or the pharmaceutical composition one or more antibodies selected from an anti-IL17 antibody, an anti-TNFα antibody, an anti-CD20 antibody, an anti-CD19 antibody, an anti-CD25 antibody, an anti-IL4 antibody, an anti-IL13 antibody, an anti-IL23 antibody, an anti-IgE antibody, an anti-CD11α antibody, anti-IL6R antibody, anti-α4-Intergrin antibody, an anti-IL12 antibody, an anti-IL1β antibody, and an anti-BlyS antibody.

In some embodiments, methods of reducing IL31 signaling function in a cell are provided, comprising exposing to the cell an anti-IL31 antibody the pharmaceutical composition described herein under conditions permissive for binding of the antibody to extracellular IL31, thereby reducing binding to IL31 receptor and/or reducing IL31 signaling function by the cell. In some embodiments, the cell is exposed to the antibody or the pharmaceutical composition ex vivo. In some embodiments, the cell is exposed to the antibody or the pharmaceutical composition in vivo. In some embodiments, the cell is a canine cell, a feline cell, or an equine cell.

In some embodiments, a method for detecting IL31 in a sample from a companion animal species are provided, comprising contacting the sample with an anti-IL31 antibody or the pharmaceutical composition described herein under conditions permissive for binding of the antibody to IL31, and detecting whether a complex is formed between the antibody and IL31 in the sample. In some embodiments, the sample is a biological sample obtained from a canine, a feline, or an equine.

BRIEF DESCRIPTION OF THE DRAWINGS

FIG. 1A is an alignment of variable light sequences of M14, M18, M19, and M87 mouse monoclonal antibody clones. FIG. 1B is an alignment of variable heavy sequences of M14, M18, M19, and M87 mouse monoclonal antibody clones.

FIGS. 7A and 7B are immunoblots of feline and equine IL31 proteins fused to human Fc probed with M14 antibody and anti-FC antibody, respectively.

DESCRIPTION OF CERTAIN SEQUENCES

TABLE 1

Figure 2A:
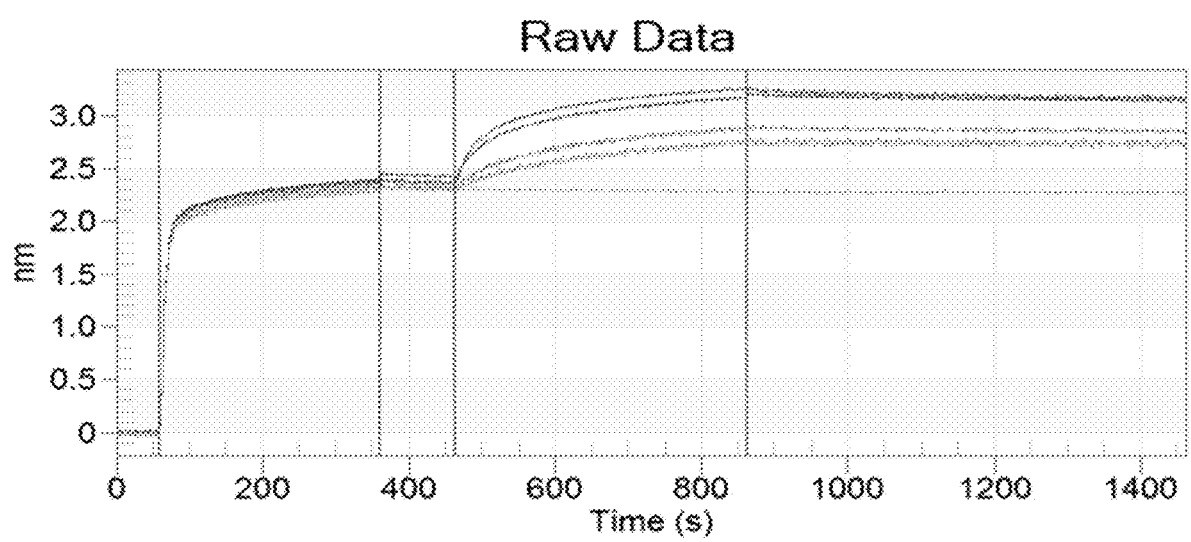
FIG. 2A and FIG. 2B are graphs of canine IL31 binding analysis with varying concentrations of chimeric M14 antibody.

Table 1 provides a listing of certain sequences referenced herein.
Description of Certain Sequences

| SEQ ID NO: | SEQUENCE | DESCRIPTION |
|---|---|---|
| 1 | GDSITSGYW | Variable heavy chain CDR-H1 amino acid sequence of mouse antibody clone M14 |
| 2 | YISYSGITDYNPSLKS | Variable heavy chain CDR-H2 amino acid sequence of mouse antibody clone M14 |
| 3 | ARYGNYGYAMDY | Variable heavy chain CDR-H3 amino acid sequence of mouse antibody clone M14 |
| 4 | EVQLQESGPSLVKPSQTLSLTCSVT | Variable region heavy chain framework HC-FR1 amino acid sequence of mouse antibody clone M14 |
| 5 | NWIRKFPGNKLEYMG | Variable region heavy chain framework HC-FR2 amino acid sequence of mouse antibody clone M14 |
| 6 | RISITRDTSKNQYYLQLNSVTTEDTATYYC | Variable region heavy chain framework HC-FR3 amino acid sequence of mouse antibody clone M14 |
| 7 | WGQGTSVTVSS | Variable region heavy chain framework HC-FR4 amino acid sequence of mouse antibody clone M14 |
| 8 | RASESVDTYGNSFMH | Variable light chain CDR-L1 amino acid sequence of mouse antibody clone M14 |
| 9 | RASNLES | Variable light chain CDR-L2 amino acid sequence of mouse antibody clone M14 |
| 10 | QQSYEDPWT | Variable light chain CDR-L3 amino acid sequence of mouse antibody clone M14 |
| 11 | DIVLTQSPASLAVSLGQRATISC | Variable region light chain framework LC-FR1 amino acid sequence of mouse antibody clone M14 |
| 12 | WYQQKSGQSPKLLIY | Variable region light chain framework LC-FR2 amino acid sequence of mouse antibody clone M14 |
| 13 | GIPARFGGSGSRTDFTLTIDPVEADDVATYYC | Variable region light chain framework LC-FR3 amino acid sequence of mouse antibody clone M14 |

TABLE 1-continued

Table 1 provides a listing of certain sequences referenced herein.
Description of Certain Sequences

| SEQ ID NO: | SEQUENCE | DESCRIPTION |
|---|---|---|
| 14 | FGGGTKLEIK | Variable region light chain framework LC-FR4 amino acid sequence of mouse antibody clone M14 |
| 15 | EVQLVESGPSLVKPGGSLRLTCSVTGDSITSGYWNWI RKFPGNKLEYMGYISYSGITDYNPSLKSRITISRDTS KNQYYLQLNSVTTEDTATYYCARYGNYGYAMDYWGQG TLVTVSS | Caninized variable heavy chain amino acid sequence of mouse antibody clone M14 |
| 16 | DIVMTQSPASLSVSLGQRATISCRASESVDTYGNSFM HWYQQKPGQSPKLLIYRASNLESGIPARFGGSGSGTD FTLTIDPVQADDVATYYCQQSYEDPWTFGGGTKLEIK | Caninized variable light chain amino acid sequence of mouse antibody clone M14 |
| 17 | EVQLVESGPSLVKPGGSLRLTCSVTGDSITSGYWNWI RKFPGNKLEYMGYISYSGITDYNPSLKSRITISRDTS KNQYYLQLNSVTTEDTATYYCARYGNYGYAMDYWGQG TLVTVSSASTTAPSVFPLAPSCGSTSGSTVALACLVS GYFPEPVTVSWNSGSLTSGVHTFPSVLQSSGLHSLSS MVTVPSSRWPSETFTCNVVHPASNTKVDKPVFNECRC TDTPCPVPEPLGGPSVLIFPPKPKDILRITRIPEVTC VVLDLGREDPEVQISWFVDGKEVHTAKTQSREQQFNG TYRVVSVLPIEHQDWLTGKEFKCRVNHIDLPSPIERT ISKARGRAHKPSVYVLPPSPKELSSSDTVSITCLIKD FYPPDIDVEWQSNGQQEPERKHRMTPPQLDEDGSYFL YSKLSVDKSRWQQGDPFTCAVMHETLQNHYTDLSLSH SPGK | Caninized heavy chain sequence from mouse antibody clone M14 and canine IgG-A |
| 18 | EVQLVESGPSLVKPGGSLRLTCSVTGDSITSGYWNWI RKFPGNKLEYMGYISYSGITDYNPSLKSRITISRDTS KNQYYLQLNSVTTEDTATYYCARYGNYGYAMDYWGQG TLVTVSSASTTAPSVFPLAPSCGSTSGSTVALACLVS GYFPEPVTVSWNSGSLTSGVHTFPSVLQSSGLYSLSS MVTVPSSRWPSETFTCNVAHPASKTKVDKPVPKRENG RVPRPPDCPKCPAPEMLGGPSVFIFPPKPKDTLLIAR TPEVTCVVVDLDPEDPEVQISWFVDGKQMQTAKTQPR EEQFNGTYRVVSVLPIGHQDWLKGKQFTCKVNNKALP SPIERTISKARGQAHQPSVYVLPPSREELSKNTVSLT CLIKDFFPPDIDVEWQSNGQQEPESKYRTTPPQLDED GSYFLYSKLSVDKSRWQRGDTFICAVMHEALHNHYTQ ESLSHSPGK | Caninized heavy chain sequence from mouse antibody clone M14 and canine IgG-B |
| 19 | EVQLVESGPSLVKPGGSLRLTCSVTGDSITSGYWNWI RKFPGNKLEYMGYISYSGITDYNPSLKSRITISRDTS KNQYYLQLNSVTTEDTATYYCARYGNYGYAMDYWGQG TLVTVSSASTTAPSVFPLAPSCGSQSGSTVALACLVS GYIPEPVTVSWNSVSLTSGVHTFPSVLQSSGLYSLSS MVTVPSSRWPSETFTCNVAHPATNTKVDKPVAKECEC KCNCNNCPCPGCGLLGGPSVFIFPPKPKDILVTARTP TVTCVVVDLDPENPEVQISWFVDSKQVQTANTQPREE QSNGTYRVVSVLPIGHQDWLSGKQFKCKVNNKALPSP IEEIISKTPGQAHQPNVYVLPPSRDEMSKNTVTLTCL VKDFFPPEIDVEWQSNGQQEPESKYRMTPPQLDEDGS YFLYSKLSVDKSRWQRGDTFICAVMHEALHNHYTQIS LSHSPGK | Caninized heavy chain sequence from mouse antibody clone M14 and canine IgG-C |
| 20 | EVQLVESGPSLVKPGGSLRLTCSVTGDSITSGYWNWI RKFPGNKLEYMGYISYSGITDYNPSLKSRITISRDTS KNQYYLQLNSVTTEDTATYYCARYGNYGYAMDYWGQG TLVTVSSASTTAPSVFPLAPSCGSTSGSTVALACLVS GYFPEPVTVSWNSGSLTSGVHTFPSVLQSSGLYSLSS TVTVPSSRWPSETFTCNVVHPASNTKVDKPVPKESTC KCISPCPVPESLGGPSVFIFPPKPKDILRITRIPEIT CVVLDLGREDPEVQISWFVDGKEVHTAKTQPREQQFN STYRVVSVLPIEHQDWLTGKEFKCRVNHIGLPSPIER TISKARGQAHQPSVYVLPPSPKELSSSDTVTLICLIK DFFPPEIDVEWQSNGQPEPESKYHTTAPQLDEDGSYF LYSKLSVDKSRWQQGDTFTCAVMHEALQNHYTDLSLS HSPGK | Caninized heavy chain sequence from mouse antibody clone M14 and canine IgG-D |

TABLE 1-continued

Table 1 provides a listing of certain sequences referenced herein.
Description of Certain Sequences

| SEQ ID NO: | SEQUENCE | DESCRIPTION |
|---|---|---|
| 21 | DIVMTQSPASLSVSLGQRATISCRASESVDTYGNSFM HWYQQKPGQSPKLLIYRASNLESGIPARFGGSGSGTD FTLTIDPVQADDVATYYCQQSYEDPWTFGGGTKLEIK RNDAQPAVYLFQPSPDQLHTGSASVVCLLNSFYPKDI NVKWKVDGVIQDTGIQESVTEQDKDSTYSLSSTLTMS STEYLSHELYSCEITHKSLPSTLIKSFQRSECQRVD | Caninized light chain sequence from mouse antibody clone M14 and canine light chain constant region |
| 22 | MLSHTGPSRFALFLLCSMETLLSSHMAPTHQLPPSDV RKIILELQPLSRGLLEDYQKKETGVPESNRTLLLCLT SDSQPPRLNSSAILPYFRAIRPLSDKNIIDKIIEQLD KLKFQHEPETEISVPADTFECKSFILTILQQFSACLE SVFKSLNSGPQ | Canine IL31 amino acid sequence |
| 23 | PSDVRKIILELQPLSRG | Canine IL31 epitope |
| 24 | DIVLTQSPASLAVSLGQRATISCRASESVDTYGNSFM HWYQQKSGQSPKLLIYRASNLESGIPARFGGSGSRTD FTLTIDPVEADDVATYYCQQSYEDPWTFGGGTKLEIK | Variable light chain amino acid sequence of mouse antibody clone M14 |
| 25 | EVQLQESGPSLVKPSQTLSLTCSVTGDSITSGYWMWI RKFPGNKLEYMGYISYSGITDYNPSLKSRISITRDTS KNQYYLQLNSVTTEDTATYYCARYGNYGYAMDYWGQG TSVTVSS | Variable heavy chain amino acid sequence of mouse antibody clone M14 |
| 26 | DIVLTQSPASLAVSLGQRATISCRASESVDTYGNSFM HWYQQKSGQSPKLLIYRASNLESGIPARFGGSGSRTD FTLTIDPVEADDVATYYCQQSYEDPWTFGGGTKLEIK RNDAQPAVYLFQPSPDQLHTGSASVVCLLNSFYPKDI NVKWKVDGVIQDTGIQESVTEQDKDSTYSLSSTLTMS STEYLSHELYSCEITHKSLPSTLIKSFQRSECQRVD | Chimeric variable light chain of mouse antibody clone M14 and canine light chain constant region |
| 27 | EVQLQESGPSLVKPSQTLSLTCSVTGDSITSGYWNWI RKFPGNKLEYMGYISYSGITDYNPSLKSRISITRDTS KNQYYLQLNSVTTEDTATYYCARYGNYGYAMDYWGQG TSVTVSSASTTAPSVFPLAPSCGSTSGSTVALACLVS GYFPEPVTVSWNSGSLTSGVHTFPSVLQSSGLYSLSS MVTVPSSRWPSETFTCNVAHPASKTKVDKPVPKRENG RVPRPPDCPKCPAPEMLGGPSVFIFPPKPKDTLLIAR TPEVTCVVVDLDPEDPEVQISWFVDGKQMQTAKTQPR EEQFNGTYRVVSVLPIGHQDWLKGKQFTCKVNNKALP SPIERTISKARGQAHQPSVYVLPPSREELSKNTVSLT CLIKDFFPPDIDVEWQSNGQQEPESKYRTTPPQLDED GSYFLYSKLSVDKSRWQRGDTFICAVMHEALHNHYTQ ESLSHSPGK | Chimeric variable heavy chain of mouse antibody clone M14 and canine IgG-B |
| 28 | MLSHAGPARFALFLLCCMETLLPSHMAPAHRLQPSDV RKIILELRPMSKGLLQDYLKKEIGLPESNHSSLPCLS SDSQLPHINGSAILPYFRAIRPLSDKNTIDKIIEQLD KLKFQREPEAKVSMPADNFERKNFILAVLQQFSACLE HVLQSLNSGPQ | Feline IL31 amino acid sequence |
| 29 | MVSHIGSTRFALFLLCCLGTLMFSHTGPIYQLQPKEI QAIIVELQNLSKKLLDDYLNKEKGVQKFDSDLPSCFT SDSQAPGNINSSAILPYFKAISPSLNNDKSLYIIEQL DKLNFQNAPETEVSMPTDNFERKRFILTILRWFSNCL ELAMKTLTTAEQALPPLDPSTPHAGAVALTHHQQDRT ALDRAVFPFVWAAPRGGEVGDGGH | Equine IL31 amino acid sequence |
| 30 | DIVLTQSPASLAVSLGQRATISCRASESVDTYGNSFM HWYQQKSGQSPKLLIYRASNLESGIPARFGGSGSRTD FTLTIDPVEADDVATYYCQQSYEDPWTFGGGTKLEIK RSDAQPSVFLFQPSLDELHTGSASIVCILNDFYPKEV NVKWKVDGVVQNKGIQESTTEQNSKDSTYSLSSTLTM SSTEYQSHEKFSCEVTHKSLASTLVKSFNRSECQRE | Chimeric variable light chain of mouse antibody clone M14 and feline light chain constant region |
| 31 | EVQLQESGPSLVKPSQTLSLTCSVTGDSITSGYWNWI RKFPGNKLEYMGYISYSGITDYNPSLKSRISITRDTS KNQYYLQLNSVTTEDTATYYCARYGNYGYAMDYWGQG TSVTVSSASTTAPSVFPLAPSCGTTSGATVALACLVL GYFPEPVTVSWNSGALTSGVHTFPAVLQASGLYSLSS MVTVPSSRWLSDTFTCNVAHPPSNTKVDKTVRKTDHP PGPKPCDCPKCPPPEMLGGPSIFIFPPKPKDTLSISR TPEVTCLVVDLGPDDSDVQITWFVDNTQVYTAKTSPR | Chimeric variable heavy chain of mouse antibody clone M14 and feline heavy chain constant region |

TABLE 1-continued

Table 1 provides a listing of certain sequences referenced herein.
Description of Certain Sequences

| SEQ ID NO: | SEQUENCE | DESCRIPTION |
|---|---|---|
|  | EEQFNSTYRVVSVLPILHQDWLKGKEFKCKVNSKSLP SPIERTISKAKGQPHEPQVYVLPPAQEELSRNKVSVT CLIKSFHPPDIAVEWEITGQPEPENNYRTTPPQLDSD GTYFVYSKLSVDRSHWQRGNTYTCSVSHEALHSHHTQ KSLTQSPGK |  |
| 32 | EIQMTQSPSSLSASPGDRVTISCRASESVDTYGNSFM HWYQQKPGQSPKLLIYRASNLESGVPSRFSGSGSGTD FTLTISSLEPEDAATYYCQQSYEDPWTFGGGTKLEIK | Felinized variable light chain sequence from mouse antibody clone M14 |
| 33 | DVQLVESGGDLVKPGGSLRLTCSVTGDSITSGYWNWV RQAPGKGLQWVAYISYSGITDYADSVKGRFTISRDNA KNTLYLQLNNLKAEDTATYYCARYGNYGYAMDYWGQG TLVTVSS | Felinized variable heavy chain sequence from mouse antibody clone M14 |
| 34 | EIQMTQSPSSLSASPGDRVTISCRASESVDTYGNSFM HWYQQKPGQSPKLLIYRASNLESGVPSRFSGSGSGTD FTLTISSLEPEDAATYYCQQSYEDPWTFGGGTKLEIK RSDAQPSVFLFQPSLDELHTGSASIVCILNDFYPKEV NVKWKVDGVVQNKGIQESTTEQNSKDSTYSLSSTLTM SSTEYQSHEKFSCEVTHKSLASTLVKSFNRSECQRE | Felinized variable light chain sequence from mouse antibody clone M14 |
| 35 | DVQLVESGGDLVKPGGSLRLTCSVTGDSITSGYWNWV RQAPGKGLQWVAYISYSGITDYADSVKGRFTISRDNA KNTLYLQLNNLKAEDTATYYCARYGNYGYAMDYWGQG TLVTVSSASTTAPSVFPLAPSCGTTSGATVALACLVL GYFPEPVTVSWNSGALTSGVHTFPAVLQASGLYSLSS MVTVPSSRWLSDTFTCNVAHPPSNTKVDKTVRKTDHP PGPKPCDCPKCPPPEMLGGPSIFIFPPKPKDTLSISR TPEVTCLVVDLGPDDSDVQITWFVDNTQVYTAKTSPR EEQFNSTYRVVSVLPILHQDWLKGKEFKCKVNSKSLP SPIERTISKAKGQPHEPQVYVLPPAQEELSRNKVSVT CLIKSFHPPDIAVEWEITGQPEPENNYRTTPPQLDSD GTYFVYSKLSVDRSHWQRGNTYTCSVSHEALHSHHTQ KSLTQSPGK | Felinized variable heavy chain sequence from mouse antibody clone M14 |

DESCRIPTION OF CERTAIN EMBODIMENTS

Antibodies that bind canine IL31, feline IL31, or equine IL31 are provided. Antibody heavy chains and light chains that are capable of forming antibodies that bind IL31 are also provided. In addition, antibodies, heavy chains, and light chains comprising one or more particular complementary determining regions (CDRs) are provided. Polynucleotides encoding antibodies to canine IL31 are provided. Methods of producing or purifying antibodies to canine IL31 are also provided. Methods of treatment using antibodies to canine IL31 are provided. Such methods include, but are not limited to, methods of treating IL31-induced conditions in companion animal species. Methods of detecting IL31 in a sample from a companion animal species are provided.

For the convenience of the reader, the following definitions of terms used herein are provided.

As used herein, numerical terms such as Kd are calculated based upon scientific measurements and, thus, are subject to appropriate measurement error. In some instances, a numerical term may include numerical values that are rounded to the nearest significant figure.

As used herein, "a" or "an" means "at least one" or "one or more" unless otherwise specified. As used herein, the term "or" means "and/or" unless specified otherwise. In the context of a multiple dependent claim, the use of "or" when referring back to other claims refers to those claims in the alternative only.

Anti-IL31 Antibodies

Novel antibodies directed against IL31 are provided, for example antibodies that bind to canine IL31, feline IL31, and equine IL31. Anti-IL31 antibodies provided herein include, but are not limited to, monoclonal antibodies, mouse antibodies, chimeric antibodies, caninized antibodies, felinized antibodies, and equinized antibodies. In some embodiments, an anti-IL31 antibody is an isolated mouse monoclonal antibody such as M14, M18, M19, and M87.

Monoclonal antibodies M14, M18, M19, and M87 were isolated as follows. Briefly, mice were immunized with canine IL31 and mouse monoclonal antibody clones were obtained through standard hybridoma technology. Enzyme linked immunosorbent assay (ELISA) was used to screen for hybridoma clones producing IL31-binding antibodies. Based on binding affinity and a cell-based functional assay described herein, hybridoma clones producing monoclonal antibodies M14, M18, M19, and M87 were selected for further investigation. The variable heavy chain (VH) and variable light chain (VL) of each of the four clones were sequenced and analyzed by sequence alignment (FIG. 1).

Also provided herein are amino acid sequences of monoclonal antibody M14. For example, the variable heavy chain CDRs (SEQ ID NOs: 1-3), variable light chain CDRs (SEQ ID NOs: 8-10), variable region heavy chain framework sequences (SEQ ID NOs: 4-7), and variable region light chain framework sequences (SEQ ID NOs: 11-14) for monoclonal antibody M14 are provided. The amino acid sequences of the variable light chain and variable heavy chain of monoclonal antibody M14 are provided (SEQ ID NOs: 24 and 25, respectively). In addition, the amino acid sequences of the CDRs, framework sequences, variable light chain, variable heavy chain of monoclonal antibodies M18, M19, and M87 are provided (FIG. 1).

Also provided herein are chimeric, caninized, felinized, and equinized antibodies derived from monoclonal antibody M14. In some embodiments, amino acid sequences of caninized monoclonal antibody M14 are provided, such as SEQ ID NOs: 15-21. In some embodiments, amino acid sequences of felinized antibodies derived from monoclonal antibody M14 are provided, such as SEQ ID NOs: 32-35. In some embodiments, amino acid sequences of chimeric antibodies derived from monoclonal antibody M14 are provided, such as SEQ ID NOs: 26, 27, 30, and 31.

The term "antibody" herein is used in the broadest sense and encompasses various antibody structures, including but not limited to monoclonal antibodies, polyclonal antibodies, multispecific antibodies (for example, bispecific (such as Bi-specific T-cell engagers) and trispecific antibodies), and antibody fragments (such as Fab, F(ab')2, ScFv, minibody, diabody, triabody, and tetrabody) so long as they exhibit the desired antigen-binding activity. Canine, feline, and equine species have different varieties (classes) of antibodies that are shared by many mammalians.

The term antibody includes, but is not limited to, fragments that are capable of binding to an antigen, such as Fv, single-chain Fv (scFv), Fab, Fab', di-scFv, sdAb (single domain antibody) and (Fab')2 (including a chemically linked F(ab')2). Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen combining sites and is still capable of crosslinking antigen. The term antibody also includes, but is not limited to, chimeric antibodies, humanized antibodies, and antibodies of various species such as mouse, human, cynomolgus monkey, canine, feline, equine, etc. Furthermore, for all antibody constructs provided herein, variants having the sequences from other organisms are also contemplated. Thus, if a murine version of an antibody is disclosed, one of skill in the art will appreciate how to transform the murine sequence based antibody into a cat, dog, horse, etc. sequence. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, mouse scFv or a canine scFv). This denotes the sequences of at least part of the non-CDR regions, rather than the source of the construct. In some embodiments, the antibodies comprise a label or are conjugated to a second moiety.

The terms "label" and "detectable label" mean a moiety attached to an antibody or its analyte to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^3$H, $^{14}$C, $^{35}$S, $^{90}$Y, $^{99}$Tc, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

The term "monoclonal antibody" refers to an antibody of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to poly clonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

In some embodiments, the monoclonal antibody is an isolated mouse antibody selected from clone M14, M18, M19, and M87.

"Amino acid sequence," means a sequence of amino acids residues in a peptide or protein. The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

"IL31" as used herein refers to any native IL31 that results from expression and processing of IL31 in a cell. The term includes IL31 from any vertebrate source, including mammals such as primates (e.g., humans and cynomolgus monkeys) and rodents (e.g., mice and rats), and companion animals (e.g., dogs, cats, and equine), unless otherwise indicated. The term also includes naturally occurring variants of IL31, e.g., splice variants or allelic variants.

In some embodiments, a canine IL31 comprises the amino acid sequence of SEQ ID NO: 22. In some embodiments, a feline IL31 comprises the amino acid sequence of SEQ ID NO: 28. In some embodiments, an equine IL31 comprises the amino acid sequence of SEQ ID NO: 29.

The term "IL31 binding domain" of an antibody means the binding domain formed by a light chain and heavy chain of an anti-IL31 antibody, which binds IL31.

In some embodiments, the IL31 binding domain binds canine IL31 with greater affinity than it binds human IL31. In some embodiments, the IL31 binding domain binds IL31 of other companion animals, such as feline IL31 or equine IL31.

As used herein, the term "epitope" refers to a site on a target molecule (for example, an antigen, such as a protein, nucleic acid, carbohydrate or lipid) to which an antigen-binding molecule (for example, an antibody, antibody fragment, or scaffold protein containing antibody binding regions) binds. Epitopes often include a chemically active surface grouping of molecules such as amino acids, polypeptides or sugar side chains and have specific three dimensional structural characteristics as well as specific charge characteristics. Epitopes can be formed both from contiguous or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some examples an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between an antibody residue and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antibody. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

In some embodiments, the epitope comprises the amino acid sequence of SEQ ID NO: 23. In some embodiments, the epitope is within amino acids 34-50 of SEQ ID NO: 22. In some embodiments, the epitope comprises amino acids 34-50 of SEQ ID NO: 22.

The term "CDR" means a complementarity determining region as defined by at least one manner of identification to one of skill in the art. In some embodiments, CDRs can be defined in accordance with any of the Chothia numbering schemes, the Kabat numbering scheme, a combination of Kabat and Chothia, the AbM definition, the contact definition, or a combination of the Kabat, Chothia, AbM, or contact definitions. The various CDRs within an antibody can be designated by their appropriate number and chain type, including, without limitation as CDR-H1, CDR-H2, CDR-H3, CDR-L1, CDR-L2, and CDR-L3. The term "CDR" is used herein to also encompass a "hypervariable region" or HVR, including hypervariable loops.

In some embodiments, an anti-IL31 antibody comprises a heavy chain comprising (a) a CDR-H1 comprising the amino acid sequence of SEQ ID NO: 1; (b) a CDR-H2 comprising the amino acid sequence of SEQ ID NO: 2; or (c) a CDR-H3 comprising the amino acid sequence of SEQ ID NO: 3. In some embodiments, an anti-IL31 antibody comprises a light chain comprising (a) a CDR-L1 comprising the amino acid sequence of SEQ ID NO: 8; (b) a CDR-L2 comprising the amino acid sequence of SEQ ID NO: 9; or (c) a CDR-L3 comprising the amino acid sequence of SEQ ID NO: 10.

In some embodiments, an anti-IL31 antibody comprises a heavy chain comprising (a) a CDR-H1 comprising the amino acid sequence of SEQ ID NO: 1, (b) a CDR-H2 comprising the amino acid sequence of SEQ ID NO: 2, and (c) a CDR-H3 comprising the amino acid sequence of SEQ ID NO: 3; and a light chain comprising (a) a CDR-L1 comprising the amino acid sequence of SEQ ID NO: 8, (b) a CDR-L2 comprising the amino acid sequence of SEQ ID NO: 9, and (c) a CDR-L3 comprising the amino acid sequence of SEQ ID NO: 10.

The term "variable region" as used herein refers to a region comprising at least three CDRs. In some embodiments, the variable region includes the three CDRs and at least one framework region ("FR"). The terms "heavy chain variable region" or "variable heavy chain" are used interchangeably to refer to a region comprising at least three heavy chain CDRs. The terms "light chain variable region" or "variable light chain" are used interchangeably to refer to a region comprising at least three light chain CDRs. In some embodiments, the variable heavy chain or variable light chain comprises at least one framework region. In some embodiments, an antibody comprises at least one heavy chain framework region selected from HC-FR1, HC-FR2, HC-FR3, and HC-FR4. In some embodiments, an antibody comprises at least one light chain framework region selected from LC-FR1, LC-FR2, LC-FR3, and LC-FR4. The framework regions may be juxtaposed between light chain CDRs or between heavy chain CDRs. For example, an antibody may comprise a variable heavy chain having the following structure: (HC-FR1)-(CDR-H1)-(HC-FR2)-(CDR-H2)-(HC-FR3)-(CDR-H3)-(HC-FR4). An antibody may comprise a variable heavy chain having the following structure: (CDR-H1)-(HC-FR2)-(CDR-H2)-(HC-FR3)-(CDR-H3). An antibody may also comprise a variable light chain having the following structure: (LC-FR1)-(CDR-L1)-(LC-FR2)-(CDR-L2)-(LC-FR3)-(CDR-L3)-(LC-FR4). An antibody may also comprise a variable light chain having the following structure: (CDR-L1)-(LC-FR2)-(CDR-L2)-(LC-FR3)-(CDR-L3).

In some embodiments, an anti-IL31 antibody comprises one or more of (a) a variable region heavy chain framework 1 (HC-FR1) sequence of SEQ ID NO: 4, (b) a HC-FR2 sequence of SEQ ID NO: 5, (c) a HC-FR3 sequence of SEQ ID NO: 6, (d) a HC-FR4 sequence of SEQ ID NO: 7, (e) a variable region light chain framework 1 (LC-FR1) sequence of SEQ ID NO: 11, (f) an LC-FR2 sequence of SEQ ID NO: 12, (g) an LC-FR3 sequence of SEQ ID NO: 13, or (h) an LC-FR4 sequence of SEQ ID NO: 14. In some embodiments, an anti-IL31 antibody comprises a variable light chain sequence of (a) SEQ ID NO: 16, (b) SEQ ID NO: 24, or (c) SEQ ID NO: 32. In some embodiments, an anti-IL31 antibody comprises a variable heavy chain sequence of (a) SEQ ID NO: 15; (b) SEQ ID NO: 25; or (c) SEQ ID NO: 33. In some embodiments, an anti-IL31 antibody comprises (a) a variable light chain sequence of SEQ ID NO: 16 and a variable heavy chain sequence of SEQ ID NO: 15; (b) a variable light chain sequence of SEQ ID NO: 24 and a variable heavy chain sequence of SEQ ID NO: 25; or (c) a variable light chain sequence of SEQ ID NO: 32 and a variable heavy chain sequence of SEQ ID NO: 33.

The term "constant region" as used herein refers to a region comprising at least three constant domains. The terms "heavy chain constant region" or "constant heavy chain" are used interchangeably to refer to a region comprising at least three heavy chain constant domains, CH1, CH2, and CH3. Nonlimiting exemplary heavy chain constant regions include γ, δ, α, ε, and μ. Each heavy chain constant region corresponds to an antibody isotype. For example, an antibody comprising a γ constant region is an IgG antibody, an antibody comprising a δ constant region is an IgD antibody, an antibody comprising an α constant region is an IgA antibody, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $\gamma_1$ constant region), IgG2 (comprising a $\gamma_2$ constant region), IgG3 (comprising a $\gamma_3$ constant region), and IgG4 (comprising a $\gamma_4$ constant region) antibodies; IgA antibodies include, but are not limited to, IgA1 (comprising an $\alpha_1$ constant region) and IgA2 (comprising an $\alpha_2$ constant region) antibodies; and IgM antibodies include, but are not limited to IgM1 and IgM2. The terms "light chain constant region" or "constant light chain" are used interchangeably to refer to a region comprising a light chain constant domain, CL. Nonlimiting exemplary light chain constant regions include λ and κ. Non-function-altering deletions and alterations within the domains are encompassed within the scope of the term "constant region" unless designated otherwise. Canine, feline, and equine have antibody classes such as IgG, IgA, IgD, IgE, and IgM. Within the canine IgG antibody class are IgG-A, IgG-B, IgG-C, and IgG-D. Within the feline IgG antibody class are IgG1a, IgG1b, and IgG2. Within the equine IgG antibody class are IgG1, IgG2, IgG3, IgG4, IgG5, IgG6, and IgG7.

The term "chimeric antibody" or "chimeric" refers to an antibody in which a portion of the heavy chain or light chain is derived from a particular source or species, while at least a part of the remainder of the heavy chain or light chain is derived from a different source or species. In some embodiments, a chimeric antibody refers to an antibody comprising at least one variable region from a first species (such as mouse, rat, cynomolgus monkey, etc.) and at least one constant region from a second species (such as human, dog, cat, equine, etc.). In some embodiments, a chimeric antibody comprises at least one mouse variable region and at least one canine constant region. In some embodiments, a chimeric antibody comprises at least one mouse variable region and at least one feline constant region. In some embodiments, all of the variable regions of a chimeric antibody are from a first species and all of the constant regions of the chimeric antibody are from a second species. In some embodiments, a chimeric antibody comprises a constant heavy chain region or constant light chain region from a companion animal. In some embodiments, a chimeric antibody comprises a mouse variable heavy and light chains and a companion animal constant heavy and light chains. For example, a chimeric antibody may comprise a mouse variable heavy and light chains and a canine constant heavy and light chains; a chimeric antibody may comprise a mouse variable heavy and light chains and a feline constant heavy and light chains; or a chimeric antibody may comprise a mouse variable heavy and light chains and an equine constant heavy and light chains.

In some embodiments, an anti-IL31 antibody comprises a chimeric antibody comprising:

a. (i) a light chain amino acid sequence of SEQ ID NO: 26; (ii) a heavy chain amino acid sequence of SEQ ID NO: 27; or (iii) a light chain amino acid sequence as in (i) and a heavy chain sequence as in (ii); or b. (i) a light chain amino acid sequence of SEQ ID NO: 30; (ii) a heavy chain amino acid sequence of SEQ ID NO: 31; or (iii) a light chain amino acid sequence as in (i) and a heavy chain sequence as in (ii).

A "canine chimeric" or "canine chimeric antibody" refers to a chimeric antibody having at least a portion of a heavy chain or a portion of a light chain derived from a dog. A "feline chimeric" or "feline chimeric antibody" refers to a chimeric antibody having at least a portion of a heavy chain or a portion of a light chain derived from a cat. An "equine chimeric" or "equine chimeric antibody" refers to a chimeric antibody having at least a portion of a heavy chain or a portion of a light chain derived from a horse. In some embodiments, a canine chimeric antibody comprises a mouse variable heavy and light chains and a canine constant heavy and light chains. In some embodiments, a feline chimeric antibody comprises a mouse variable heavy and light chains and a feline constant heavy and light chains. In some embodiments, an equine chimeric antibody comprises a mouse variable heavy and light chains and an equine constant heavy and light chains. In some embodiments, the antibody is a chimeric antibody comprising murine variable heavy chain framework regions or murine variable light chain framework regions.

A "canine antibody" as used herein encompasses antibodies produced in a canine; antibodies produced in non-canine animals that comprise canine immunoglobulin genes or comprise canine immunoglobulin peptides; or antibodies selected using in vitro methods, such as phage display, wherein the antibody repertoire is based on a canine immunoglobulin sequence. The term "canine antibody" denotes the genus of sequences that are canine sequences. Thus, the term is not designating the process by which the antibody was created, but the genus of sequences that are relevant.

In some embodiments, an anti-IL31 antibody comprises a canine heavy chain constant region selected from an IgG-A, IgG-B, IgG-C, and IgG-D constant region. In some embodiments, an anti-IL31 antibody is a canine IgG-A, IgG-B, IgG-C, or IgG-D antibody. In some embodiments, an anti-IL31 antibody is (a) a canine IgG-A antibody comprising the heavy chain amino acid sequence of SEQ ID NO: 17; (b) a canine IgG-B antibody comprising the heavy chain amino acid sequence of SEQ ID NO: 18; (c) a canine IgG-C antibody comprising the heavy chain amino acid sequence of SEQ ID NO: 19; or (d) a canine IgG-D antibody comprising the heavy chain amino acid sequence of SEQ ID NO: 20.

A "feline antibody" as used herein encompasses antibodies produced in a feline; antibodies produced in non-feline animals that comprise feline immunoglobulin genes or comprise feline immunoglobulin peptides; or antibodies selected using in vitro methods, such as phage display, wherein the antibody repertoire is based on a feline immunoglobulin sequence. The term "feline antibody" denotes the genus of sequences that are feline sequences. Thus, the term is not designating the process by which the antibody was created, but the genus of sequences that are relevant.

In some embodiments, an anti-IL31 antibody comprises a feline heavy chain constant region selected from an IgG1, IgG2a, and IgG2b constant region. In some embodiments, an anti-IL31 antibody is a feline IgG1, IgG2a, or IgG2b antibody.

An "equine antibody" as used herein encompasses antibodies produced in an equine; antibodies produced in non-equine animals that comprise equine immunoglobulin genes or comprise equine immunoglobulin peptides; or antibodies selected using in vitro methods, such as phage display, wherein the antibody repertoire is based on an equine immunoglobulin sequence. The term "equine antibody" denotes the genus of sequences that are equine sequences. Thus, the term is not designating the process by which the antibody was created, but the genus of sequences that are relevant.

In some embodiments, an anti-IL31 antibody comprises an equine heavy chain constant region selected from an IgG1, IgG2, IgG3, IgG4, IgG5, IgG6 and IgG7 constant region. In some embodiments, an anti-IL31 antibody is an equine IgG1, IgG2, IgG3, IgG4, IgG5, IgG6 and IgG7 antibody.

A "caninized antibody" means an antibody in which at least one amino acid in a portion of a non-canine variable region has been replaced with the corresponding amino acid from a canine variable region. In some embodiments, a caninized antibody comprises at least one canine constant region (e.g., a γ constant region, an α constant region, a δ constant region, an ε constant region, a μ constant region, or etc.) or fragment thereof. In some embodiments, a caninized antibody is an antibody fragment, such as Fab, scFv, (Fab')$_2$, etc. The term "caninized" also denotes forms of non-canine (for example, murine) antibodies that are chimeric immunoglobulins, immunoglobulin chains, or fragments thereof (such as Fv, Fab, Fab', F(ab')$_2$ or other antigen-binding sequences of antibodies) that contain minimal sequence of non-canine immunoglobulin. Caninized antibodies can include canine immunoglobulins (recipient antibody) in which residues from a CDR of the recipient are substituted by residues from a CDR of a non-canine species (donor antibody) such as mouse, rat, or rabbit having the desired specificity, affinity, and capacity. In some instances, Fv framework region (FR) residues of the canine immunoglobulin are replaced by corresponding non-canine residues. Furthermore, the caninized antibody can comprise residues that are found neither in the recipient antibody nor in the imported CDR or framework sequences, but are included to further refine and optimize antibody performance.

In some embodiments, at least one amino acid residue in a portion of a mouse variable heavy chain or a mouse variable light chain has been replaced with the corresponding amino acid from a canine variable region. In some embodiments, the modified chain is fused to a canine constant heavy chain or a canine constant light chain. In some embodiments, an anti-IL31 antibody is a caninized antibody comprising (a) a heavy chain sequence of SEQ ID NO: 15, (b) a heavy chain sequence of SEQ ID NO: 17, (c) a heavy chain sequence of SEQ ID NO: 18, (d) a heavy chain sequence of SEQ ID NO: 19, (e) a heavy chain sequence of SEQ ID NO: 20, (f) a light chain sequence of SEQ ID NO: 16, or (g) a light chain sequence of SEQ ID NO: 21.

A "felinized antibody" means an antibody in which at least one amino acid in a portion of a non-feline variable region has been replaced with the corresponding amino acid from a feline variable region. In some embodiments, a felinized antibody comprises at least one feline constant region (e.g., a γ constant region, an α constant region, a δ constant region, an ε constant region, a μ constant region, or etc.) or fragment thereof. In some embodiments, a felinized antibody is an antibody fragment, such as Fab, scFv, (Fab')$_2$, etc. The term "felinized" also denotes forms of non-feline (for example, murine) antibodies that are chimeric immunoglobulins, immunoglobulin chains, or fragments thereof (such as Fv, Fab, Fab', F(ab')$_2$ or other antigen-binding sequences of antibodies) that contain minimal sequence of non-feline immunoglobulin. Felinized antibodies can include feline immunoglobulins (recipient antibody) in which residues from a CDR of the recipient are substituted by residues from a CDR of a non-feline species (donor antibody) such as mouse, rat, or rabbit having the desired specificity, affinity, and capacity. In some instances, Fv framework region (FR) residues of the feline immunoglobulin are replaced by corresponding non-feline residues. Furthermore, the felinized antibody can comprise residues that are found neither in the recipient antibody nor in the imported CDR or framework sequences, but are included to further refine and optimize antibody performance.

In some embodiments, at least one amino acid residue in a portion of a mouse variable heavy chain or a mouse variable light chain has been replaced with the corresponding amino acid from a feline variable region. In some embodiments, the modified chain is fused to a feline constant heavy chain or a canine constant light chain. In some embodiments, an anti-IL31 antibody is a felinized antibody comprising (a) a light chain sequence of SEQ ID NO: 32, (b) a light chain sequence of SEQ ID NO: 34, (c) a heavy chain sequence of SEQ ID NO: 33, or (d) a heavy chain sequence of SEQ ID NO: 35.

An "equinized antibody" means an antibody in which at least one amino acid in a portion of a non-equine variable region has been replaced with the corresponding amino acid from an equine variable region. In some embodiments, an equinized antibody comprises at least one equine constant region (e.g., a γ constant region, an α constant region, a δ constant region, an constant region, a μ constant region, or etc.) or fragment thereof. In some embodiments, an equinized antibody is an antibody fragment, such as Fab, scFv, (Fab')$_2$, etc. The term "equinized" also denotes forms of non-equine (for example, murine) antibodies that are chimeric immunoglobulins, immunoglobulin chains, or fragments thereof (such as Fv, Fab, Fab', F(ab')$_2$ or other antigen-binding sequences of antibodies) that contain minimal sequence of non-equine immunoglobulin. Equinized antibodies can include equine immunoglobulins (recipient antibody) in which residues from a CDR of the recipient are substituted by residues from a CDR of a non-equine species (donor antibody) such as mouse, rat, or rabbit having the desired specificity, affinity, and capacity. In some instances, Fv framework region (FR) residues of the equine immunoglobulin are replaced by corresponding non-equine residues. Furthermore, the equinized antibody can comprise residues that are found neither in the recipient antibody nor in the imported CDR or framework sequences, but are included to further refine and optimize antibody performance.

In some embodiments, at least one amino acid residue in a portion of a mouse variable heavy chain or a mouse variable light chain has been replaced with the corresponding amino acid from an equine variable region. In some embodiments, the modified chain is fused to an equine constant heavy chain or a canine constant light chain.

The term "IgX Fc" means the Fc region is derived from a particular antibody isotype (e.g., IgG, IgA, IgD, IgE, IgM, etc.), where "X" denotes the antibody isotype. Thus, "IgG Fc" denotes the Fc region of a γ chain, "IgA Fc" denotes the Fc region of an α chain, "IgD Fc" denotes the Fc region of a δ chain, "IgE Fc" denotes the Fc region of an c chain, "IgM Fc" denotes the Fc region of a μ chain, etc. In some embodiments, the IgG Fc region comprises CH1, hinge, CH2, CH3, and CL1. "IgX-N-Fc" denotes that the Fc region is derived from a particular subclass of antibody isotype (such as canine IgG subclass A, B, C, or D; feline IgG subclass 1, 2a, or 2b; or equine IgG subclass IgG1, IgG2, IgG3, IgG4, IgG5, IgG6, or IgG7, etc.), where "N" denotes the subclass. In some embodiments, IgX Fc or IgX-N-Fc regions are derived from a companion animal, such as a dog, a cat, or a horse. In some embodiments, IgG Fc regions are isolated from canine γ heavy chains, such as IgG-A, IgG-B, IgG-C, or IgG-D. In some instances, IgG Fc regions are isolated from feline γ heavy chains, such as IgG1, IgG2a, or IgG2b. Antibodies comprising an Fc region of IgG-A, IgG-B, IgG-C, or IgG-D may provide for higher expression levels in recombination production systems.

The term "affinity" means the strength of the sum total of noncovalent interactions between a single binding site of a molecule (for example, an antibody) and its binding partner (for example, an antigen). The affinity of a molecule X for its partner Y can generally be represented by the dissociation constant ($K_D$). Affinity can be measured by common methods known in the art, such as, for example, immunoblot, ELISA KD, KinEx A, biolayer interferometry (BLI), or surface plasmon resonance devices.

The terms "$K_D$," "$K_d$," "Kd" or "Kd value" as used interchangeably to refer to the equilibrium dissociation constant of an antibody-antigen interaction. In some embodiments, the $K_d$ of the antibody is measured by using biolayer interferometry assays using a biosensor, such as an Octet® System (Pall ForteBio LLC, Fremont, Calif.) according to the supplier's instructions. Briefly, biotinylated antigen is bound to the sensor tip and the association of antibody is monitored for ninety seconds and the dissociation is monitored for 600 seconds. The buffer for dilutions and binding steps is 20 mM phosphate, 150 mM NaCl, pH 7.2. A buffer only blank curve is subtracted to correct for any drift. The data are fit to a 2:1 binding model using ForteBio data analysis software to determine association rate constant ($k_{on}$), dissociation rate constant ($k_{off}$), and the $K_d$. The equilibrium dissociation constant ($K_d$) is calculated as the ratio of $k_{off}/k_{on}$. The term "kon" refers to the rate constant for association of an antibody to an antigen and the term "koff" refers to the rate constant for dissociation of an antibody from the antibody/antigen complex.

The term "binds" to an antigen or epitope is a term that is well understood in the art, and methods to determine such binding are also well known in the art. A molecule is said to exhibit "binding" if it reacts, associates with, or has affinity for a particular cell or substance and the reaction, association, or affinity is detectable by one or more methods known in the art, such as, for example, immunoblot, ELISA KD, KinEx A, biolayer interferometry (BLI), surface plasmon resonance devices, or etc.

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al. (1993) *Ann. Biol. Clin.* 51: 19-26.

"Biolayer interferometry" refers to an optical analytical technique that analyzes the interference pattern of light reflected from a layer of immobilized protein on a biosensor tip and an internal reference layer. Changes in the number of molecules bound to the biosensor tip cause shifts in the interference pattern that can be measured in real-time. A nonlimiting exemplary device for biolayer interferometry is an Octet® system (Pall ForteBio LLC). See, e.g., Abdiche et al., 2008, *Anal. Biochem.* 377: 209-277.

In some embodiments, an anti-IL31 antibody binds to canine IL31, feline IL31, or equine IL31 with a dissociation constant (Kd) of less than $5 \times 10^{-6}$ M, less than $1 \times 10^{-6}$ M, less than $5 \times 10^{-7}$ M, less than $1 \times 10^{-7}$ M, less than $5 \times 10^{-8}$ M, less than $1 \times 10^{-8}$ M, less than $5 \times 10^{-9}$ M, less than $1 \times 10^{-9}$ M, less than $5 \times 10^{-10}$ less than $1 \times 10^{-10}$ M, less than $5 \times 10^{-11}$ M, less M, than $1 \times 10^{-11}$ M, less than $5 \times 10^{-12}$ M, or less than $1 \times 10^{-12}$ M, as measured by biolayer interferometry. In some embodiments, an anti-IL31 antibody binds to canine IL31, feline IL31, or equine IL31 with a Kd of between $5 \times 10^{-6}$ M and $1 \times 10^{-6}$ M, between $5 \times 10^{-6}$ M and $5 \times 10^{-7}$ M, between $5 \times 10^{-7}$ M and $1 \times 10^{-7}$ M, between $5 \times 10^{-6}$ M and $5 \times 10^{-8}$ M, $5 \times 10^{-6}$ M and $1 \times 10^{-8}$ M, between $5 \times 10^{-6}$ M and $5 \times 10^{-9}$ M, between $5 \times 10^{-6}$ M and $1 \times 10^{-9}$ M, between $5 \times 10^{-6}$ M and $5 \times 10^{-10}$ M, between $5 \times 10^{-6}$ M and $1 \times 10^{-10}$ M, between $5 \times 10^{-6}$ M and $5 \times 10^{-11}$ M, between $5 \times 10^{-6}$ M and $1 \times 10^{-11}$ M, between $5 \times 10^{-6}$ M and $5 \times 10^{-12}$ M, between $5 \times 10^{-6}$ M and $1 \times 10^{-12}$ M, between $1 \times 10^{-6}$ M and $5 \times 10^{-7}$ M, between $1 \times 10^{-6}$ M and $1 \times 10^{-7}$ M, between $1 \times 10^{-6}$ M and $5 \times 10^{-8}$ M, $1 \times 10^{-6}$ M and $1 \times 10^{-8}$ M, between $1 \times 10^{-6}$ M and $5 \times 10^{-9}$ M, between $1 \times 10^{-6}$ M and $1 \times 10^{-9}$ M, between $1 \times 10^{-6}$ M and $5 \times 10^{-10}$ M, between $1 \times 10^{-6}$ M and $1 \times 10^{-10}$ M, between $1 \times 10^{-6}$ M and $5 \times 10^{-11}$ M, between $1 \times 10^{-6}$ M and $1 \times 10^{-11}$ M, between $1 \times 10^{-6}$ M and $5 \times 10^{-12}$ M, between $1 \times 10^{-6}$ M and $1 \times 10^{-12}$ M, between $5 \times 10^{-7}$ M and $1 \times 10^{-7}$ M, between $5 \times 10^{-7}$ M and $5 \times 10^{-8}$ M, $5 \times 10^{-7}$ M and $1 \times 10^{-8}$ M, $5 \times 10^{-7}$ M and $5 \times 10^{-9}$ M, between $5 \times 10^{-7}$ M and $1 \times 10^{-9}$ M, between $5 \times 10^{-7}$ M and $5 \times 10^{-10}$ M, between $5 \times 10^{-7}$ M and $1 \times 10^{-10}$ M, between $5 \times 10^{-7}$ M and $5 \times 10^{-11}$ M, between $5 \times 10^{-7}$ M and $1 \times 10^{-11}$ M, between $5 \times 10^{-7}$ M and $5 \times 10^{-12}$ M, between $5 \times 10^{-7}$ M and $1 \times 10^{-12}$ M, between $1 \times 10^{-7}$ M and $5 \times 10^{-8}$ M, $1 \times 10^{-7}$ M and $1 \times 10^{-8}$ M, between $1 \times 10^{-7}$ M and $5 \times 10^{-9}$ M, between $1 \times 10^{-7}$ M and $1 \times 10^{-9}$ M, between $1 \times 10^{-7}$ M and $5 \times 10^{-10}$ M, between $1 \times 10^{-7}$ M and $1 \times 10^{-10}$ M, between $1 \times 10^{-7}$ M and $5 \times 10^{-11}$ M, between $1 \times 10^{-7}$ M and $1 \times 10^{-11}$ M, between $1 \times 10^{-7}$ M and $5 \times 10^{-12}$ M, between $1 \times 10^{-7}$ M and $1 \times 10^{12}$ M, between $5 \times 10^{-8}$ M and $1 \times 10^{-8}$ M, between $5 \times 10^{-8}$ M and $5 \times 10^{-9}$ M, between $5 \times 10^{-8}$ M and $1 \times 10^{-9}$ M, between $5 \times 10^{-8}$ M and $5 \times 10^{-10}$ M, between $5 \times 10^{-8}$ M and $1 \times 10^{-10}$ M, between $5 \times 10^{-8}$ M and $5 \times 10^{-11}$ M, between $5 \times 10^{-8}$ M and $1 \times 10^{-11}$ M, between $5 \times 10^{-8}$ M and $5 \times 10^{-12}$ M, between $5 \times 10^{-8}$ M and $1 \times 10^{-12}$ M, $1 \times 10^{-8}$ M and $5 \times 10^{-9}$ M, between $1 \times 10^{-8}$ M and $1 \times 10^{-9}$ M, between $1 \times 10^{-8}$ M and $5 \times 10^{-10}$ M, between $1 \times 10^{-8}$ M and $1 \times 10^{-10}$ M, between $1 \times 10^{-8}$ M and $5 \times 10^{-11}$ M, between $1 \times 10^{-8}$ M and $1 \times 10^{-11}$ M, between $1 \times 10^{-8}$ M and $5 \times 10^{12}$ M, between $1 \times 10^{-8}$ M and $1 \times 10^{12}$ M, between $5 \times 10^{-9}$ M and $1 \times 10^{-9}$ M, between $5 \times 10^{-9}$ M and $5 \times 10^{-10}$ M, between $5 \times 10^{-9}$ M and $1 \times 10^{-10}$ M, between $5 \times 10^{-9}$ M and $5 \times 10^{-11}$ M, between $5 \times 10^{-9}$ M and $1 \times 10^{-11}$ M, between $5 \times 10^{-9}$ M and $5 \times 10^{-12}$ M, between 5×10⁻⁹ M and 1×10⁻¹² M, between 1×10⁻⁹ M and 5×10⁻¹⁰ M, between 1×10⁻⁹ M and 1×10⁻¹⁰ M, between 1×10⁻⁹ M and 5×10⁻¹¹ M, between 1×10⁻⁹ M and 1×10⁻¹¹ M, between 1×10⁻⁹ M and 5×10⁻¹² M, between 1×10⁻⁹ M and 1×10⁻¹² M, between 5×10⁻¹⁰ M and 1×10⁻¹⁰ M, between 5×10⁻¹⁰ M and 5×10⁻¹¹ M, between, 1×10⁻¹⁰ M and 5×10⁻¹¹ M, 1×10⁻¹⁰ M and 1×10⁻¹¹ M, between 1×10⁻¹⁰ M and 5×10⁻¹² M, between 1×10⁻¹⁰ M and 1×10⁻¹² M, between 5×10⁻¹¹ M and 1×10⁻¹² M, between 5×10⁻¹¹ M and 5×10⁻¹² M, between 5×10⁻¹¹ M and 1×10⁻¹² M, between 1×10⁻¹¹ M and 5×10⁻¹² M, or between 1×10⁻¹¹ M and 1×10⁻¹² M, as measured by biolayer interferometry. In some embodiments, an anti-IL31 antibody binds to canine IL31, feline IL31, or equine IL31, as determined by immunoblot analysis.

In some embodiments, an anti-IL31 antibody is provided that competes with an anti-IL31 antibody described herein (such as M14, M18, M19, or M87) for binding to IL31. In some embodiments, an antibody that competes with binding with any of the antibodies provided herein can be made or used. In some embodiments, an anti-IL31 antibody is provided that competes with monoclonal M14 antibody in binding to canine IL31, feline IL31, or equine IL31.

A "variant" means a biologically active polypeptide having at least about 50% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, deleted, at the N- or C-terminus of the polypeptide.

In some embodiments, a variant has at least about 50% amino acid sequence identity, at least about 60% amino acid sequence identity, at least about 65% amino acid sequence identity, at least about 70% amino acid sequence identity, at least about 75% amino acid sequence identity, at least about 80% amino acid sequence identity, at least about 85% amino acid sequence identity, at least about 90% amino acid sequence identity, at least about 95% amino acid sequence identity with the native sequence polypeptide.

As used herein, "percent (%) amino acid sequence identity" and "homology" with respect to a peptide, polypeptide, or antibody sequence are defined as the percentage of amino acid residues in a candidate sequence that are identical with the amino acid residues in the specific peptide or polypeptide sequence, after aligning the sequences and introducing gaps, if necessary to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALINE™ (DNASTAR) software. Those skilled in the art can determine appropriate parameters for measuring alignment, including any algorithms needed to achieve maximal alignment over the full length of sequences being compared.

An amino acid substitution may include but is not limited to the replacement of one amino acid in a polypeptide with another amino acid. Exemplary substitutions are shown in Table 2. Amino acid substitutions may be introduced into an antibody of interest and the products screened for a desired activity, for example, retained/improved antigen binding, decreased immunogenicity, or improved ADCC or CDC.

TABLE 2

| Original Residue | Exemplary Substitutions |
| --- | --- |
| Ala (A) | Val; Leu; Ile |
| Arg (R) | Lys; Gln; Asn |
| Asn (N) | Gln; His; Asp; Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes with another class.

In some embodiments, an anti-IL31 antibody comprises a heavy chain and a light chain, wherein:
a. the heavy chain comprises a CDR-H1 sequence having at least 85% sequence identity, at least 90% sequence identity, at least 95% sequence identity, or at least 98% sequence identity to the amino acid sequence of SEQ ID NO: 1; a CDR-H2 sequence having at least 85% sequence identity, at least 90% sequence identity, at least 95% sequence identity, or at least 98% sequence identity to the amino acid sequence of SEQ ID NO: 2; and a CDR-H3 sequence having at least 85% sequence identity, at least 90% sequence identity, at least 95% sequence identity, or at least 98% sequence identity to the amino acid sequence of SEQ ID NO: 3, and
b. the light chain comprises a CDR-L1 sequence having at least 85% sequence identity, at least 90% sequence identity, at least 95% sequence identity, or at least 98% sequence identity to the amino acid sequence of SEQ ID NO: 8; a CDR-L2 sequence having at least 85% sequence identity, at least 90% sequence identity, at least 95% sequence identity, or at least 98% sequence identity to the amino acid sequence of SEQ ID NO: 9; and a CDR-L3 sequence having at least 85% sequence identity, at least 90% sequence identity, at least 95% sequence identity, or at least 98% sequence identity to the amino acid sequence of SEQ ID NO: 10.

In some embodiments, an anti-IL31 antibody comprises a heavy chain and a light chain, wherein:
a. (i) a variable light chain sequence having at least 85%, at least 90%, at least 95%, or at least 98% sequence identity to the amino acid sequence of SEQ ID NO: 24; (ii) a variable heavy chain sequence having at least 85%, at least 90%, at least 95%, or at least 98% sequence identity to the amino acid sequence of SEQ ID NO: 25; or (iii) a variable light chain sequence as in (i) and a variable heavy chain sequence as in (ii); or
b. (i) a variable light chain sequence having at least 85%, at least 90%, at least 95%, or at least 98% sequence identity to the amino acid sequence of SEQ ID NO: 16; (ii) a variable heavy chain sequence having at least 85%, at least 90%, at least 95%, or at least 98% sequence identity to the amino acid sequence of SEQ ID NO: 15; or (iii) a variable light chain sequence as in (i) and a variable heavy chain sequence as in (ii); or c. (i) a variable light chain sequence having at least 85%, at least 90%, at least 95%, or at least 98% sequence identity to the amino acid sequence of SEQ ID NO: 32; (ii) a variable heavy chain sequence having at least 85%, at least 90%, at least 95%, or at least 98% sequence identity to the amino acid sequence of SEQ ID NO: 33; or (iii) a variable light chain sequence as in (i) and a variable heavy chain sequence as in (ii).

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters or enhancers) that regulate the expression of the polypeptide of interest, or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NS0 cells, PER.C6® cells (Crucell), 293 cells, and CHO cells, and their derivatives, such as 293-6E, DG44, CHO-S, and CHO-K cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) encoding an amino acid sequence(s) provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated." In some embodiments, the anti-IL31 antibody is purified using chromatography, such as size exclusion chromatography, ion exchange chromatography, protein A column chromatography, hydrophobic interaction chromatography, and CHT chromatography.

The term "companion animal species" refers to an animal suitable to be a companion to humans. In some embodiments, a companion animal species is a small mammal, such as a canine, feline, dog, cat, horse, rabbit, ferret, guinea pig, rodent, etc. In some embodiments, a companion animal species is a farm animal, such as a horse, cow, pig, etc.

The term "IL31 signaling function" refers to any one of or combination of the downstream activities that occurs when IL31 binds its receptor or receptor complex. In some embodiments, the IL31 signaling function comprises activation of Janus kinase (Jak) 1 or Jak 2 signaling molecules. In some embodiments, the IL31 signaling function comprises phosphorylation of STAT-3 or STAT-5 proteins. In some embodiments, the IL31 signaling function comprises activating the ERK1/2 MAP kinase signaling pathway. In some embodiments, the IL31 signaling function comprises activating the PI3K/AKT signaling pathway. In some embodiments, the IL31 signaling function comprises activating the Jak1/2 signaling pathway.

"STAT phosphorylation" means the post-expression modification of a STAT protein by phosphorylation. For example, "STAT-3 phosphorylation" refers to the phosphorylation of STAT-3 and "STAT-5 phosphorylation" refers to the phosphorylation of STAT-5. In some embodiments, the phosphorylation of STAT-3 is measured by immune-blot analysis. For example, cells (e.g., canine monocytic DH82 cells) are plated into a 96-well cell culture plate at a density of $1\times10^5$ cells per well in growth media (e.g., MEM, Life Technologies®) containing 15% heat-inactivated fetal bovine serum, 2 mmol/L GlutaMax, 1 mmol/L sodium pyruvate, and 10 nm/mL canine interferon-c (R&D Systems, Minneapolis, Minn., USA) for 24 hours at 37° C. in the presence of anti-IL31 antibody as described herein. Immuno-blot analysis of the cell lysate using anti-phospho STAT-3 and anti-STAT-3 antibodies (R&D Systems) were used to detect the concentration of phosphorylated STAT-3 and unphosphorylated STAT-3 relative to each other and compared to a beta-actin control. Methods for determining the concentration of proteins, either qualitatively or quantitatively, by immunoblot are understood by persons of skill in the art. In some embodiments, relative concentration is determined by qualitatively by visual inspection of the immunoblot. In some embodiments, the concentration of phosphorylated STAT-3 and unphosphorylated STAT-3 is quantitatively determined by digitally imaging an immunoblot, determining the intensity of the bands, and using a linear standard curve of known concentrations of STAT-3 protein to back calculate the concentration of phosphorylated or unphosporylated STAT-3 in a sample.

To "reduce" or "inhibit" means to decrease, reduce, or arrest an activity, function, or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time. A "reference" as used herein, refers to any sample, standard, or level that is used for comparison purposes. A reference may be obtained from a healthy or non-diseased sample. In some examples, a reference is obtained from a non-diseased or non-treated sample of a companion animal. In some examples, a reference is obtained from one or more healthy animals of a particular species, which are not the animal being tested or treated.

The term "substantially reduced," as used herein, denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 15% 20%, 25%, 30%, 35%, 40%, 45%, 50%, 60%, 70%, 80%, 90%, or 100% compared to the reference value.

In some embodiments, an IL31 antibody may reduce IL31 signaling function in a companion animal species by at least 10%, at least 15%, at least 20%, at least 25%, at least 30%, at least 35%, at least 40%, at least 45%, at least 50%, at least 60%, at least 70%, at least 80%, at least 90%, or 100% compared to IL31 signaling function in the absence of the antibody, as measured by a reduction in STAT-3 phosphorylation. In some embodiments, the reduction in IL31 signaling function or the reduction in STAT-3 phosphorylation is between 10% and 15%, between 10% and 20%, between 10% and 25%, between 10% and 30%, between 10% and 35%, between 10% and 40%, between 10% and 45%, between 10% and 50%, between 10% and 60%, between 10% and 70%, between 10% and 80%, between 10% and 90%, between 10% and 100%, between 15% and 20%, between 15% and 25%, between 15% and 30%, between 15% and 35%, between 15% and 40%, between 15% and 45%, between 15% and 50%, between 15% and 60%, between 15% and 70%, between 15% and 80%, between 15% and 90%, between 15% and 100%, between 20% and 25%, between 20% and 30%, between 20% and 35%, between 20% and 40%, between 20% and 45%, between 20% and 50%, between 20% and 60%, between 20% and 70%, between 20% and 80%, between 20% and 90%, between 20% and 100%, between 25% and 30%, between 25% and 35%, between 25% and 40%, between 25% and 45%, between 25% and 50%, between 25% and 60%, between 25% and 70%, between 25% and 80%, between 25% and 90%, between 25% and 100%, between 30% and 35%, between 30% and 40%, between 30% and 45%, between 30% and 50%, between 30% and 60%, between 30% and 70%, between 30% and 80%, between 30% and 90%, between 30% and 100%, between 35% and 40%, between 35% and 45%, between 35% and 50%, between 35% and 60%, between 35% and 70%, between 35% and 80%, between 35% and 90%, between 35% and 100%, between 40% and 45%, between 40% and 50%, between 40% and 60%, between 40% and 70%, between 40% and 80%, between 40% and 90%, between 40% and 100%, between 45% and 50%, between 45% and 60%, between 45% and 70%, between 45% and 80%, between 45% and 90%, between 45% and 100%, between 50% and 60%, between 50% and 70%, between 50% and 80%, between 50% and 90%, between 50% and 100%, between 60% and 70%, between 60% and 80%, between 60% and 90%, between 60% and 100%, between 70% and 80%, between 70% and 90%, between 70% and 100%, between 80% and 90%, between 80% and 100%, or between 90% and 100%.

Pharmaceutical Compositions

The terms "pharmaceutical formulation" and "pharmaceutical composition" refer to a preparation which is in such form as to permit the biological activity of the active ingredient(s) to be effective, and which contains no additional components that are unacceptably toxic to a subject to which the formulation would be administered.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed. Examples of pharmaceutically acceptable carriers include alumina; aluminum stearate; lecithin; serum proteins, such as human serum albumin, canine or other animal albumin; buffers such as phosphate, citrate, tromethamine or HEPES buffers; glycine; sorbic acid; potassium sorbate; partial glyceride mixtures of saturated vegetable fatty acids; water; salts or electrolytes, such as protamine sulfate, disodium hydrogen phosphate, potassium hydrogen phosphate, sodium chloride, zinc salts, colloidal silica, or magnesium trisilicate; polyvinyl pyrrolidone, cellulose-based substances; polyethylene glycol; sucrose; mannitol; or amino acids including, but not limited to, arginine.

The pharmaceutical composition can be stored in lyophilized form. Thus, in some embodiments, the preparation process includes a lyophilization step. The lyophilized composition may then be reformulated, typically as an aqueous composition suitable for parenteral administration, prior to administration to the dog, cat, or horse. In other embodiments, particularly where the antibody is highly stable to thermal and oxidative denaturation, the pharmaceutical composition can be stored as a liquid, i.e., as an aqueous composition, which may be administered directly, or with appropriate dilution, to the dog, cat, or horse. A lyophilized composition can be reconstituted with sterile Water for Injection (WFI). Bacteriostatic reagents, such benzyl alcohol, may be included. Thus, the invention provides pharmaceutical compositions in solid or liquid form.

The pH of the pharmaceutical compositions may be in the range of from about pH 5 to about pH 8, when administered. The compositions of the invention are sterile if they are to be used for therapeutic purposes. Sterility can be achieved by any of several means known in the art, including by filtration through sterile filtration membranes (e.g., 0.2 micron membranes). Sterility may be maintained with or without anti-bacterial agents.

Uses of Antibodies and Pharmaceutical Compositions

The antibodies or pharmaceutical compositions comprising the antibodies of the invention may be useful for treating an IL-31-induced condition. As used herein, an "IL31-induced condition" means a disease associated with, caused by, or characterized by, elevated levels or altered gradients of IL31 concentration. Such IL31-induced conditions include, but are not limited to, a pruritic or an allergic disease. In some embodiments, the IL31-induced condition is atopic dermatitis, pruritus, asthma, psoriasis, scleroderma, or eczema. An IL31-induced condition may be exhibited in a companion animal, including, but not limited to, canine, feline, or equine.

As used herein, "treatment" is an approach for obtaining beneficial or desired clinical results. "Treatment" as used herein, covers any administration or application of a therapeutic for disease in a mammal, including a companion animal. For purposes of this disclosure, beneficial or desired clinical results include, but are not limited to, any one or more of: alleviation of one or more symptoms, diminishment of extent of disease, preventing or delaying spread of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

In some embodiments, an anti-IL31 antibody or pharmaceutical compositions comprising it can be utilized in accordance with the methods herein to treat IL31-induced conditions. In some embodiments, an anti-IL31 antibody or pharmaceutical compositions is administered to a companion animal, such as a canine, a feline, or equine, to treat an IL31-induced condition.

A "therapeutically effective amount" of a substance/molecule, agonist or antagonist may vary according to factors such as the type of disease to be treated, the disease state, the severity and course of the disease, the type of therapeutic purpose, any previous therapy, the clinical history, the response to prior treatment, the discretion of the attending veterinarian, age, sex, and weight of the animal, and the ability of the substance/molecule, agonist or antagonist to elicit a desired response in the animal. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic or prophylactic result.

In some embodiments, an anti-IL31 antibody or pharmaceutical composition comprising an anti-IL31 antibody is administered parenterally, by subcutaneous administration, intravenous infusion, or intramuscular injection. In some embodiments, an anti-IL31 antibody or pharmaceutical composition comprising an anti-IL31 antibody is administered as a bolus injection or by continuous infusion over a period of time. In some embodiments, an anti-IL31 antibody or pharmaceutical composition comprising an anti-IL31 antibody is administered by an intramuscular, an intraperitoneal, an intracerebrospinal, a subcutaneous, an intra-arterial, an intrasynovial, an intrathecal, or an inhalation route.

Anti-IL31 antibodies described herein may be administered in an amount in the range of 0.1 mg/kg body weight to 100 mg/kg body weight per dose. In some embodiments, anti-IL31 antibodies may be administered in an amount in the range of 0.5 mg/kg body weight to 50 mg/kg body weight per dose. In some embodiments, anti-IL31 antibodies may be administered in an amount in the range of 1 mg/kg body weight to 10 mg/kg body weight per dose. In some embodiments, anti-IL31 antibodies may be administered in an amount in the range of 0.5 mg/kg body weight to 100 mg/kg body, in the range of 1 mg/kg body weight to 100 mg/kg body weight, in the range of 5 mg/kg body weight to 100 mg/kg body weight, in the range of 10 mg/kg body weight to 100 mg/kg body weight, in the range of 20 mg/kg body weight to 100 mg/kg body weight, in the range of 50 mg/kg body weight to 100 mg/kg body weight, in the range of 1 mg/kg body weight to 10 mg/kg body weight, in the range of 5 mg/kg body weight to 10 mg/kg body weight, in the range of 0.5 mg/kg body weight to 10 mg/kg body weight, or in the range of 5 mg/kg body weight to 50 mg/kg body weight.

An anti-IL31 antibody or a pharmaceutical composition comprising an anti-IL31 antibody can be administered to a companion animal at one time or over a series of treatments. For example, an anti-IL31 antibody or a pharmaceutical composition comprising an anti-IL31 antibody may be administered at least once, more than once, at least twice, at least three times, at least four times, or at least five times.

In some embodiments, the dose is administered once per week for at least two or three consecutive weeks, and in some embodiments, this cycle of treatment is repeated two or more times, optionally interspersed with one or more weeks of no treatment. In other embodiments, the therapeutically effective dose is administered once per day for two to five consecutive days, and in some embodiments, this cycle of treatment is repeated two or more times, optionally interspersed with one or more days or weeks of no treatment.

Administration "in combination with" one or more further therapeutic agents includes simultaneous (concurrent) and consecutive or sequential administration in any order. The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes. The term "sequentially" is used herein to refer to administration of two or more therapeutic agents where the administration of one or more agent(s) continues after discontinuing the administration of one or more other agent(s), or wherein administration of one or more agent(s) begins before the administration of one or more other agent(s). For example, administration of the two or more therapeutic agents are administered with a time separation of more than about a specified number of minutes. As used herein, "in conjunction with" refers to administration of one treatment modality in addition to another treatment modality. As such, "in conjunction with" refers to administration of one treatment modality before, during or after administration of the other treatment modality to the animal.

In some embodiments, the method comprises administering in combination with an anti-IL31 antibody or a pharmaceutical composition comprising an anti-IL31 antibody, a Jak inhibitor, a PI3K inhibitor, an AKT inhibitor, or a MAPK inhibitor. In some embodiments, the method comprises administering in combination with an anti-IL31 antibody or a pharmaceutical composition comprising an anti-IL31 antibody, an anti-IL17 antibody, an anti-TNFα antibody, an anti-CD20 antibody, an anti-CD19 antibody, an anti-CD25 antibody, an anti-IL4 antibody, an anti-IL13 antibody, an anti-IL23 antibody, an anti-IgE antibody, an anti-CD11α antibody, anti-IL6R antibody, anti-α4-Intergrin antibody, an anti-IL12 antibody, an anti-IL1β antibody, or an anti-BlyS antibody.

Provided herein are methods of exposing to a cell an anti-IL31 antibody or a pharmaceutical composition comprising an anti-IL31 antibody under conditions permissive for binding of the antibody to IL31. In some embodiments, the cell is exposed to the antibody or pharmaceutical composition ex vivo. In some embodiments, the cell is exposed to the antibody or pharmaceutical composition in vivo. In some embodiments, a cell is exposed to the anti-IL31 antibody or the pharmaceutical composition under conditions permissive for binding of the antibody to intracellular IL31. In some embodiments, a cell is exposed to the anti-IL31 antibody or the pharmaceutical composition under conditions permissive for binding of the antibody to extracellular IL31. In some embodiments, a cell may be exposed in vivo to the anti-IL31 antibody or the pharmaceutical composition by any one or more of the administration methods described herein, including but not limited to, intraperitoneal, intramuscular, intravenous injection into the subject. In some embodiments, a cell may be exposed ex vivo to the anti-IL31 antibody or the pharmaceutical composition by exposing the cell to a culture medium comprising the antibody or the pharmaceutical composition. In some embodiments, the permeability of the cell membrane may be affected by the use of any number of methods understood by those of skill in the art (such as electroporating the cells or exposing the cells to a solution containing calcium chloride) before exposing the cell to a culture medium comprising the antibody or the pharmaceutical composition.

In some embodiments, the binding results in a reduction of IL31 signaling function by the cell. In some embodiments, an IL31 antibody may reduce IL31 signaling function in a cell by at least 10%, at least 15%, at least 20%, at least 25%, at least 30%, at least 35%, at least 40%, at least 45%, at least 50%, at least 60%, at least 70%, at least 80%, at least 90%, or 100% compared to IL31 signaling function in the absence of the antibody, as measured by a reduction in STAT-3 phosphorylation. In some embodiments, the reduction in IL31 signaling function or the reduction in STAT-3 phosphorylation is between 10% and 15%, between 10% and 20%, between 10% and 25%, between 10% and 30%, between 10% and 35%, between 10% and 40%, between 10% and 45%, between 10% and 50%, between 10% and 60%, between 10% and 70%, between 10% and 80%, between 10% and 90%, between 10% and 100%, between 15% and 20%, between 15% and 25%, between 15% and 30%, between 15% and 35%, between 15% and 40%, between 15% and 45%, between 15% and 50%, between 15% and 60%, between 15% and 70%, between 15% and 80%, between 15% and 90%, between 15% and 100%, between 20% and 25%, between 20% and 30%, between 20% and 35%, between 20% and 40%, between 20% and 45%, between 20% and 50%, between 20% and 60%, between 20% and 70%, between 20% and 80%, between 20% and 90%, between 20% and 100%, between 25% and 30%, between 25% and 35%, between 25% and 40%, between 25% and 45%, between 25% and 50%, between 25% and 60%, between 25% and 70%, between 25% and 80%, between 25% and 90%, between 25% and 100%, between 30% and 35%, between 30% and 40%, between 30% and 45%, between 30% and 50%, between 30% and 60%, between 30% and 70%, between 30% and 80%, between 30% and 90%, between 30% and 100%, between 35% and 40%, between 35% and 45%, between 35% and 50%, between 35% and 60%, between 35% and 70%, between 35% and 80%, between 35% and 90%, between 35% and 100%, between 40% and 45%, between 40% and 50%, between 40% and 60%, between 40% and 70%, between 40% and 80%, between 40% and 90%, between 40% and 100%, between 45% and 50%, between 45% and 60%, between 45% and 70%, between 45% and 80%, between 45% and 90%, between 45% and 100%, between 50% and 60%, between 50% and 70%, between 50% and 80%, between 50% and 90%, between 50% and 100%, between 60% and 70%, between 60% and 80%, between 60% and 90%, between 60% and 100%, between 70% and 80%, between 70% and 90%, between 70% and 100%, between 80% and 90%, between 80% and 100%, or between 90% and 100%.

Provided herein are methods of using the anti-IL31 antibodies, polypeptides and polynucleotides for detection, diagnosis and monitoring of an IL31-induced condition. Provided herein are methods of determining whether a companion animal will respond to anti-IL31 antibody therapy. In some embodiments, the method comprises detecting whether the animal has cells that express IL31 using an anti-IL31 antibody. In some embodiments, the method of detection comprises contacting the sample with an antibody, polypeptide, or polynucleotide and determining whether the level of binding differs from that of a reference or comparison sample (such as a control). In some embodiments, the method may be useful to determine whether the antibodies or polypeptides described herein are an appropriate treatment for the subject animal.

In some embodiments, the sample is a biological sample. The term "biological sample" means a quantity of a substance from a living thing or formerly living thing. In some embodiments, the biological sample is a cell or cell/tissue lysate. In some embodiments, the biological sample includes, but is not limited to, blood, (for example, whole blood), plasma, serum, urine, synovial fluid, and epithelial cells.

In some embodiments, the cells or cell/tissue lysate are contacted with an anti-IL31 antibody and the binding between the antibody and the cell is determined. When the test cells show binding activity as compared to a reference cell of the same tissue type, it may indicate that the subject would benefit from treatment with an anti-IL31 antibody. In some embodiments, the test cells are from tissue of a companion animal.

Various methods known in the art for detecting specific antibody-antigen binding can be used. Exemplary immunoassays which can be conducted include fluorescence polarization immunoassay (FPIA), fluorescence immunoassay (FIA), enzyme immunoassay (EIA), nephelometric inhibition immunoassay (NIA), enzyme linked immunosorbent assay (ELISA), and radioimmunoassay (RIA). An indicator moiety, or label group, can be attached to the subject antibodies and is selected so as to meet the needs of various uses of the method which are often dictated by the availability of assay equipment and compatible immunoassay procedures. Appropriate labels include, without limitation, radionuclides (for example $^{121}$I, $^{131}$I, $^{35}$S, $^{3}$H, or $^{32}$P), enzymes (for example, alkaline phosphatase, horseradish peroxidase, luciferase, or p-glactosidase), fluorescent moieties or proteins (for example, fluorescein, rhodamine, phycoerythrin, GFP, or BFP), or luminescent moieties (for example, Qdot™ nanoparticles supplied by the Quantum Dot Corporation, Palo Alto, Calif.). General techniques to be used in performing the various immunoassays noted above are known to those of ordinary skill in the art.

For purposes of diagnosis, the polypeptide including antibodies can be labeled with a detectable moiety including but not limited to radioisotopes, fluorescent labels, and various enzyme-substrate labels know in the art. Methods of conjugating labels to an antibody are known in the art. In some embodiments, the anti-IL31 antibodies need not be labeled, and the presence thereof can be detected using a second labeled antibody which binds to the first anti-IL31 antibody. In some embodiments, the anti-IL31 antibody can be employed in any known assay method, such as competitive binding assays, direct and indirect sandwich assays, and immunoprecipitation assays. Zola, Monoclonal Antibodies: A Manual of Techniques, pp. 147-158 (CRC Press, Inc. 1987). The anti-IL31 antibodies and polypeptides can also be used for in vivo diagnostic assays, such as in vivo imaging. Generally, the antibody or the polypeptide is labeled with a radionuclide (such as $^{111}$In, $^{99}$Tc, $^{14}$C, $^{131}$I, $^{125}$I, $^{3}$H, or any other radionuclide label, including those outlined herein) so that the cells or tissue of interest can be localized using immunoscintiography. The antibody may also be used as staining reagent in pathology using techniques well known in the art.

In some embodiments, a first antibody is used for a diagnostic and a second antibody is used as a therapeutic. In some embodiments, the first and second antibodies are different. In some embodiments, the first and second antibodies can both bind to the antigen at the same time, by binding to separate epitopes.

The following examples illustrate particular aspects of the disclosure and are not intended in any way to limit the disclosure.

EXAMPLES

Example 1: Identification of Mouse Monoclonal Antibodies that Bind to Canine IL31

Canine IL31 gene encoding IL31 protein (SEQ ID NO: 22) was synthesized with poly-His tag on the C-terminal and cloned into a mammalian expression vector. The plasmid that carries canine IL31 gene was transfected to 293 cells.

The supernatant containing canine IL31 protein was collected and filtered. Canine IL31 was affinity purified using Ni-NTA column (CaptivA® Protein A Affinity Resin, Repligen).

Mouse monoclonal antibodies were identified using standard immunization using canine IL31 produced by 293 cells as immunogen. Various adjuvants were used during immunizations (Antibody Solutions, Sunnyvale, Calif.) and monoclonal antibodies were obtained through standard hybridoma technology. Enzyme linked immunosorbent assay (ELISA) was developed to screen the clones that produce IL31 binding antibodies. First canine IL31 was biotinylated and then it was introduced to streptavidin-coated wells. Immunized serum was then added to the wells followed by washing and detection with HRP-conjugated anti-mouse antibodies. The presence of canine IL31 binding antibody developed a positive signal. Over 100 ELISA positive clones were rescreened using biosensor (Forte Bio Octet). Biotinylated canine IL31 was bound to the sensor tip and hybridoma clone supernatants containing anti-canine IL31 antibodies were screened for antibodies having a slow off-rate (the rate of dissociation between antibody and ligand). The binding affinity of the top 19 candidates were measured at single concentration and reported as the equilibrium dissociation constant (Kd) after the antibody concentrations were measured by protein A titer assay using Biosensor Octet. The Kds of the 19 candidates were all less than 10 nM.

Furthermore, a cell-based functional assay described below in Example 4, was performed to assess activity of the top candidates in reducing canine IL31-mediated pSTAT signaling using canine DH82 cells. Four top clones (M14, M18, M19, and M87) were selected for further investigation.

Example 2: Identification of DNA Sequences Encoding VH and VL of Monoclonal Antibodies Hybridoma cells producing M14, M18, M19 and M87 were pelleted. RNA was extracted and oligonucleotide primers for amplifying mouse immunoglobulin (Ig) variable domains were used to obtain cDNA using standard techniques. The variable heavy chain (VH) and variable light chain (VL) of each of the four clones were sequenced and analyzed by sequence alignment (FIG. 1).

Example 3: Expression and Purification of Murine-Canine Chimeric and Caninized IL31-mAb M14 from CHO Cells DNA sequences encoding a chimeric antibody were designed for a fusion of murine M14 VH (SEQ ID NO: 25) and murine VL (SEQ ID NO: 24) to canine constant heavy chain and canine constant light chain. The nucleotide sequences were synthesized chemically and inserted into an expression vector suitable for transfection into a CHO host cell. After transfection into CHO cells, the light chain or heavy chain protein or both were secreted from the cell. For example, chimeric M14 that uses canine IgG-B was purified by single step Protein A column chromatography.

Murine M14 VH and VL were caninized by searching and selecting proper canine germline antibody sequences as a template for CDR grafting, followed by protein modeling. Caninized M14 IgG-B (SEQ ID NO: 18 and SEQ ID NO: 21) was readily expressed and purified in a single step with a protein A column or other chromatographic methods, such as ion exchange column chromatography, hydrophobic interaction column chromatography, mixed mode column chromatography such as CHT, or multimodal mode column chromatography such as CaptoMMC. Low pH or other viral inactivation and viral removal steps can be applied. The purified protein is admixed with excipients, and sterilized by filtration to prepare a pharmaceutical composition of the invention. The pharmaceutical composition is administered to a dog with an atopic dermatitis in an amount sufficient to bind to inhibit IL31.

The vectors were then used to perform pilot-scale transfection in CHO-S cells using the FreestyleMax™ transfection reagent (Life Technologies). The supernatant was harvested by clarifying the conditioned media. Protein was purified with a single pass Protein A chromatography step and used for further investigation.

Example 4: Demonstration of IL31 Binding Activity

This example demonstrates that antibodies of the invention, illustrated with the chimeric M14 (SEQ ID NO:26 and SEQ ID NO:27) and caninized M14 (SEQ ID NO:18 and SEQ ID NO:21) bind canine IL31 with kinetics requisite for therapeutic activity.

The binding analysis was performed using a biosensor Octet as follows. Briefly, canine IL31 was biotinylated. The free unreacted biotin was removed from biotinylated IL31 by extensive dialysis. Biotinylated canine IL31 was captured on streptavidin sensor tips. The association of four different concentrations (400, 200, 66.6, and 33 nM) of antibody and IL31 (human and canine, in different tests) was monitored for ninety seconds. Dissociation was monitored for 600 seconds. A buffer only blank curve was subtracted to correct for any drift. The data were fit to a 2:1 binding model using ForteBio™ data analysis software to determine the $k_{on}$, $k_{off}$, and the Kd. The buffer for dilutions and all binding steps was: 20 mM phosphate, 150 mM NaCl, pH 7.2.

Canine IL31 with C-terminal polyHis tag was expressed and purified from CHO-S cells. Human IL31 was obtained from Sino Biological, EZ-Link NHS-LC-biotin was obtained from Thermo Scientific (Cat. #21336), and Streptavidin biosensors was obtained from ForteBio (Cat. #18-509).

Figure 2B:
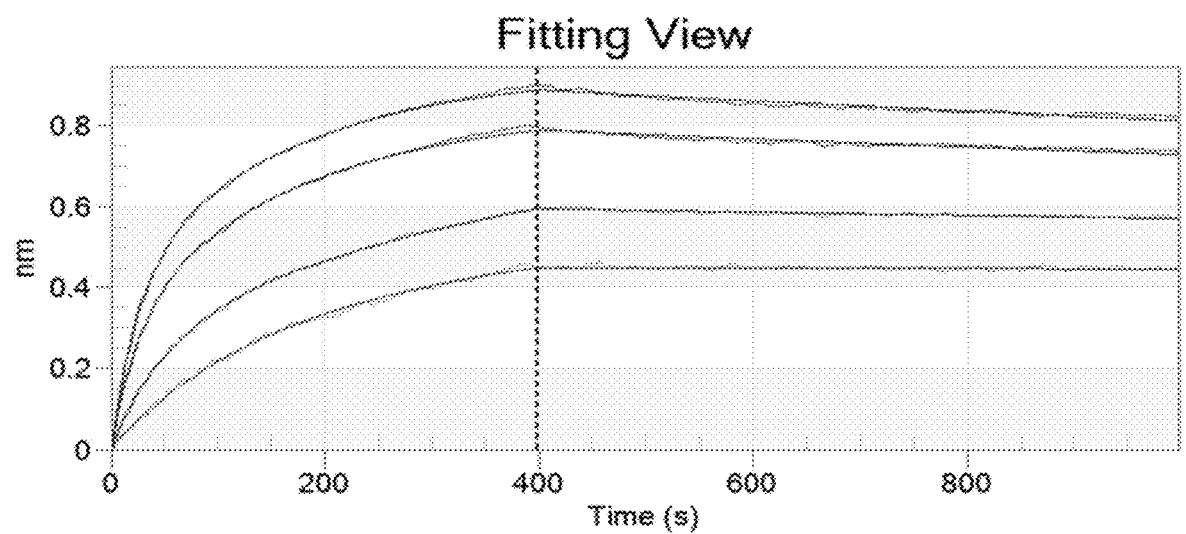
Figure 3A:
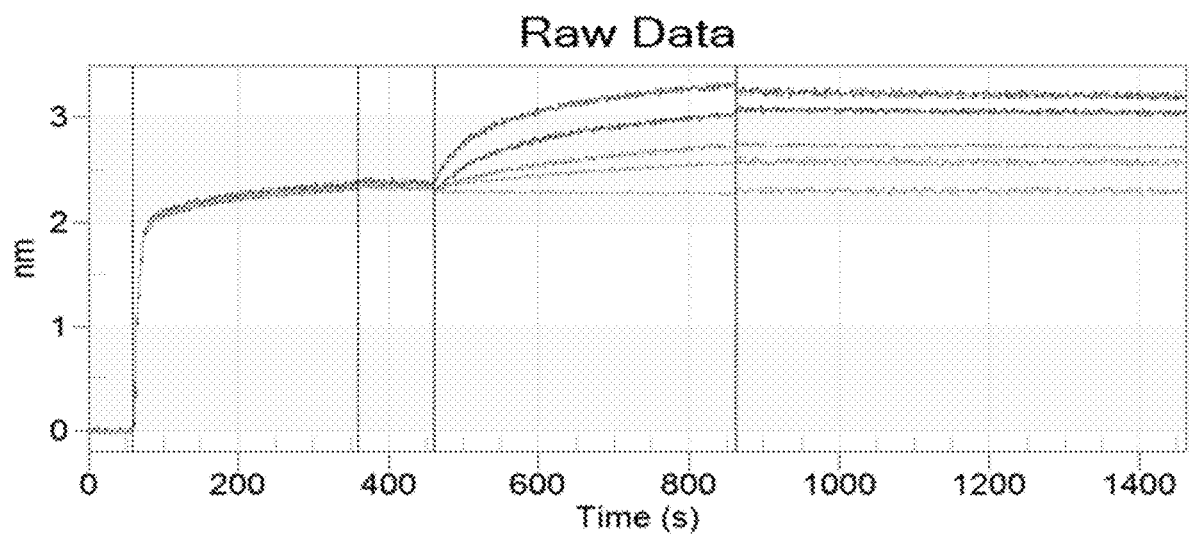
FIG. 3A and FIG. 3B are graphs of canine IL31 binding analysis with varying concentrations of caninized M14 antibody.
Figure 3B:
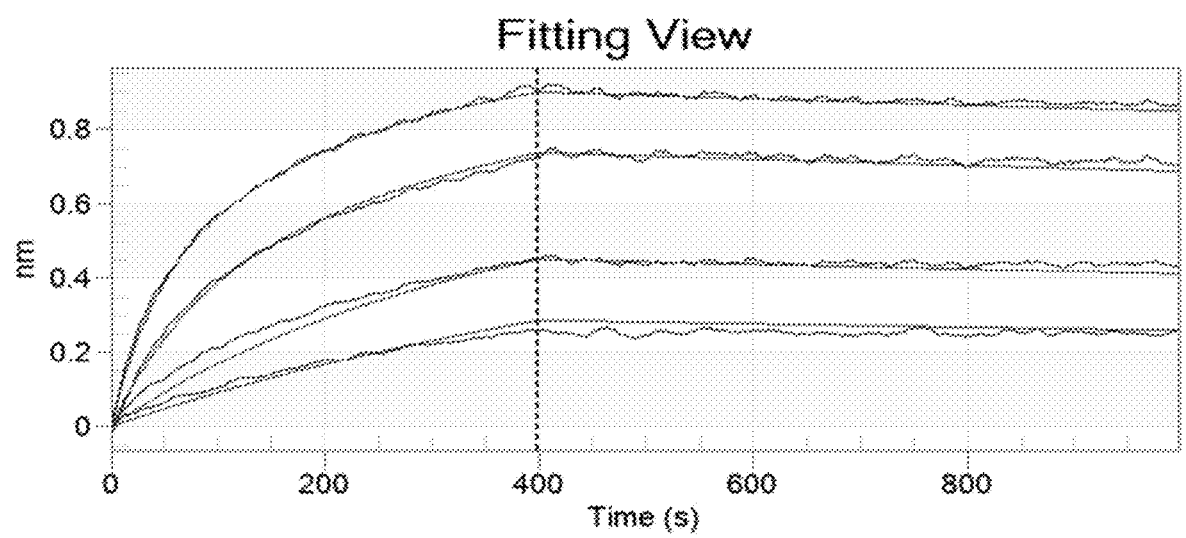

The binding kinetics were as follows: For the ligand canine IL31, the Kd (M) for chimeric M14 was $<1.0\times10^{-11}$ (FIG. 2) and $<1.0\times10^{-11}$ (FIG. 3) for caninized M14.

Chimeric M14 and caninized M14 had no obvious binding signal with human IL31. Thus the Kd could not be measured.

Example 5: Demonstration that M14 Inhibits Canine IL31 Signaling

Figure 4:
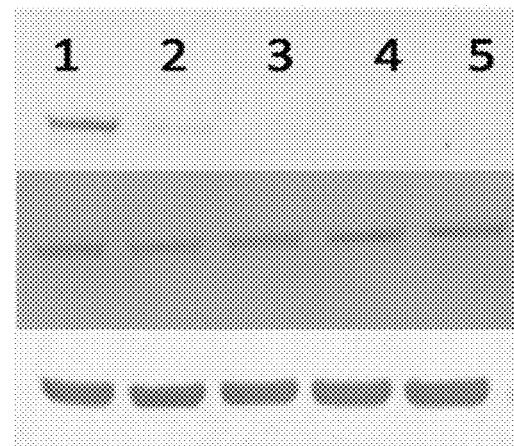
FIG. 4 is an immunoblot showing inhibited canine IL31 signaling at varying concentrations of caninized M14 antibody.

After binding to its IL31 receptor, IL-31 activates Janus kinase (Jak) 1 and Jak2 signaling molecules. In turn, activated Jaks stimulate the phosphorylation of downstream signaling STAT-3 and STAT-5. Anti-phospho-Stat3 immunoblot analysis was used to detect anti-IL31 activity from a protein A-purified fraction of cell-free culture medium (Gonzales et. al. Vet Dermatol 2013; 24: 48-e12). In Brief, the canine monocytic DH82 cells (American Type Culture Collection, Manassas, Va., USA) were plated into 96-well flat-bottomed cell culture plates at a density of $1 \times 10^5$ cells per well in MEM growth media (Life Technologies) containing 15% heat-inactivated fetal bovine serum, 2 mmol/L GlutaMax, 1 mmol/L sodium pyruvate, and 10 ng/mL canine interferon-c (R&D Systems, Minneapolis, Minn., USA) for 24 h at 37° C. In this experiment, concentration of canine IL31-Fc was 5 ng/mL (8 nM). Anti-phospho STAT-3 and anti-STAT-3 antibodies were purchased from R&D Systems. Anti-beta actin antibody was from Sigma-Aldrich. As shown in FIG. 4, canine IL31 signaling decreased (as evidenced by a reduction in STAT-3 phosphorylation) as the concentration of caninized M14 exposed to the cells increased (lane 1: no anti-IL31 antibody; Lane 2: 3.3 nM; Lane 3: 6.6 nM; Lane 4: 9.9 nM; and Lane 5: 13.2 nM).

Example 6: Identification of M14 Canine IL31 Binding Epitope

To identify the canine IL31 epitope recognized by M14, multiple GST canine IL31 fragment fusion molecules were generated and proteins were expressed intracellularly in *E. coli*. After the GST fusion proteins were transferred to a membrane, chimeric M14 was used to probe the membrane. A positive signal resulted when the IL31 fragment contained the epitope.

Figure 5A:
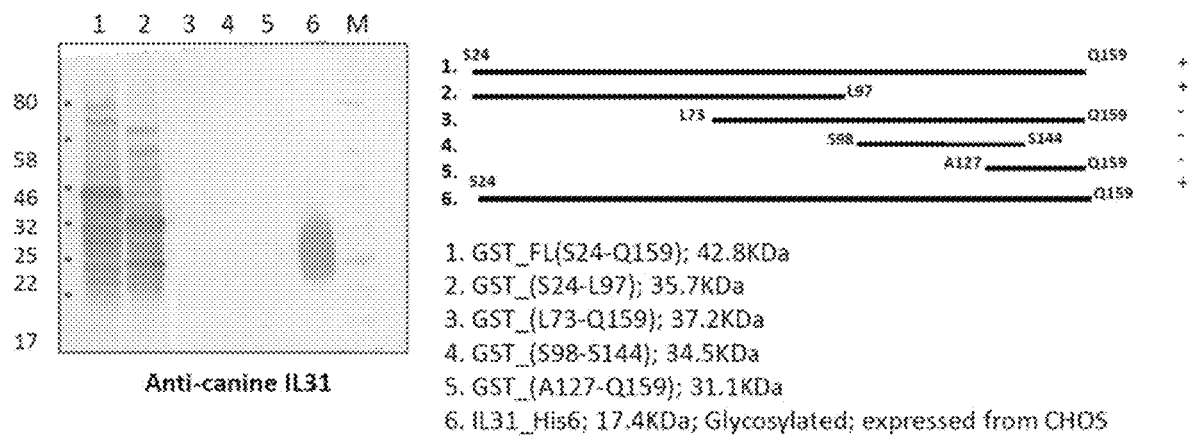
FIGS. 5A and 5B are immunoblots of GST-canine-IL31 deletions probed with M14 antibody and anti-GST antibody, respectively.
Figure 5B:
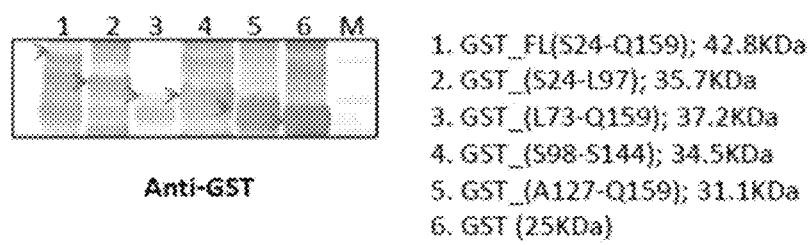
Figure 6A:
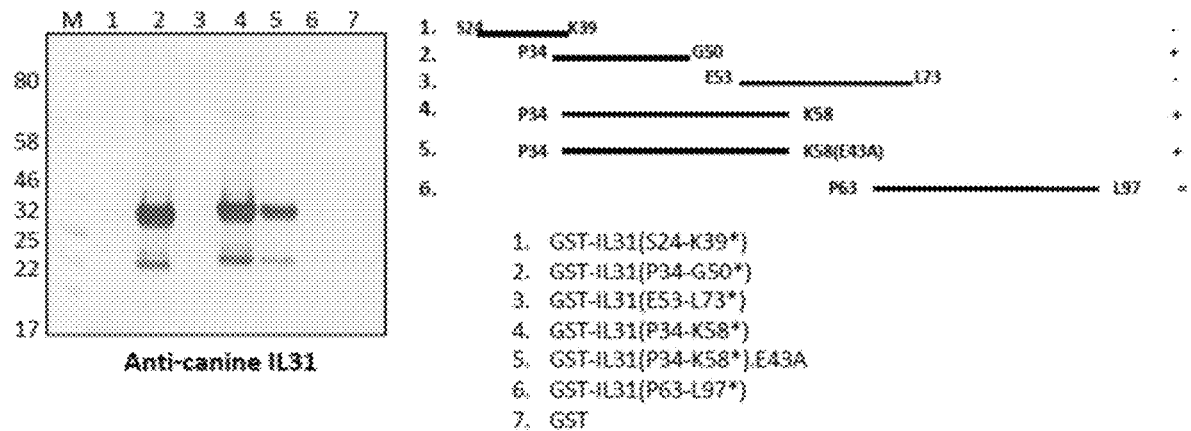
FIGS. 6A and 6B are immunoblots of GST-canine-IL31 deletions probed with M14 antibody and anti-GST antibody, respectively.
Figure 6B:
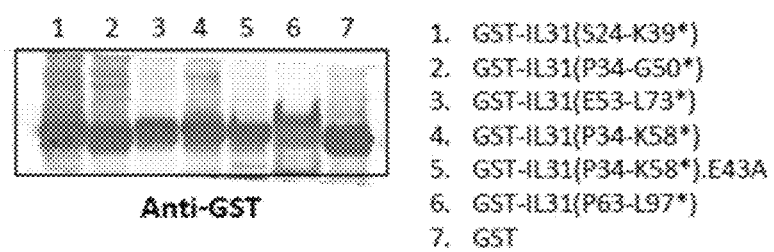

FIG. 5 combined with FIG. 6 demonstrated M14 can recognize the minimal fragment (SEQ ID NO: 23).

Example 7: Demonstrating M14 Cross Reacts to Feline IL31

To examine whether M14 antibody recognizes feline IL31 (SEQ ID NO: 28) or equine IL31 (SEQ ID NO: 29), each protein was fused to human Fc and expressed in mammalian 293 cells. The partially purified proteins were blotted to membrane and probed with M14 antibody. The immunoblot of FIG. 1 demonstrates that M14 binds to feline IL31. The immunoblot assay did not detect binding between M14 and equine IL31. However, biolayer interferometry analysis revealed that M14 antibody binds equine IL31, but with a lesser affinity. The preliminary Kd measurement using biotinylated equine IL31 immobilized to the sensor revealed that the affinity (Kd) is approximately 10 to 50 nM.

Example 8: Felinized M14

M14 variable light chain was felinized as (SEQ ID NO: 32) and M14 variable heavy chain was felinized as (SEQ ID NO: 33). First, the mouse heavy chain variable and light chain variable sequences were used to search proper variants of feline VH and VL. The proper feline frames were chosen to graft CDRs. They are further optimized using structural modeling. The felinized VH and VL were fused to a feline IgG heavy chain constant domains (CH1, CH2, and CH3) and feline light chain constant domain (CL1).

Feline M14 chimeric antibody (SEQ ID NO: 30 and SEQ ID NO: 31) or felinized M14 antibody (SEQ ID NO: 34 and SEQ ID NO: 35) can be as administered to cats for treatment of an IL31-induced condition.

The invention claimed is:

1. An isolated nucleic acid encoding an antibody that binds to canine IL31, wherein the antibody comprises (a) CDR-H1 comprising the amino acid sequence of SEQ ID NO: 1; (b) CDR-H2 comprising the amino acid sequence of SEQ ID NO: 2; (c) CDR-H3 comprising the amino acid sequence of SEQ ID NO: 3; (d) CDR-L1 comprising the amino acid sequence of SEQ ID NO: 8; (e) CDR-L2 comprising the amino acid sequence of SEQ ID NO: 9; and (f) CDR-L3 comprising the amino acid sequence of SEQ ID NO: 10.

2. An isolated host cell comprising the nucleic acid of claim 1.

3. A method of producing an antibody comprising culturing the host cell of claim 2 and isolating the antibody.

4. The isolated nucleic acid of claim 1, wherein the antibody binds to canine IL31 with a dissociation constant (Kd) of less than $5 \times 10^{-11}$ M, as measured by biolayer interferometry.

5. The isolated nucleic acid of claim 1, wherein the antibody is an antibody fragment selected from Fv, scFv, Fab, Fab', F(ab')2, and Fab'-SH.

6. The isolated nucleic acid of claim 1, wherein the antibody is a caninized, a felinized, or a chimeric antibody.

7. The isolated nucleic acid of claim 1, wherein the antibody further comprises one or more of (a) a variable region heavy chain framework 1 (HC-FR1) sequence of SEQ ID NO: 4; (b) a HC-FR2 sequence of SEQ ID NO: 5; (c) a HC-FR3 sequence of SEQ ID NO: 6; (d) a HC-FR4 sequence of SEQ ID NO: 7; (e) a variable region light chain framework 1 (LC-FR1) sequence of SEQ ID NO: 11; (f) an LC-FR2 sequence of SEQ ID NO: 12; (g) an LC-FR3 sequence of SEQ ID NO: 13; or (h) an LC-FR4 sequence of SEQ ID NO: 14.

8. The isolated nucleic acid of claim 1, wherein the antibody comprises:
   a) (i) a variable light chain sequence having at least 95% sequence identity to the amino acid sequence of SEQ ID NO: 24; (ii) a variable heavy chain sequence having at least 95% sequence identity to the amino acid sequence of SEQ ID NO: 25; or (iii) a variable light chain sequence as in (i) and a variable heavy chain sequence as in (ii); or
   b) (i) a variable light chain sequence having at least 95% sequence identity to the amino acid sequence of SEQ ID NO: 16; (ii) a variable heavy chain sequence having at least 95% sequence identity to the amino acid sequence of SEQ ID NO: 15; or (iii) a variable light chain sequence as in (i) and a variable heavy chain sequence as in (ii).

9. The isolated nucleic acid of claim 1, wherein the antibody comprises:
   a) (i) a variable light chain amino acid sequence of SEQ ID NO: 24; (ii) a variable heavy chain amino acid sequence of SEQ ID NO: 25; or (iii) a variable light chain sequence as in (i) and a variable heavy chain sequence as in (ii); or
   b) (i) a variable light chain amino acid sequence of SEQ ID NO: 16; (ii) a variable heavy chain amino acid sequence of SEQ ID NO: 15; or (iii) a variable light chain sequence as in (i) and a variable heavy chain sequence as in (ii).

10. The isolated nucleic acid of claim 1, wherein the antibody comprises:
    a) a canine heavy chain constant region selected from an IgG-A, IgG-B, IgG-C, and IgG-D constant region; or
    b) a feline heavy chain constant region selected from an IgG1, IgG2a, and IgG2b constant region.

11. The isolated nucleic acid of claim 1, wherein the antibody comprises:
    a) (i) a light chain amino acid sequence of SEQ ID NO: 26; (ii) a heavy chain amino acid sequence of SEQ ID NO: 27; or (iii) a light chain sequence as in (i) and a heavy chain sequence as in (ii); or
    b) (i) a light chain amino acid sequence of SEQ ID NO: 30; (ii) a heavy chain amino acid sequence of SEQ ID NO: 31; or (iii) a light chain amino acid sequence as in (i) and a heavy chain amino acid sequence as in (ii).

12. The isolated nucleic acid of claim 1, wherein the antibody comprises: (i) a light chain amino acid sequence of SEQ ID NO: 21; (ii) a heavy chain amino acid sequence of SEQ ID NO: 17, SEQ ID NO: 18, SEQ ID NO: 19, or SEQ ID NO: 20; or (iii) a light chain sequence as in (i) and a heavy chain sequence as in (ii).

13. The isolated nucleic acid of claim 1, wherein the antibody comprises:
    a) a variable light chain sequence of SEQ ID NO: 24 and a variable heavy chain sequence of SEQ ID NO: 25; or
    b) a variable light chain sequence of SEQ ID NO: 16 and a variable heavy chain sequence of SEQ ID NO: 15.

14. The isolated nucleic acid of claim 13, wherein the antibody comprises a canine heavy chain constant region selected from an IgG-A, IgG-B, IgG-C, and IgG-D constant region.

15. The isolated nucleic acid of claim 1, wherein the antibody comprises a light chain amino acid sequence of SEQ ID NO: 21 and a heavy chain amino acid sequence of SEQ ID NO: 17.

16. The isolated nucleic acid of claim 1, wherein the antibody comprises a light chain amino acid sequence of SEQ ID NO: 21 and a heavy chain amino acid sequence of SEQ ID NO: 18.

17. The isolated nucleic acid of claim 1, wherein the antibody comprises a light chain amino acid sequence of SEQ ID NO: 21 and a heavy chain amino acid sequence of SEQ ID NO: 19.

18. The isolated nucleic acid of claim 1, wherein the antibody comprises a light chain amino acid sequence of SEQ ID NO: 21 and a heavy chain amino acid sequence of SEQ ID NO: 20.

19. An isolated nucleic acid encoding an antibody that binds to canine IL31, wherein the antibody comprises a variable light chain amino acid sequence of SEQ ID NO: 16 and a variable heavy chain amino acid sequence of SEQ ID NO: 15.

20. An isolated nucleic acid encoding an antibody that binds to canine IL31, wherein the antibody comprises a light chain amino acid sequence of SEQ ID NO: 21 and a heavy chain amino acid sequence of SEQ ID NO: 17, SEQ ID NO: 18, SEQ ID NO: 19, or SEQ ID NO: 20.

* * * * *

SEQUENCE LISTING

```
<160> NUMBER OF SEQ ID NOS: 43

<210> SEQ ID NO 1
<211> LENGTH: 9
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(9)
<223> OTHER INFORMATION: Variable heavy chain CDR-H1 amino acid sequence
      of mouse antibody clone M14

<400> SEQUENCE: 1

Gly Asp Ser Ile Thr Ser Gly Tyr Trp
1               5

<210> SEQ ID NO 2
<211> LENGTH: 16
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(16)
<223> OTHER INFORMATION: Variable heavy chain CDR-H2 amino acid sequence
```

-continued of mouse antibody clone M14

<400> SEQUENCE: 2

Tyr Ile Ser Tyr Ser Gly Ile Thr Asp Tyr Asn Pro Ser Leu Lys Ser
1               5                   10                  15

<210> SEQ ID NO 3
<211> LENGTH: 12
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(12)
<223> OTHER INFORMATION: Variable heavy chain CDR-H3 amino acid sequence
      of mouse antibody clone M14

<400> SEQUENCE: 3

Ala Arg Tyr Gly Asn Tyr Gly Tyr Ala Met Asp Tyr
1               5                   10

<210> SEQ ID NO 4
<211> LENGTH: 25
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(25)
<223> OTHER INFORMATION: Variable region heavy chain framework HC-FR1
      amino acid sequence of mouse antibody clone M14

<400> SEQUENCE: 4

Glu Val Gln Leu Gln Glu Ser Gly Pro Ser Leu Val Lys Pro Ser Gln
1               5                   10                  15

Thr Leu Ser Leu Thr Cys Ser Val Thr
            20                  25

<210> SEQ ID NO 5
<211> LENGTH: 15
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(15)
<223> OTHER INFORMATION: Variable region heavy chain framework HC-FR2
      amino acid sequence of mouse antibody clone M14

<400> SEQUENCE: 5

Asn Trp Ile Arg Lys Phe Pro Gly Asn Lys Leu Glu Tyr Met Gly
1               5                   10                  15

<210> SEQ ID NO 6
<211> LENGTH: 30
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(30)
<223> OTHER INFORMATION: Variable region heavy chain framework HC-FR3
      amino acid sequence of mouse antibody clone M14

<400> SEQUENCE: 6

-continued

Arg Ile Ser Ile Thr Arg Asp Thr Ser Lys Asn Gln Tyr Tyr Leu Gln
1               5                   10                  15

Leu Asn Ser Val Thr Thr Glu Asp Thr Ala Thr Tyr Tyr Cys
                20                  25                  30

<210> SEQ ID NO 7
<211> LENGTH: 11
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(11)
<223> OTHER INFORMATION: Variable region heavy chain framework HC-FR4
      amino acid sequence of mouse antibody clone M14

<400> SEQUENCE: 7

Trp Gly Gln Gly Thr Ser Val Thr Val Ser Ser
1               5                   10

<210> SEQ ID NO 8
<211> LENGTH: 15
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(15)
<223> OTHER INFORMATION: Variable light chain CDR-L1 amino acid sequence
      of mouse antibody clone M14

<400> SEQUENCE: 8

Arg Ala Ser Glu Ser Val Asp Thr Tyr Gly Asn Ser Phe Met His
1               5                   10                  15

<210> SEQ ID NO 9
<211> LENGTH: 7
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(7)
<223> OTHER INFORMATION: Variable light chain CDR-L2 amino acid sequence
      of mouse antibody clone M14

<400> SEQUENCE: 9

Arg Ala Ser Asn Leu Glu Ser
1               5

<210> SEQ ID NO 10
<211> LENGTH: 9
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(9)
<223> OTHER INFORMATION: Variable light chain CDR-L3 amino acid sequence
      of mouse antibody clone M14

<400> SEQUENCE: 10

Gln Gln Ser Tyr Glu Asp Pro Trp Thr
1               5

```
<210> SEQ ID NO 11
<211> LENGTH: 23
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(23)
<223> OTHER INFORMATION: Variable region light chain framework LC-FR1
      amino acid sequence of mouse antibody clone M14

<400> SEQUENCE: 11

Asp Ile Val Leu Thr Gln Ser Pro Ala Ser Leu Ala Val Ser Leu Gly
1               5                   10                  15

Gln Arg Ala Thr Ile Ser Cys
            20

<210> SEQ ID NO 12
<211> LENGTH: 15
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(15)
<223> OTHER INFORMATION: Variable region light chain framework LC-FR2
      amino acid sequence of mouse antibody clone M14

<400> SEQUENCE: 12

Trp Tyr Gln Gln Lys Ser Gly Gln Ser Pro Lys Leu Leu Ile Tyr
1               5                   10                  15

<210> SEQ ID NO 13
<211> LENGTH: 32
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(32)
<223> OTHER INFORMATION: Variable region light chain framework LC-FR3
      amino acid sequence of mouse antibody clone M14

<400> SEQUENCE: 13

Gly Ile Pro Ala Arg Phe Gly Gly Ser Gly Ser Arg Thr Asp Phe Thr
1               5                   10                  15

Leu Thr Ile Asp Pro Val Glu Ala Asp Asp Val Ala Thr Tyr Tyr Cys
            20                  25                  30

<210> SEQ ID NO 14
<211> LENGTH: 10
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(10)
<223> OTHER INFORMATION: Variable region light chain framework LC-FR4
      amino acid sequence of mouse antibody clone M14

<400> SEQUENCE: 14

Phe Gly Gly Gly Thr Lys Leu Glu Ile Lys
1               5                   10

<210> SEQ ID NO 15
```

<211> LENGTH: 118
<212> TYPE: PRT
<213> ORGANISM: Artificial Sequence
<220> FEATURE:
<223> OTHER INFORMATION: Synthetic: Caninized variable heavy chain amino
      acid sequence of mouse antibody clone M14

<400> SEQUENCE: 15

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Leu Val Thr Val Ser Ser
        115

<210> SEQ ID NO 16
<211> LENGTH: 111
<212> TYPE: PRT
<213> ORGANISM: Artificial Sequence
<220> FEATURE:
<223> OTHER INFORMATION: Synthetic: Caninized variable light chain amino
      acid sequence of mouse antibody clone M14

<400> SEQUENCE: 16

Asp Ile Val Met Thr Gln Ser Pro Ala Ser Leu Ser Val Ser Leu Gly
1               5                   10                  15

Gln Arg Ala Thr Ile Ser Cys Arg Ala Ser Glu Ser Val Asp Thr Tyr
            20                  25                  30

Gly Asn Ser Phe Met His Trp Tyr Gln Gln Lys Pro Gly Gln Ser Pro
        35                  40                  45

Lys Leu Leu Ile Tyr Arg Ala Ser Asn Leu Glu Ser Gly Ile Pro Ala
    50                  55                  60

Arg Phe Gly Gly Ser Gly Ser Gly Thr Asp Phe Thr Leu Thr Ile Asp
65                  70                  75                  80

Pro Val Gln Ala Asp Asp Val Ala Thr Tyr Tyr Cys Gln Gln Ser Tyr
                85                  90                  95

Glu Asp Pro Trp Thr Phe Gly Gly Gly Thr Lys Leu Glu Ile Lys
            100                 105                 110

<210> SEQ ID NO 17
<211> LENGTH: 448
<212> TYPE: PRT
<213> ORGANISM: Artificial Sequence
<220> FEATURE:
<223> OTHER INFORMATION: Synthetic: Caninized heavy chain sequence from
      mouse antibody clone M14 and canine IgG-A

<400> SEQUENCE: 17

Glu Val Gln Leu Val Glu Ser Gly Pro Ser Leu Val Lys Pro Gly Gly
1               5                   10                  15

```
Ser Leu Arg Leu Thr Cys Ser Val Thr Gly Asp Ser Ile Thr Ser Gly
         20                  25                  30

Tyr Trp Asn Trp Ile Arg Lys Phe Pro Gly Asn Lys Leu Glu Tyr Met
             35                  40                  45

Gly Tyr Ile Ser Tyr Ser Gly Ile Thr Asp Tyr Asn Pro Ser Leu Lys
        50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                 85                  90                  95

Arg Tyr Gly Asn Tyr Gly Tyr Ala Met Asp Tyr Trp Gly Gln Gly Thr
            100                 105                 110

Leu Val Thr Val Ser Ser Ala Ser Thr Thr Ala Pro Ser Val Phe Pro
        115                 120                 125

Leu Ala Pro Ser Cys Gly Ser Thr Ser Gly Ser Thr Val Ala Leu Ala
        130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu His Ser Leu Ser Ser Met Val Thr Val Pro Ser Ser
            180                 185                 190

Arg Trp Pro Ser Glu Thr Phe Thr Cys Asn Val Val His Pro Ala Ser
        195                 200                 205

Asn Thr Lys Val Asp Lys Pro Val Phe Asn Glu Cys Arg Cys Thr Asp
210                 215                 220

Thr Pro Cys Pro Val Pro Glu Pro Leu Gly Gly Pro Ser Val Leu Ile
225                 230                 235                 240

Phe Pro Pro Lys Pro Lys Asp Ile Leu Arg Ile Thr Arg Thr Pro Glu
                245                 250                 255

Val Thr Cys Val Val Leu Asp Leu Gly Arg Glu Asp Pro Glu Val Gln
            260                 265                 270

Ile Ser Trp Phe Val Asp Gly Lys Glu Val His Thr Ala Lys Thr Gln
        275                 280                 285

Ser Arg Glu Gln Gln Phe Asn Gly Thr Tyr Arg Val Val Ser Val Leu
290                 295                 300

Pro Ile Glu His Gln Asp Trp Leu Thr Gly Lys Glu Phe Lys Cys Arg
305                 310                 315                 320

Val Asn His Ile Asp Leu Pro Ser Pro Ile Glu Arg Thr Ile Ser Lys
                325                 330                 335

Ala Arg Gly Arg Ala His Lys Pro Ser Val Tyr Val Leu Pro Pro Ser
            340                 345                 350

Pro Lys Glu Leu Ser Ser Ser Asp Thr Val Ser Ile Thr Cys Leu Ile
        355                 360                 365

Lys Asp Phe Tyr Pro Pro Asp Ile Asp Val Glu Trp Gln Ser Asn Gly
        370                 375                 380

Gln Gln Glu Pro Glu Arg Lys His Arg Met Thr Pro Pro Gln Leu Asp
385                 390                 395                 400

Glu Asp Gly Ser Tyr Phe Leu Tyr Ser Lys Leu Ser Val Asp Lys Ser
                405                 410                 415

Arg Trp Gln Gln Gly Asp Pro Phe Thr Cys Ala Val Met His Glu Thr
        420                 425                 430

Leu Gln Asn His Tyr Thr Asp Leu Ser Leu Ser His Ser Pro Gly Lys
```

<210> SEQ ID NO 18
<211> LENGTH: 453
<212> TYPE: PRT
<213> ORGANISM: Artificial Sequence
<220> FEATURE:
<223> OTHER INFORMATION: Synthetic: Caninized heavy chain sequence from mouse antibody clone M14 and canine IgG-B

<400> SEQUENCE: 18

```
Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Leu Val Thr Val Ser Ser Ala Ser Thr Thr Ala Pro Ser Val Phe Pro
        115                 120                 125

Leu Ala Pro Ser Cys Gly Ser Thr Ser Gly Ser Thr Val Ala Leu Ala
    130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Ser
        195                 200                 205

Lys Thr Lys Val Asp Lys Pro Val Pro Lys Arg Glu Asn Gly Arg Val
    210                 215                 220

Pro Arg Pro Pro Asp Cys Pro Lys Cys Pro Ala Pro Glu Met Leu Gly
225                 230                 235                 240

Gly Pro Ser Val Phe Ile Phe Pro Pro Lys Pro Lys Asp Thr Leu Leu
                245                 250                 255

Ile Ala Arg Thr Pro Glu Val Thr Cys Val Val Val Asp Leu Asp Pro
            260                 265                 270

Glu Asp Pro Glu Val Gln Ile Ser Trp Phe Val Asp Gly Lys Gln Met
        275                 280                 285

Gln Thr Ala Lys Thr Gln Pro Arg Glu Glu Gln Phe Asn Gly Thr Tyr
    290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Ala Leu Pro Ser Pro Ile
                325                 330                 335

Glu Arg Thr Ile Ser Lys Ala Arg Gly Gln Ala His Gln Pro Ser Val
            340                 345                 350
```

Tyr Val Leu Pro Pro Ser Arg Glu Glu Leu Ser Lys Asn Thr Val Ser
            355                 360                 365

Leu Thr Cys Leu Ile Lys Asp Phe Phe Pro Pro Asp Ile Asp Val Glu
    370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
            405                 410                 415

Ser Val Asp Lys Ser Arg Trp Gln Arg Gly Asp Thr Phe Ile Cys Ala
            420                 425                 430

Val Met His Glu Ala Leu His Asn His Tyr Thr Gln Glu Ser Leu Ser
            435                 440                 445

His Ser Pro Gly Lys
    450

<210> SEQ ID NO 19
<211> LENGTH: 451
<212> TYPE: PRT
<213> ORGANISM: Artificial Sequence
<220> FEATURE:
<223> OTHER INFORMATION: Synthetic: Caninized heavy chain sequence from
      mouse antibody clone M14 and canine IgG-C

<400> SEQUENCE: 19

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
            85                  90                  95

Arg Tyr Gly Asn Tyr Gly Tyr Ala Met Asp Tyr Trp Gly Gln Gly Thr
            100                 105                 110

Leu Val Thr Val Ser Ser Ala Ser Thr Thr Ala Pro Ser Val Phe Pro
        115                 120                 125

Leu Ala Pro Ser Cys Gly Ser Gln Ser Gly Ser Thr Val Ala Leu Ala
    130                 135                 140

Cys Leu Val Ser Gly Tyr Ile Pro Glu Pro Val Thr Val Ser Trp Asn
145                 150                 155                 160

Ser Val Ser Leu Thr Ser Gly Val His Thr Phe Pro Ser Val Leu Gln
            165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Thr
        195                 200                 205

Asn Thr Lys Val Asp Lys Pro Val Ala Lys Glu Cys Glu Cys Lys Cys
    210                 215                 220

Asn Cys Asn Asn Cys Pro Cys Pro Gly Cys Gly Leu Leu Gly Gly Pro
225                 230                 235                 240

Ser Val Phe Ile Phe Pro Pro Lys Pro Lys Asp Ile Leu Val Thr Ala
            245                 250                 255

```
Arg Thr Pro Thr Val Thr Cys Val Val Asp Leu Asp Pro Glu Asn
            260                 265                 270

Pro Glu Val Gln Ile Ser Trp Phe Val Asp Ser Lys Gln Val Gln Thr
            275                 280                 285

Ala Asn Thr Gln Pro Arg Glu Glu Gln Ser Asn Gly Thr Tyr Arg Val
290                 295                 300

Val Ser Val Leu Pro Ile Gly His Gln Asp Trp Leu Ser Gly Lys Gln
305                 310                 315                 320

Phe Lys Cys Lys Val Asn Asn Lys Ala Leu Pro Ser Pro Ile Glu Glu
                325                 330                 335

Ile Ile Ser Lys Thr Pro Gly Gln Ala His Gln Pro Asn Val Tyr Val
            340                 345                 350

Leu Pro Pro Ser Arg Asp Glu Met Ser Lys Asn Thr Val Thr Leu Thr
            355                 360                 365

Cys Leu Val Lys Asp Phe Phe Pro Pro Glu Ile Asp Val Glu Trp Gln
            370                 375                 380

Ser Asn Gly Gln Gln Glu Pro Glu Ser Lys Tyr Arg Met Thr Pro Pro
385                 390                 395                 400

Gln Leu Asp Glu Asp Gly Ser Tyr Phe Leu Tyr Ser Lys Leu Ser Val
                405                 410                 415

Asp Lys Ser Arg Trp Gln Arg Gly Asp Thr Phe Ile Cys Ala Val Met
            420                 425                 430

His Glu Ala Leu His Asn His Tyr Thr Gln Ile Ser Leu Ser His Ser
            435                 440                 445

Pro Gly Lys
    450

<210> SEQ ID NO 20
<211> LENGTH: 449
<212> TYPE: PRT
<213> ORGANISM: Artificial Sequence
<220> FEATURE:
<223> OTHER INFORMATION: Synthetic: Caninized heavy chain sequence from
      mouse antibody clone M14 and canine IgG-D

<400> SEQUENCE: 20

Glu Val Gln Leu Val Glu Ser Gly Pro Ser Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Thr Ile Ser Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Leu Val Thr Val Ser Ser Ala Ser Thr Thr Ala Pro Ser Val Phe Pro
            115                 120                 125

Leu Ala Pro Ser Cys Gly Ser Thr Ser Gly Ser Thr Val Ala Leu Ala
        130                 135                 140

Cys Leu Val Ser Gly Tyr Phe Pro Glu Pro Val Thr Val Ser Trp Asn
```

```
            145                 150                 155                 160
Ser Gly Ser Leu Thr Ser Gly Val His Thr Phe Pro Ser Val Leu Gln
                165                 170                 175

Ser Ser Gly Leu Tyr Ser Leu Ser Ser Thr Val Thr Val Pro Ser Ser
                180                 185                 190

Arg Trp Pro Ser Glu Thr Phe Thr Cys Asn Val Val His Pro Ala Ser
                195                 200                 205

Asn Thr Lys Val Asp Lys Pro Val Pro Lys Glu Ser Thr Cys Lys Cys
            210                 215                 220

Ile Ser Pro Cys Pro Val Pro Glu Ser Leu Gly Gly Pro Ser Val Phe
225                 230                 235                 240

Ile Phe Pro Pro Lys Pro Lys Asp Ile Leu Arg Ile Thr Arg Thr Pro
                245                 250                 255

Glu Ile Thr Cys Val Val Leu Asp Leu Gly Arg Glu Asp Pro Glu Val
                260                 265                 270

Gln Ile Ser Trp Phe Val Asp Gly Lys Glu Val His Thr Ala Lys Thr
                275                 280                 285

Gln Pro Arg Glu Gln Gln Phe Asn Ser Thr Tyr Arg Val Val Ser Val
            290                 295                 300

Leu Pro Ile Glu His Gln Asp Trp Leu Thr Gly Lys Glu Phe Lys Cys
305                 310                 315                 320

Arg Val Asn His Ile Gly Leu Pro Ser Pro Ile Glu Arg Thr Ile Ser
                325                 330                 335

Lys Ala Arg Gly Gln Ala His Gln Pro Ser Val Tyr Val Leu Pro Pro
                340                 345                 350

Ser Pro Lys Glu Leu Ser Ser Ser Asp Thr Val Thr Leu Thr Cys Leu
            355                 360                 365

Ile Lys Asp Phe Phe Pro Pro Glu Ile Asp Val Glu Trp Gln Ser Asn
            370                 375                 380

Gly Gln Pro Glu Pro Glu Ser Lys Tyr His Thr Thr Ala Pro Gln Leu
385                 390                 395                 400

Asp Glu Asp Gly Ser Tyr Phe Leu Tyr Ser Lys Leu Ser Val Asp Lys
                405                 410                 415

Ser Arg Trp Gln Gln Gly Asp Thr Phe Thr Cys Ala Val Met His Glu
                420                 425                 430

Ala Leu Gln Asn His Tyr Thr Asp Leu Ser Leu Ser His Ser Pro Gly
            435                 440                 445

Lys

<210> SEQ ID NO 21
<211> LENGTH: 221
<212> TYPE: PRT
<213> ORGANISM: Artificial Sequence
<220> FEATURE:
<223> OTHER INFORMATION: Synthetic: Caninized light chain sequence from
      mouse antibody clone M14 and canine light chain constant region

<400> SEQUENCE: 21

Asp Ile Val Met Thr Gln Ser Pro Ala Ser Leu Ser Val Ser Leu Gly
1               5                   10                  15

Gln Arg Ala Thr Ile Ser Cys Arg Ala Ser Glu Ser Val Asp Thr Tyr
                20                  25                  30

Gly Asn Ser Phe Met His Trp Tyr Gln Gln Lys Pro Gly Gln Ser Pro
                35                  40                  45

Lys Leu Leu Ile Tyr Arg Ala Ser Asn Leu Glu Ser Gly Ile Pro Ala
```

```
                50              55              60
Arg Phe Gly Gly Ser Gly Ser Gly Thr Asp Phe Thr Leu Thr Ile Asp
 65              70              75              80

Pro Val Gln Ala Asp Asp Val Ala Thr Tyr Tyr Cys Gln Gln Ser Tyr
                 85              90              95

Glu Asp Pro Trp Thr Phe Gly Gly Gly Thr Lys Leu Glu Ile Lys Arg
                100             105             110

Asn Asp Ala Gln Pro Ala Val Tyr Leu Phe Gln Pro Ser Pro Asp Gln
                115             120             125

Leu His Thr Gly Ser Ala Ser Val Val Cys Leu Leu Asn Ser Phe Tyr
                130             135             140

Pro Lys Asp Ile Asn Val Lys Trp Lys Val Asp Gly Val Ile Gln Asp
145             150             155             160

Thr Gly Ile Gln Glu Ser Val Thr Glu Gln Asp Lys Asp Ser Thr Tyr
                165             170             175

Ser Leu Ser Ser Thr Leu Thr Met Ser Ser Thr Glu Tyr Leu Ser His
                180             185             190

Glu Leu Tyr Ser Cys Glu Ile Thr His Lys Ser Leu Pro Ser Thr Leu
                195             200             205

Ile Lys Ser Phe Gln Arg Ser Glu Cys Gln Arg Val Asp
                210             215             220

<210> SEQ ID NO 22
<211> LENGTH: 159
<212> TYPE: PRT
<213> ORGANISM: Unknown
<220> FEATURE:
<223> OTHER INFORMATION: Canidae sp.
<220> FEATURE:
<221> NAME/KEY: misc_feature
<222> LOCATION: (1)..(159)
<223> OTHER INFORMATION: Canine IL31 amino acid sequence

<400> SEQUENCE: 22

Met Leu Ser His Thr Gly Pro Ser Arg Phe Ala Leu Phe Leu Leu Cys
 1               5              10              15

Ser Met Glu Thr Leu Leu Ser Ser His Met Ala Pro Thr His Gln Leu
                20              25              30

Pro Pro Ser Asp Val Arg Lys Ile Ile Leu Glu Leu Gln Pro Leu Ser
                35              40              45

Arg Gly Leu Leu Glu Asp Tyr Gln Lys Lys Glu Thr Gly Val Pro Glu
 50              55              60

Ser Asn Arg Thr Leu Leu Leu Cys Leu Thr Ser Asp Ser Gln Pro Pro
 65              70              75              80

Arg Leu Asn Ser Ser Ala Ile Leu Pro Tyr Phe Arg Ala Ile Arg Pro
                85              90              95

Leu Ser Asp Lys Asn Ile Ile Asp Lys Ile Ile Glu Gln Leu Asp Lys
                100             105             110

Leu Lys Phe Gln His Glu Pro Glu Thr Glu Ile Ser Val Pro Ala Asp
                115             120             125

Thr Phe Glu Cys Lys Ser Phe Ile Leu Thr Ile Leu Gln Gln Phe Ser
                130             135             140

Ala Cys Leu Glu Ser Val Phe Lys Ser Leu Asn Ser Gly Pro Gln
145             150             155

<210> SEQ ID NO 23
<211> LENGTH: 17
```

```
<212> TYPE: PRT
<213> ORGANISM: Unknown
<220> FEATURE:
<223> OTHER INFORMATION: Canidae sp.
<220> FEATURE:
<221> NAME/KEY: misc_feature
<222> LOCATION: (1)..(17)
<223> OTHER INFORMATION: Canine IL31 epitope

<400> SEQUENCE: 23

Pro Ser Asp Val Arg Lys Ile Ile Leu Glu Leu Gln Pro Leu Ser Arg
1               5                   10                  15

Gly

<210> SEQ ID NO 24
<211> LENGTH: 111
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(111)
<223> OTHER INFORMATION: Variable light chain amino acid sequence of
      mouse antibody clone M14

<400> SEQUENCE: 24

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Thr Tyr
                20                  25                  30

Gly Asn Ser Phe Met His Trp Tyr Gln Gln Lys Ser Gly Gln Ser Pro
            35                  40                  45

Lys Leu Leu Ile Tyr Arg Ala Ser Asn Leu Glu Ser Gly Ile Pro Ala
    50                  55                  60

Arg Phe Gly Gly Ser Gly Ser Arg Thr Asp Phe Thr Leu Thr Ile Asp
65                  70                  75                  80

Pro Val Glu Ala Asp Asp Val Ala Thr Tyr Tyr Cys Gln Gln Ser Tyr
                85                  90                  95

Glu Asp Pro Trp Thr Phe Gly Gly Gly Thr Lys Leu Glu Ile Lys
            100                 105                 110

<210> SEQ ID NO 25
<211> LENGTH: 118
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(118)
<223> OTHER INFORMATION: Variable heavy chain amino acid sequence of
      mouse antibody clone M14

<400> SEQUENCE: 25

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
                20                  25                  30

Tyr Trp Asn Trp Ile Arg Lys Phe Pro Gly Asn Lys Leu Glu Tyr Met
            35                  40                  45

Gly Tyr Ile Ser Tyr Ser Gly Ile Thr Asp Tyr Asn Pro Ser Leu Lys
    50                  55                  60
```

```
Ser Arg Ile Ser Ile Thr Arg Asp Thr Ser Lys Asn Gln Tyr Tyr Leu
 65                  70                  75                  80

Gln Leu Asn Ser Val Thr Thr Glu Asp Thr Ala Thr Tyr Tyr Cys Ala
                 85                  90                  95

Arg Tyr Gly Asn Tyr Gly Tyr Ala Met Asp Tyr Trp Gly Gln Gly Thr
            100                 105                 110

Ser Val Thr Val Ser Ser
            115

<210> SEQ ID NO 26
<211> LENGTH: 221
<212> TYPE: PRT
<213> ORGANISM: Artificial Sequence
<220> FEATURE:
<223> OTHER INFORMATION: Synthetic: Chimeric variable light chain of
      mouse antibody clone M14 and canine light chain constant region

<400> SEQUENCE: 26

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Thr Tyr
                 20                  25                  30

Gly Asn Ser Phe Met His Trp Tyr Gln Gln Lys Ser Gly Gln Ser Pro
             35                  40                  45

Lys Leu Leu Ile Tyr Arg Ala Ser Asn Leu Glu Ser Gly Ile Pro Ala
 50                  55                  60

Arg Phe Gly Gly Ser Gly Ser Arg Thr Asp Phe Thr Leu Thr Ile Asp
 65                  70                  75                  80

Pro Val Glu Ala Asp Asp Val Ala Thr Tyr Tyr Cys Gln Gln Ser Tyr
                 85                  90                  95

Glu Asp Pro Trp Thr Phe Gly Gly Thr Lys Leu Glu Ile Lys Arg
            100                 105                 110

Asn Asp Ala Gln Pro Ala Val Tyr Leu Phe Gln Pro Ser Pro Asp Gln
            115                 120                 125

Leu His Thr Gly Ser Ala Ser Val Val Cys Leu Leu Asn Ser Phe Tyr
        130                 135                 140

Pro Lys Asp Ile Asn Val Lys Trp Lys Val Asp Gly Val Ile Gln Asp
145                 150                 155                 160

Thr Gly Ile Gln Glu Ser Val Thr Glu Gln Asp Lys Asp Ser Thr Tyr
                165                 170                 175

Ser Leu Ser Ser Thr Leu Thr Met Ser Ser Thr Glu Tyr Leu Ser His
            180                 185                 190

Glu Leu Tyr Ser Cys Glu Ile Thr His Lys Ser Leu Pro Ser Thr Leu
        195                 200                 205

Ile Lys Ser Phe Gln Arg Ser Glu Cys Gln Arg Val Asp
    210                 215                 220

<210> SEQ ID NO 27
<211> LENGTH: 453
<212> TYPE: PRT
<213> ORGANISM: Artificial Sequence
<220> FEATURE:
<223> OTHER INFORMATION: Synthetic: Chimeric variable heavy chain of
      mouse antibody clone M14 and canine IgG-B

<400> SEQUENCE: 27

Glu Val Gln Leu Gln Glu Ser Gly Pro Ser Leu Val Lys Pro Ser Gln
 1               5                  10                  15
```

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
            35                  40                  45

Gly Tyr Ile Ser Tyr Ser Gly Ile Thr Asp Tyr Asn Pro Ser Leu Lys
        50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Ser Val Thr Val Ser Ser Ala Ser Thr Thr Ala Pro Ser Val Phe Pro
            115                 120                 125

Leu Ala Pro Ser Cys Gly Ser Thr Ser Gly Ser Thr Val Ala Leu Ala
        130                 135                 140

Cys Leu Val Ser Gly Tyr Phe Pro Glu Pro Val Thr Val Ser Trp Asn
145                 150                 155                 160

Ser Gly Ser Leu Thr Ser Gly Val His Thr Phe Pro Ser Val Leu Gln
                165                 170                 175

Ser Ser Gly Leu Tyr Ser Leu Ser Ser Met Val Thr Val Pro Ser Ser
            180                 185                 190

Arg Trp Pro Ser Glu Thr Phe Thr Cys Asn Val Ala His Pro Ala Ser
            195                 200                 205

Lys Thr Lys Val Asp Lys Pro Val Pro Lys Arg Glu Asn Gly Arg Val
    210                 215                 220

Pro Arg Pro Pro Asp Cys Pro Lys Cys Pro Ala Pro Glu Met Leu Gly
225                 230                 235                 240

Gly Pro Ser Val Phe Ile Phe Pro Pro Lys Pro Lys Asp Thr Leu Leu
                245                 250                 255

Ile Ala Arg Thr Pro Glu Val Thr Cys Val Val Val Asp Leu Asp Pro
            260                 265                 270

Glu Asp Pro Glu Val Gln Ile Ser Trp Phe Val Asp Gly Lys Gln Met
        275                 280                 285

Gln Thr Ala Lys Thr Gln Pro Arg Glu Glu Gln Phe Asn Gly Thr Tyr
    290                 295                 300

Arg Val Val Ser Val Leu Pro Ile Gly His Gln Asp Trp Leu Lys Gly
305                 310                 315                 320

Lys Gln Phe Thr Cys Lys Val Asn Asn Lys Ala Leu Pro Ser Pro Ile
                325                 330                 335

Glu Arg Thr Ile Ser Lys Ala Arg Gly Gln Ala His Gln Pro Ser Val
            340                 345                 350

Tyr Val Leu Pro Pro Ser Arg Glu Glu Leu Ser Lys Asn Thr Val Ser
        355                 360                 365

Leu Thr Cys Leu Ile Lys Asp Phe Phe Pro Pro Asp Ile Asp Val Glu
    370                 375                 380

Trp Gln Ser Asn Gly Gln Gln Glu Pro Glu Ser Lys Tyr Arg Thr Thr
385                 390                 395                 400

Pro Pro Gln Leu Asp Glu Asp Gly Ser Tyr Phe Leu Tyr Ser Lys Leu
                405                 410                 415

Ser Val Asp Lys Ser Arg Trp Gln Arg Gly Asp Thr Phe Ile Cys Ala
            420                 425                 430

Val Met His Glu Ala Leu His Asn His Tyr Thr Gln Glu Ser Leu Ser

His Ser Pro Gly Lys
    450

<210> SEQ ID NO 28
<211> LENGTH: 159
<212> TYPE: PRT
<213> ORGANISM: Felis catus
<220> FEATURE:
<221> NAME/KEY: misc_feature
<222> LOCATION: (1)..(159)
<223> OTHER INFORMATION: Feline IL31 amino acid sequence

<400> SEQUENCE: 28

Met Leu Ser His Ala Gly Pro Ala Arg Phe Ala Leu Phe Leu Leu Cys
1               5                   10                  15

Cys Met Glu Thr Leu Leu Pro Ser His Met Ala Pro Ala His Arg Leu
            20                  25                  30

Gln Pro Ser Asp Val Arg Lys Ile Ile Leu Glu Leu Arg Pro Met Ser
        35                  40                  45

Lys Gly Leu Leu Gln Asp Tyr Leu Lys Lys Glu Ile Gly Leu Pro Glu
    50                  55                  60

Ser Asn His Ser Ser Leu Pro Cys Leu Ser Ser Asp Ser Gln Leu Pro
65                  70                  75                  80

His Ile Asn Gly Ser Ala Ile Leu Pro Tyr Phe Arg Ala Ile Arg Pro
                85                  90                  95

Leu Ser Asp Lys Asn Thr Ile Asp Lys Ile Ile Glu Gln Leu Asp Lys
            100                 105                 110

Leu Lys Phe Gln Arg Glu Pro Glu Ala Lys Val Ser Met Pro Ala Asp
        115                 120                 125

Asn Phe Glu Arg Lys Asn Phe Ile Leu Ala Val Leu Gln Gln Phe Ser
    130                 135                 140

Ala Cys Leu Glu His Val Leu Gln Ser Leu Asn Ser Gly Pro Gln
145                 150                 155

<210> SEQ ID NO 29
<211> LENGTH: 209
<212> TYPE: PRT
<213> ORGANISM: Equus caballus
<220> FEATURE:
<221> NAME/KEY: misc_feature
<222> LOCATION: (1)..(209)
<223> OTHER INFORMATION: Equine IL31 amino acid sequence

<400> SEQUENCE: 29

Met Val Ser His Ile Gly Ser Thr Arg Phe Ala Leu Phe Leu Leu Cys
1               5                   10                  15

Cys Leu Gly Thr Leu Met Phe Ser His Thr Gly Pro Ile Tyr Gln Leu
            20                  25                  30

Gln Pro Lys Glu Ile Gln Ala Ile Ile Val Glu Leu Gln Asn Leu Ser
        35                  40                  45

Lys Lys Leu Leu Asp Asp Tyr Leu Asn Lys Glu Lys Gly Val Gln Lys
    50                  55                  60

Phe Asp Ser Asp Leu Pro Ser Cys Phe Thr Ser Asp Ser Gln Ala Pro
65                  70                  75                  80

Gly Asn Ile Asn Ser Ser Ala Ile Leu Pro Tyr Phe Lys Ala Ile Ser
                85                  90                  95

Pro Ser Leu Asn Asn Asp Lys Ser Leu Tyr Ile Ile Glu Gln Leu Asp
            100                 105                 110

```
Lys Leu Asn Phe Gln Asn Ala Pro Glu Thr Glu Val Ser Met Pro Thr
            115                 120                 125
Asp Asn Phe Glu Arg Lys Arg Phe Ile Leu Thr Ile Leu Arg Trp Phe
    130                 135                 140
Ser Asn Cys Leu Glu Leu Ala Met Lys Thr Leu Thr Thr Ala Glu Gln
145                 150                 155                 160
Ala Leu Pro Pro Leu Asp Pro Ser Thr Pro His Ala Gly Ala Val Ala
                165                 170                 175
Leu Thr His His Gln Gln Asp Arg Thr Ala Leu Asp Arg Ala Val Phe
            180                 185                 190
Pro Phe Val Trp Ala Ala Pro Arg Gly Gly Glu Val Gly Asp Gly Gly
            195                 200                 205
His

<210> SEQ ID NO 30
<211> LENGTH: 221
<212> TYPE: PRT
<213> ORGANISM: Artificial Sequence
<220> FEATURE:
<223> OTHER INFORMATION: Synthetic: Chimeric variable light chain of
      mouse antibody clone M14 and feline light chain constant region

<400> SEQUENCE: 30

Asp Ile Val Leu Thr Gln Ser Pro Ala Ser Leu Ala Val Ser Leu Gly
1               5                   10                  15
Gln Arg Ala Thr Ile Ser Cys Arg Ala Ser Glu Ser Val Asp Thr Tyr
            20                  25                  30
Gly Asn Ser Phe Met His Trp Tyr Gln Gln Lys Ser Gly Gln Ser Pro
        35                  40                  45
Lys Leu Leu Ile Tyr Arg Ala Ser Asn Leu Glu Ser Gly Ile Pro Ala
    50                  55                  60
Arg Phe Gly Gly Ser Gly Ser Arg Thr Asp Phe Thr Leu Thr Ile Asp
65                  70                  75                  80
Pro Val Glu Ala Asp Asp Val Ala Thr Tyr Tyr Cys Gln Gln Ser Tyr
                85                  90                  95
Glu Asp Pro Trp Thr Phe Gly Gly Gly Thr Lys Leu Glu Ile Lys Arg
            100                 105                 110
Ser Asp Ala Gln Pro Ser Val Phe Leu Phe Gln Pro Ser Leu Asp Glu
        115                 120                 125
Leu His Thr Gly Ser Ala Ser Ile Val Cys Ile Leu Asn Asp Phe Tyr
    130                 135                 140
Pro Lys Glu Val Asn Val Lys Trp Lys Val Asp Gly Val Val Gln Asn
145                 150                 155                 160
Lys Gly Ile Gln Glu Ser Thr Thr Glu Gln Asn Ser Lys Asp Ser Thr
                165                 170                 175
Tyr Ser Leu Ser Ser Thr Leu Thr Met Ser Ser Thr Glu Tyr Gln Ser
            180                 185                 190
His Glu Lys Phe Ser Cys Glu Val Thr His Lys Ser Leu Ala Ser Thr
        195                 200                 205
Leu Val Lys Ser Phe Asn Arg Ser Glu Cys Gln Arg Glu
    210                 215                 220

<210> SEQ ID NO 31
<211> LENGTH: 453
<212> TYPE: PRT
<213> ORGANISM: Artificial Sequence
```

<220> FEATURE:
<223> OTHER INFORMATION: Synthetic: Chimeric variable heavy chain of
      mouse antibody clone M14 and feline heavy chain constant region

<400> SEQUENCE: 31

Glu Val Gln Leu Gln Glu Ser Gly Pro Ser Leu Val Lys Pro Ser Gln
1               5                   10                  15

Thr Leu Ser Leu Thr Cys Ser Val Thr Gly Asp Ser Ile Thr Ser Gly
            20                  25                  30

Tyr Trp Asn Trp Ile Arg Lys Phe Pro Gly Asn Lys Leu Glu Tyr Met
        35                  40                  45

Gly Tyr Ile Ser Tyr Ser Gly Ile Thr Asp Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Ser Val Thr Val Ser Ser Ala Ser Thr Thr Ala Pro Ser Val Phe Pro
        115                 120                 125

Leu Ala Pro Ser Cys Gly Thr Thr Ser Gly Ala Thr Val Ala Leu Ala
    130                 135                 140

Cys Leu Val Leu Gly Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ala Ser Gly Leu Tyr Ser Leu Ser Ser Met Val Thr Val Pro Ser Ser
            180                 185                 190

Arg Trp Leu Ser Asp Thr Phe Thr Cys Asn Val Ala His Pro Pro Ser
        195                 200                 205

Asn Thr Lys Val Asp Lys Thr Val Arg Lys Thr Asp His Pro Pro Gly
    210                 215                 220

Pro Lys Pro Cys Asp Cys Pro Lys Cys Pro Pro Pro Glu Met Leu Gly
225                 230                 235                 240

Gly Pro Ser Ile Phe Ile Phe Pro Pro Lys Pro Lys Asp Thr Leu Ser
                245                 250                 255

Ile Ser Arg Thr Pro Glu Val Thr Cys Leu Val Val Asp Leu Gly Pro
            260                 265                 270

Asp Asp Ser Asp Val Gln Ile Thr Trp Phe Val Asp Asn Thr Gln Val
        275                 280                 285

Tyr Thr Ala Lys Thr Ser Pro Arg Glu Glu Gln Phe Asn Ser Thr Tyr
    290                 295                 300

Arg Val Val Ser Val Leu Pro Ile Leu His Gln Asp Trp Leu Lys Gly
305                 310                 315                 320

Lys Glu Phe Lys Cys Lys Val Asn Ser Lys Ser Leu Pro Ser Pro Ile
                325                 330                 335

Glu Arg Thr Ile Ser Lys Ala Lys Gly Gln Pro His Glu Pro Gln Val
            340                 345                 350

Tyr Val Leu Pro Pro Ala Gln Glu Glu Leu Ser Arg Asn Lys Val Ser
        355                 360                 365

Val Thr Cys Leu Ile Lys Ser Phe His Pro Pro Asp Ile Ala Val Glu
    370                 375                 380

Trp Glu Ile Thr Gly Gln Pro Glu Pro Glu Asn Asn Tyr Arg Thr Thr

```
385                 390                 395                 400
Pro Pro Gln Leu Asp Ser Asp Gly Thr Tyr Phe Val Tyr Ser Lys Leu
            405                 410                 415

Ser Val Asp Arg Ser His Trp Gln Arg Gly Asn Thr Tyr Thr Cys Ser
            420                 425                 430

Val Ser His Glu Ala Leu His Ser His His Thr Gln Lys Ser Leu Thr
            435                 440                 445

Gln Ser Pro Gly Lys
        450
```

<210> SEQ ID NO 32
<211> LENGTH: 111
<212> TYPE: PRT
<213> ORGANISM: Artificial Sequence
<220> FEATURE:
<223> OTHER INFORMATION: Synthetic: Felinized variable light chain
      sequence from mouse antibody clone M14

<400> SEQUENCE: 32

```
Glu Ile Gln Met Thr Gln Ser Pro Ser Ser Leu Ser Ala Ser Pro Gly
1               5                   10                  15

Asp Arg Val Thr Ile Ser Cys Arg Ala Ser Glu Ser Val Asp Thr Tyr
            20                  25                  30

Gly Asn Ser Phe Met His Trp Tyr Gln Gln Lys Pro Gly Gln Ser Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Ala Ala Thr Tyr Tyr Cys Gln Gln Ser Tyr
                85                  90                  95

Glu Asp Pro Trp Thr Phe Gly Gly Gly Thr Lys Leu Glu Ile Lys
            100                 105                 110
```

<210> SEQ ID NO 33
<211> LENGTH: 118
<212> TYPE: PRT
<213> ORGANISM: Artificial Sequence
<220> FEATURE:
<223> OTHER INFORMATION: Synthetic: Felinized variable heavy chain
      sequence from mouse antibody clone M14

<400> SEQUENCE: 33

```
Asp Val Gln Leu Val Glu Ser Gly Gly Asp Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Asn Trp Val Arg Gln Ala Pro Gly Lys Gly Leu Gln Trp Val
        35                  40                  45

Ala Tyr Ile Ser Tyr Ser Gly Ile Thr Asp Tyr Ala Asp Ser Val Lys
    50                  55                  60

Gly Arg Phe Thr Ile Ser Arg Asp Asn Ala Lys Asn Thr Leu Tyr Leu
65                  70                  75                  80

Gln Leu Asn Asn Leu Lys Ala Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Leu Val Thr Val Ser Ser
```

<210> SEQ ID NO 34
<211> LENGTH: 221
<212> TYPE: PRT
<213> ORGANISM: Artificial Sequence
<220> FEATURE:
<223> OTHER INFORMATION: Synthetic: Felinized variable light chain
      sequence from mouse antibody clone M14

<400> SEQUENCE: 34

Glu Ile Gln Met Thr Gln Ser Pro Ser Ser Leu Ser Ala Ser Pro Gly
1               5                   10                  15

Asp Arg Val Thr Ile Ser Cys Arg Ala Ser Glu Ser Val Asp Thr Tyr
            20                  25                  30

Gly Asn Ser Phe Met His Trp Tyr Gln Gln Lys Pro Gly Gln Ser Pro
        35                  40                  45

Lys Leu Leu Ile Tyr Arg Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Glu Pro Glu Asp Ala Ala Thr Tyr Tyr Cys Gln Gln Ser Tyr
                85                  90                  95

Glu Asp Pro Trp Thr Phe Gly Gly Gly Thr Lys Leu Glu Ile Lys Arg
            100                 105                 110

Ser Asp Ala Gln Pro Ser Val Phe Leu Phe Gln Pro Ser Leu Asp Glu
        115                 120                 125

Leu His Thr Gly Ser Ala Ser Ile Val Cys Ile Leu Asn Asp Phe Tyr
    130                 135                 140

Pro Lys Glu Val Asn Val Lys Trp Lys Val Asp Gly Val Val Gln Asn
145                 150                 155                 160

Lys Gly Ile Gln Glu Ser Thr Thr Glu Gln Asn Ser Lys Asp Ser Thr
                165                 170                 175

Tyr Ser Leu Ser Ser Thr Leu Thr Met Ser Ser Thr Glu Tyr Gln Ser
            180                 185                 190

His Glu Lys Phe Ser Cys Glu Val Thr His Lys Ser Leu Ala Ser Thr
        195                 200                 205

Leu Val Lys Ser Phe Asn Arg Ser Glu Cys Gln Arg Glu
    210                 215                 220

<210> SEQ ID NO 35
<211> LENGTH: 453
<212> TYPE: PRT
<213> ORGANISM: Artificial Sequence
<220> FEATURE:
<223> OTHER INFORMATION: Synthetic: Felinized variable heavy chain
      sequence from mouse antibody clone M14

<400> SEQUENCE: 35

Asp Val Gln Leu Val Glu Ser Gly Gly Asp Leu Val Lys Pro Gly Gly
1               5                   10                  15

Ser Leu Arg Leu Thr Cys Ser Val Thr Gly Asp Ser Ile Thr Ser Gly
            20                  25                  30

Tyr Trp Asn Trp Val Arg Gln Ala Pro Gly Lys Gly Leu Gln Trp Val
        35                  40                  45

Ala Tyr Ile Ser Tyr Ser Gly Ile Thr Asp Tyr Ala Asp Ser Val Lys
    50                  55                  60

Gly Arg Phe Thr Ile Ser Arg Asp Asn Ala Lys Asn Thr Leu Tyr Leu

```
                65                  70                  75                  80
Gln Leu Asn Asn Leu Lys Ala Glu Asp Thr Ala Thr Tyr Tyr Cys Ala
                85                  90                  95

Arg Tyr Gly Asn Tyr Gly Tyr Ala Met Asp Tyr Trp Gly Gln Gly Thr
            100                 105                 110

Leu Val Thr Val Ser Ser Ala Ser Thr Thr Ala Pro Ser Val Phe Pro
            115                 120                 125

Leu Ala Pro Ser Cys Gly Thr Thr Ser Gly Ala Thr Val Ala Leu Ala
130                 135                 140

Cys Leu Val Leu Gly Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ala Ser Gly Leu Tyr Ser Leu Ser Ser Met Val Thr Val Pro Ser Ser
            180                 185                 190

Arg Trp Leu Ser Asp Thr Phe Thr Cys Asn Val Ala His Pro Pro Ser
            195                 200                 205

Asn Thr Lys Val Asp Lys Thr Val Arg Lys Thr Asp His Pro Pro Gly
        210                 215                 220

Pro Lys Pro Cys Asp Cys Pro Lys Cys Pro Pro Pro Glu Met Leu Gly
225                 230                 235                 240

Gly Pro Ser Ile Phe Ile Phe Pro Pro Lys Pro Lys Asp Thr Leu Ser
                245                 250                 255

Ile Ser Arg Thr Pro Glu Val Thr Cys Leu Val Val Asp Leu Gly Pro
            260                 265                 270

Asp Asp Ser Asp Val Gln Ile Thr Trp Phe Val Asp Asn Thr Gln Val
            275                 280                 285

Tyr Thr Ala Lys Thr Ser Pro Arg Glu Glu Gln Phe Asn Ser Thr Tyr
        290                 295                 300

Arg Val Val Ser Val Leu Pro Ile Leu His Gln Asp Trp Leu Lys Gly
305                 310                 315                 320

Lys Glu Phe Lys Cys Lys Val Asn Ser Lys Ser Leu Pro Ser Pro Ile
                325                 330                 335

Glu Arg Thr Ile Ser Lys Ala Lys Gly Gln Pro His Glu Pro Gln Val
            340                 345                 350

Tyr Val Leu Pro Pro Ala Gln Glu Glu Leu Ser Arg Asn Lys Val Ser
            355                 360                 365

Val Thr Cys Leu Ile Lys Ser Phe His Pro Pro Asp Ile Ala Val Glu
370                 375                 380

Trp Glu Ile Thr Gly Gln Pro Glu Pro Glu Asn Asn Tyr Arg Thr Thr
385                 390                 395                 400

Pro Pro Gln Leu Asp Ser Asp Gly Thr Tyr Phe Val Tyr Ser Lys Leu
                405                 410                 415

Ser Val Asp Arg Ser His Trp Gln Arg Gly Asn Thr Tyr Thr Cys Ser
            420                 425                 430

Val Ser His Glu Ala Leu His Ser His His Thr Gln Lys Ser Leu Thr
            435                 440                 445

Gln Ser Pro Gly Lys
        450

<210> SEQ ID NO 36
<211> LENGTH: 238
<212> TYPE: PRT
<213> ORGANISM: Unknown
```

```
<220> FEATURE:
<223> OTHER INFORMATION: Murinae sp.
<220> FEATURE:
<221> NAME/KEY: misc_feature
<222> LOCATION: (1)..(238)
<223> OTHER INFORMATION: M14_LC

<400> SEQUENCE: 36

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Cys Arg Ala Ser Glu Ser
        35                  40                  45

Val Asp Thr Tyr Gly Asn Ser Phe Met His Trp Tyr Gln Gln Lys Ser
    50                  55                  60

Gly Gln Ser Pro Lys Leu Leu Ile Tyr Arg Ala Ser Asn Leu Glu Ser
65                  70                  75                  80

Gly Ile Pro Ala Arg Phe Gly Gly Ser Gly Ser Arg Thr Asp Phe Thr
                85                  90                  95

Leu Thr Ile Asp Pro Val Glu Ala Asp Asp Val Ala Thr Tyr Tyr Cys
            100                 105                 110

Gln Gln Ser Tyr Glu Asp Pro Trp Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 37
<211> LENGTH: 238
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(238)
<223> OTHER INFORMATION: M18_LC

<400> SEQUENCE: 37

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Pro Gly Gln Arg Ala Thr Ile Ser Cys Arg Ala Ser Glu Ser
        35                  40                  45

Val Asp Thr Tyr Gly Asn Ser Phe Ile His Trp Tyr Gln Gln Lys Pro
    50                  55                  60
```

```
Gly Gln Ser Pro Lys Leu Leu Ile Tyr Arg Ala Ser Asn Leu Glu Ser
 65                  70                  75                  80

Gly Ile Pro Ala Arg Phe Ser Gly Ser Gly Ser Arg Thr Asp Phe Thr
                 85                  90                  95

Leu Thr Ile Asn Pro Val Glu Thr Asp Val Ala Thr Tyr Tyr Cys
                100                 105                 110

Gln Gln Ser Tyr Glu Asp Pro Trp Thr Phe Gly Gly Gly Thr Lys Leu
                115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
                180                 185                 190

Lys Asp Ser Thr Tyr Ser Met Ser Ser Thr Leu Thr Leu Thr Lys Asp
                195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Asn Glu Cys
225                 230                 235

<210> SEQ ID NO 38
<211> LENGTH: 238
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(238)
<223> OTHER INFORMATION: M19_LC

<400> SEQUENCE: 38

Met Glu Thr Asp Thr Leu Leu Trp Val Leu Leu Leu Trp Val Pro
  1               5                  10                  15

Gly Ser Thr Gly Asp Ile Val Leu Thr Gln Ser Pro Ala Ser Leu Ala
                 20                  25                  30

Val Ser Leu Gly Gln Arg Ala Thr Ile Ser Cys Arg Ala Ser Glu Ser
                 35                  40                  45

Val Asp Thr Tyr Gly Asn Ser Phe Met His Trp Tyr Gln Gln Lys Pro
 50                  55                  60

Gly Gln Pro Pro Lys Leu Leu Ile Tyr Arg Ala Ser Asn Leu Glu Ser
 65                  70                  75                  80

Gly Ile Pro Ala Arg Phe Ser Gly Ser Gly Ser Arg Thr Asp Phe Thr
                 85                  90                  95

Leu Thr Ile Asn Pro Val Glu Ala Asp Ile Ala Thr Tyr Tyr Cys
                100                 105                 110

Gln Gln Ser Tyr Glu Asp Pro Trp Thr Phe Gly Gly Gly Thr Lys Leu
                115                 120                 125

Glu Ile Lys Arg Ala Asp Ala Ala Pro Thr Val Ser Ile Phe Pro Pro
130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
```

165                 170                 175
Ser Glu Arg Gln Asn Gly Val Leu Asn Ser Trp Thr Asp Gln Asp Ser
                180                 185                 190

Lys Asp Ser Thr Tyr Ser Met Ser Ser Thr Leu Thr Leu Thr Lys Asp
            195                 200                 205

Glu Tyr Glu Arg His Asn Ser Tyr Thr Cys Glu Ala Thr His Lys Thr
        210                 215                 220

Ser Thr Ser Pro Ile Val Lys Ser Phe Asn Arg Asn Glu Cys
225                 230                 235

<210> SEQ ID NO 39
<211> LENGTH: 238
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(238)
<223> OTHER INFORMATION: M87_LC

<400> SEQUENCE: 39

Met Glu Thr Asp Thr Leu Leu Leu Trp Val Leu Leu Leu Trp Val Pro
1               5                   10                  15

Gly Ser Thr Gly Asp Ile Val Leu Thr Gln Ser Pro Ala Ser Leu Ala
            20                  25                  30

Val Ser Leu Gly Gln Arg Ala Thr Ile Ser Tyr Arg Ala Ser Lys Ser
        35                  40                  45

Val Ser Thr Ser Gly Tyr Ser Tyr Met His Trp Asn Gln Gln Lys Pro
    50                  55                  60

Gly Gln Pro Pro Arg Leu Leu Ile Tyr Leu Val Ser Asn Leu Glu Ser
65                  70                  75                  80

Gly Val Pro Ala Arg Phe Ser Gly Ser Gly Ser Gly Thr Asp Phe Thr
                85                  90                  95

Leu Asn Ile His Pro Val Glu Glu Glu Asp Ala Ala Thr Tyr Tyr Cys
            100                 105                 110

Gln His Ile Arg Glu Leu Thr Arg Ser Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235

<210> SEQ ID NO 40
<211> LENGTH: 152
<212> TYPE: PRT
<213> ORGANISM: Unknown
<220> FEATURE:

```
<223> OTHER INFORMATION: Murinae sp.
<220> FEATURE:
<221> NAME/KEY: misc_feature
<222> LOCATION: (1)..(152)
<223> OTHER INFORMATION: M14_HC

<400> SEQUENCE: 40

Met Ala Val Leu Gly Leu Leu Cys Leu Val Thr Phe Pro Ser Cys
1               5                   10                  15

Val Leu Ser Glu Val Gln Leu Gln Glu Ser Gly Pro Ser Leu Val Lys
            20                  25                  30

Pro Ser Gln Thr Leu Ser Leu Thr Cys Ser Val Thr Gly Asp Ser Ile
            35                  40                  45

Thr Ser Gly Tyr Trp Asn Trp Ile Arg Lys Phe Pro Gly Asn Lys Leu
        50                  55                  60

Glu Tyr Met Gly Tyr Ile Ser Tyr Ser Gly Ile Thr Asp Tyr Asn Pro
65                  70                  75                  80

Ser Leu Lys Ser Arg Ile Ser Ile Thr Arg Asp Thr Ser Lys Asn Gln
                85                  90                  95

Tyr Tyr Leu Gln Leu Asn Ser Val Thr Thr Glu Asp Thr Ala Thr Tyr
            100                 105                 110

Tyr Cys Ala Arg Tyr Gly Asn Tyr Gly Tyr Ala Met Asp Tyr Trp Gly
            115                 120                 125

Gln Gly Thr Ser Val Thr Val Ser Ser Ala Lys Thr Thr Pro Pro Ser
        130                 135                 140

Val Tyr Pro Leu Ala Pro Gly Ser
145                 150

<210> SEQ ID NO 41
<211> LENGTH: 152
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(152)
<223> OTHER INFORMATION: M19_HC

<400> SEQUENCE: 41

Met Ala Val Leu Gly Leu Leu Phe Cys Leu Val Thr Phe Pro Ser Cys
1               5                   10                  15

Val Leu Ser Glu Val Gln Leu Gln Glu Ser Gly Pro Ser Leu Val Lys
            20                  25                  30

Pro Ser Gln Thr Leu Ser Leu Thr Cys Ser Val Thr Gly Asp Ser Ile
            35                  40                  45

Thr Ser Gly Tyr Trp Asn Trp Ile Arg Lys Phe Pro Gly Asn Lys Leu
        50                  55                  60

Glu Tyr Met Gly Tyr Ile Ser Tyr Ser Gly Ile Thr Asp Tyr Asn Pro
65                  70                  75                  80

Ser Leu Lys Ser Arg Ile Ser Ile Thr Arg Asp Thr Ser Lys Asn Gln
                85                  90                  95

Tyr Tyr Leu Gln Leu Asn Ser Val Thr Thr Glu Asp Thr Ala Thr Tyr
            100                 105                 110

Tyr Cys Ala Arg Tyr Gly Asn Tyr Gly Tyr Ala Met Asp Tyr Trp Gly
            115                 120                 125

Gln Gly Thr Ser Val Thr Val Ser Ser Ala Lys Thr Thr Pro Pro Ser
        130                 135                 140
```

Val Tyr Pro Leu Ala Pro Gly Ser
145                 150

<210> SEQ ID NO 42
<211> LENGTH: 152
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(152)
<223> OTHER INFORMATION: M18_HC

<400> SEQUENCE: 42

Met Ala Val Leu Gly Leu Leu Phe Cys Leu Val Thr Phe Pro Ser Cys
1               5                   10                  15

Val Leu Ser Glu Val Gln Leu Gln Glu Ser Gly Pro Ser Leu Val Lys
            20                  25                  30

Pro Ser Gln Thr Leu Ser Leu Thr Cys Ser Val Thr Gly Asp Ser Ile
        35                  40                  45

Thr Ser Gly Tyr Trp Asn Trp Ile Arg Lys Phe Pro Gly Asn Glu Leu
    50                  55                  60

Glu Tyr Met Gly Tyr Ile Ser Tyr Ser Gly Ile Thr Tyr Tyr Asn Pro
65                  70                  75                  80

Ser Leu Lys Ser Arg Phe Ser Ile Thr Arg Asp Thr Ser Lys Asn Gln
                85                  90                  95

Tyr Tyr Leu Gln Leu Asn Ser Val Thr Thr Glu Asp Thr Ala Thr Tyr
            100                 105                 110

Tyr Cys Ala Arg Tyr Gly Asn Tyr Gly Tyr Ala Met Asp Tyr Trp Gly
        115                 120                 125

Gln Gly Thr Ser Val Thr Val Ser Ser Ala Lys Thr Thr Pro Pro Ser
    130                 135                 140

Val Tyr Pro Leu Ala Pro Gly Ser
145                 150

<210> SEQ ID NO 43
<211> LENGTH: 154
<212> TYPE: PRT
<213> ORGANISM: Unknown
<220> FEATURE:
<223> OTHER INFORMATION: Murinae sp.
<220> FEATURE:
<221> NAME/KEY: misc_feature
<222> LOCATION: (1)..(154)
<223> OTHER INFORMATION: M87_HC

<400> SEQUENCE: 43

Met Ala Val Leu Gly Leu Leu Phe Cys Leu Val Thr Phe Pro Ser Cys
1               5                   10                  15

Val Leu Ser Glu Val Lys Leu Val Glu Ser Gly Gly Gly Leu Val Gln
            20                  25                  30

Pro Gly Gly Ser Leu Arg Leu Ser Cys Ala Thr Ser Gly Phe Thr Phe
        35                  40                  45

Thr Asp Tyr Tyr Met Asn Trp Val Arg Gln Pro Pro Gly Lys Ala Leu
    50                  55                  60

Glu Trp Leu Gly Phe Ile Arg Asn Lys Ala Asn Gly Tyr Thr Thr Glu
65                  70                  75                  80

Tyr Ser Ala Ser Val Lys Gly Arg Phe Thr Ile Ser Arg Asp Asn Ser
                85                  90                  95

```
Gln Ser Ile Leu Tyr Leu Gln Met Asn Thr Leu Arg Ala Glu Asp Ser
            100                 105                 110
Ala Thr Tyr Tyr Cys Ala Arg Asp Tyr Tyr Gly Ser Cys Phe Asp Tyr
        115                 120                 125
Trp Gly Gln Gly Thr Thr Leu Thr Val Ser Ser Ala Lys Thr Thr Pro
    130                 135                 140
Pro Ser Val Tyr Pro Leu Ala Pro Gly Ser
145                 150
```